United States Patent [19]
Wittman et al.

[11] Patent Number: 5,773,461
[45] Date of Patent: Jun. 30, 1998

[54] 7-DEOXY-6-SUBSTITUTED PACLITAXELS

[75] Inventors: Mark D. Wittman, Cheshire; Thomas J. Altstadt, Middletown; John F. Kadow, Wallingford, all of Conn.; David G. I. Kingston, Blacksburg, Va.; Xian Liang, Boulder, Colo.

[73] Assignees: Bristol-Myers Squibb Company, Princeton, N.J.; Virginia Tech Intellectual Properties, Inc., Blacksburg, Va.

[21] Appl. No.: 868,758

[22] Filed: Jun. 4, 1997

Related U.S. Application Data

[60] Provisional application No. 60/042,599, Apr. 21, 1997 and provisional application No. 60/019,493, Jun. 6, 1996.

[51] Int. Cl.$^6$ .................. A61K 31/335; C07D 305/14
[52] U.S. Cl. .................. 514/449; 549/510; 549/511
[58] Field of Search .................. 549/510, 511; 514/449

[56] References Cited

U.S. PATENT DOCUMENTS 5,489,601  2/1996  Holton et al. .................. 514/337

*Primary Examiner*—Ba K. Trinh
*Attorney, Agent, or Firm*—Samuel J. DuBoff

[57] ABSTRACT

The present invention concerns novel paclitaxel derivatives, their use as antitumor agents, and pharmaceutical formulations.

10 Claims, No Drawings

7-DEOXY-6-SUBSTITUTED PACLITAXELS

This application claims the priority of provisional applications 60/019,493 and 60/042,599 filed Jun. 6, 1996 and Apr. 2, 1997 respectively.

BACKGROUND OF THE INVENTION

FIELD OF THE INVENTION

The present invention concerns antitumor compounds. More particularly, the invention provides novel paclitaxel derivatives, pharmaceutical formulations thereof, and their use as antitumor agents.

BACKGROUND ART

Taxol® (paclitaxel) is a natural product extracted from the bark of Pacific yew trees, Taxus brevifolia. It has been shown to have excellent antitumor activity in in vivo animal models, and recent studies have elucidated its unique mode of action, which involves abnormal polymerization of tubulin and disruption of mitosis. It has recently been approved for the treatment of refractory advanced ovarian cancer and breast cancer; and studies involving other cancers have shown promising results. The results of paclitaxel clinical studies are reviewed by numerous authors, such as by Rowinsky and Donehower in "The Clinical Pharmacology and Use of Antimicrotubule Agents in Cancer Chemotherapeutics," *Pharmac. Ther.* 52:35–84, 1991; by Spencer and Faulds in "Paclitaxel, A Review of its Pharmacodynamic and Pharmacokinetic Properties and Therapeutic Potential in the Treatment of Cancer," *Drugs*, 48 (5) 794–847, 1994; by K. C. Nicolaou et al. in "Chemistry and Biology of Taxol," *Angew. Chem., Int. Ed. Engl.*, 33: 15–44, 1994; by F. A. Holmes, A. P. Kudelka, J. J. Kavanaugh, M. H. Huber, J. A. Ajani, V. Valero in the book "Taxane Anticancer Agents Basic Science and Current Status" edited by Gunda I. Georg, Thomas T. Chen, Iwao Ojima, and Dolotrai M. Vyas, 1995, American Chemical Society, Washington, DC, 31–57; by Susan G. Arbuck and Barbara Blaylock in the book "TAXOL® Science and Applications" edited by Mathew Suffness, 1995, CRC Press Inc., Boca Raton, Fla., 379–416; and also in the references cited therein.

A semi-synthetic analog of paclitaxel named Taxotere® (docetaxel) has also been found to have good antitumor activity. The structures of paclitaxel and Taxotere® are shown below along with the conventional numbering system for molecules belonging to the class; such numbering system is also employed in this application.

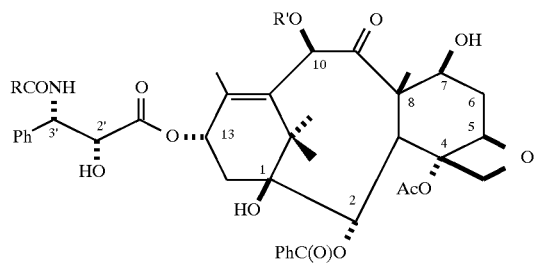

Taxol®: R=Ph; R'=acetyl
Taxotere®: R=t-butoxy; R'=hydrogen

SUMMARY OF THE INVENTION

This invention relates to novel antitumor compounds represented by formula I, or pharmaceutically acceptable salts thereof

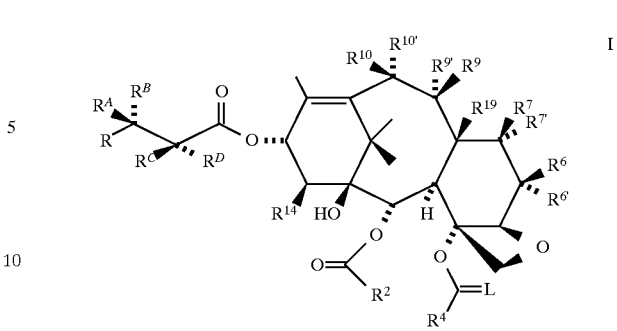

wherein R is hydrogen, $C_{1-6}$ alkyl, $C_{2-6}$ alkenyl, $C_{2-6}$ alkynyl, $C_{3-6}$ cycloalkyl, $C_{3-6}$ cycloalkenyl, cyclic 3–7 membered ring containing either one or two heteroatoms, heteroaryl or $-Z^1-R^3$;

$Z^1$ is a direct bond, $C_{1-6}$ alkyl, or $-O-C_{1-6}$ alkyl;

$R^3$ is aryl, substituted aryl, $C_{3-6}$ cycloalkyl, $C_{3-6}$ cycloalkenyl, cyclic 3–7 membered ring containing either one or two heteroatoms, or heteroaryl;

$R^A$ and $R^B$ are independently hydrogen, $-NHC(O)R$, $-NHC(O)OR$, $-NHC(O)NHR$, $-NHC(O)N(R)_2$, $-NHS(O)_mR$, $-NHP(=O)(OR)_2$, $-NHP=S(OR)_2$, where m is 1 or 2;

$R^C$ and $R^D$ are independently hydrogen, hydroxy, fluoro, $-OC(O)R^x$, $-OC(O)OR^x$, $OP(O)(OH)_2$, $OCH_2OP(O)(OH)_2$, $-OCH_2OCH_2OP(=O)(OH)_2$, $-(OCH_2)_nOC=OCH_2NHR^x$, $-(OCH_2)_nOC(=O)CH_2NR'_6R'_7$ where n is 0–3, $-OCOCH_2CH_2NH_3^+HCOO^-$, $-OCOCH_2CH_2COOH$, $-OCO(CH_2)_3COOH$, $-OC(O)(CH_2)_nNR^FR^G$, where n is 0–3, $-OC(O)CH(R'')NH_2$, $-OC(O)CH_2CH_2C(O)OCH_2CH_2OH$ or $-OC(O)-Z-C(O)-R'$;

Z is ethylene ($-CH_2CH_2-$), propylene ($-CH_2CH_2CH_2-$), $-CH=CH-$, 1,2-cyclohexane or 1,2-phenylene; R' is $-OH$, $-OH$ base, $-NR'_2R'_3$, $-OR'_3$, $-SR'_3$, $-OCH_2C(O)NR'_4R'_5$;

$R'_2$ is $-H$ or $-CH_3$;

$R'_3$ is $-(CH_2)NR'_6R'_7$ or $(CH_2)_nN+R'_6R'_7R'_8X^-$, where n is 1–3;

$R'_4$ is $-H$ or $-C_1-C_4$ alkyl;

$R'_5$ is $-H$, $-C_1-C_4$ alkyl, benzyl, hydroxyethyl, $-CH_2CO_2H$ or dimethylaminoethyl;

$R'_6$ and $R'_7$ are independently $-H$, $-CH_3$, $-CH_2CH_3$, benzyl or $R'_6$ and $R'_7$ together with the nitrogen of $NR'_6R'_7$ form a pyrrolidino, piperidino, morpholino, or N-methylpiperizino group;

$R'_8$ is $-CH_3$, $-CH_2CH_3$ or benzyl;

$X^-$ is halide;

base is $NH_3$, $(HOC_2H_4)_3N$, $N(CH_3)_3$, $CH_3N(C_2H_4)_2NH$, $NH_2(CH_2)_6NH_2$, N-methylglucamine, NaOH or KOH;

$R^F$ and $R^G$ are independently $-H$ or $-C_1-C_3$ alkyl, or $R^F$ and $R^G$ taken together with the nitrogen of $NR^FR^G$ form a pyrrolidino, piperidino, morpholino or N-methylpiperizino groups;

R'' is $-H$, $-CH_3$, $-CH_2CH(CH_3)_2$, $-CH(CH_3)CH_2CH_3$, $-CH(CH_3)_2$, $-CH_2$phenyl, $-(CH_2)_3NH_2$, $-(CH_2)_4NH_2$, $-CH_2CH_2COOH$, $-(CH_2)_3NHC(=NH)NH_2$, the residue of the amino acid proline, $-OC(O)CH=CH_2$, $-C(O)CH_2CH_2C(O)NHCH_2CH_2SO_3-Y+$ or $-OC(O)CH_2CH_2C(O)NHCH_2CH_2CH_2SO_3-Y+$;

Y+ is Na+ or N+(Bu)$_4$;

$R^2$ is $R^x$, $R^y$ or $R^{y'}$;

$R^4$ is $C_{1-6}$ alkyl, $C_{2-6}$ alkenyl, $C_{2-6}$ alkynyl, $C_{3-6}$ cyclo alkyl, $C_{3-6}$ cycloalkenyl, $C_{3-6}$ heteroaryl, $-O-C_{1-6}$ alkyl, $-O-C_{2-6}$ alkenyl, $-O-C_{2-6}$ alkynyl, $-CH_2OC H_3$, —CH$_2$OCH$_2$OCH$_3$, —CH$_2$OCH$_2$OCH$_2$CH$_3$, —CH$_2$CH$_2$OCH$_3$, —CHOCH$_2$ (an oxirane), or —S—C$_{1-6}$ alkyl;

L is O or S;

R$^6$ and R$^{6'}$ are independently hydrogen, hydroxy, —O—C$_{1-6}$ alkyl, —OC(O)R$^x$, —OC(O)OR$^x$, —OC(O)NHR$^x$, —OC(O)NR$_6$R'$_7$, —OCH$_2$OR, —OC(R$^x$)$_2$OR, —OCHR$^x$OR, —OCH$_2$SCH$_3$, —OCH$_2$OCH$_2$SCH$_3$, OP(O)(OH)$_2$, OCH$_2$OP(O)(OH)$_2$, —OCH$_2$OCH$_2$OP(O)(OH)$_2$, —(OCH$_2$)$_n$OC=OCH$_2$NHR$^x$, —(OCH$_2$)$_n$OC(=O)CH$_2$NR'$_6$R'$_7$, where n is 0–3, —C$_{1-6}$ alkyl, —CH$_2$OR, —CH$_2$SCH$_3$, —CH$_2$OCH$_2$SCH$_3$, —OC(R$^x$)$_2$SR, —OCHR$^x$SR, —OCOCH$_2$CH$_2$NH$_3^+$ HCOO$^-$, —OCOCH$_2$CH$_2$COOH, —OCO(CH$_2$)$_3$COOH, —OC(O)(CH$_2$)$_n$NR$^F$R$^G$, where n is 0–3, —OC(O)—Z—C(O)—R' or —OC(O)CH$_2$CH$_2$C(O)OCH$_2$CH$_2$OH, provided that both R$^6$ and R$^{6'}$ cannot be hydrogen, R$^6$ and R$^{6'}$ together can form an oxo group or a thiocarbonyl group, or R$^6$ and R$^{6'}$ together can form a carbon nitrogen double bond of formula —C=N—R, —C=N—OR or —C=N—NHR —C=N—NR'$_6$R'$_7$, where R is as previously defined, provided it is not hydrogen;

R$^{7'}$ is hydrogen; R$^7$ is hydrogen or when taken together with R$^{19}$ can form a cyclopropane ring;

R$^9$ and R$^{9'}$ are independently hydrogen, hydroxy, or together form an oxo (keto) group;

R$^{10}$ and R$^{10'}$ are independently hydrogen, hydroxy, —OC(O)R$^x$, —OC(O)OR$^x$, —O—C$_{1-6}$ alkyl, —OCH$_2$OCH$_3$, —OCH$_2$OCH$_2$OCH$_3$, —OCH$_2$OCH$_2$OCH$_2$CH$_3$, —OCH$_2$OCH$_2$CH$_2$OCH$_3$, —OCH$_2$OCH$_2$CH$_2$OH, —OCH$_2$SCH$_3$, —OCH$_2$OCH$_2$SCH$_3$, —OC(O)N'$_{6R'7}$, C$_{1-6}$ alkyl, —(CH$_2$)$_3$C(O)R$^x$, —(CH$_2$)$_3$C(O)OR$^x$, —(CH$_2$)$_3$CN, —OP(O)(OH)$_2$, —OCH$_2$OP(O)(OH)$_2$, —OCH$_2$OCH$_2$OP(O)(OH)$_2$, —(OCH$_2$)$_n$OC=OCH$_2$NHR$^x$, —(OCH$_2$)$_n$OC(=O)CH$_2$NR'$_6$R'$_7$, where n is 0–3, —OCOCH$_2$CH$_2$NH$_3^+$ HCOO, —OCOCH$_2$CH$_2$COOH, —OCO(CH$_2$)$_3$COOH, —OC(O)—Z—C(O)—R', —OC(O)(CH$_2$)$_n$NR$^F$R$^G$ where n is 0–3, or —OC(O)CH$_2$CH$_2$C(O)OCH$_2$CH$_2$OH;

R$^{14}$ is hydrogen, hydroxy, —(O)R$^x$, —OC(O)OR$^x$, —O—C$_{1-6}$ alkyl, —OCH$_2$OCH$_3$, —H$_2$OCH$_2$OCH$_3$, —OCH$_2$OCH$_2$OCH$_2$CH$_3$, —OCH$_2$OCH$_2$CH$_2$OCH$_3$, —OCH$_2$OCH$_2$CH$_2$OH, —OCH$_2$SCH$_3$, —OCH$_2$OCH$_2$SCH$_3$, OP(O)(OH)$_2$, OCH$_2$OP(O)(OH)$_2$, —OCH$_2$OCH$_2$OP(O)(OH)$_2$, —(OCH$_2$)$_n$O(C=O)CH$_2$NHR$^x$ or —(OCH$_2$)$_n$OC(=O)CH$_2$NR'$_6$R'$_7$ where n is 0–3;

R$^{19}$ is methyl, hydroxymethyl, or R$^{19}$ and R$^7$ together can form a cyclopropane ring with the proviso that when these substituents are cyclopropane ring then R$^{7'}$ is hydrogen;

R$^x$ is C$_{1-6}$ alkyl, C$_{2-6}$ alkenyl, C$_{2-6}$ alkynyl, C$_{3-6}$ cyclo alkyl, any of which groups can be optionally substituted with one to six of the same or different halogen atoms;

R$^y$ is a radical of the formula

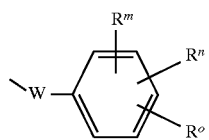

wherein W is a bond and R$^m$, R$^n$, and R$^o$ are independently hydrogen, nitro, cyano, azido, amino, C$_{1-6}$ alkylamino, di-C1-6 alkylamino, halogen, C$_{1-6}$ alkyl, hydroxy or C$_{1-6}$ alkoxy; and R$^{y'}$ is a radical of the formula

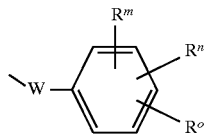

wherein W is C$_{1-6}$ alkyl or —OC1-6 alkyl, and R$^m$, R$^n$, and R$^o$ are independently hydrogen, nitro, cyano, azido, amino, C$_{1-6}$ alkylamino, di-C1-6 alkylamino, halogen, C$_{1-6}$ alkyl, hydroxy or C$_{1-6}$ alkoxy.

Another aspect of the present invention provides a method for inhibiting tumor in a mammalian host which comprises administering to said mammalian host an antitumor effective amount of a compound of formula I.

Yet, another aspect of the present invention provides a pharmaceutical formulation which comprises an antitumor effective amount of a compound of formula I in combination with one or more pharmaceutically acceptable carriers, excipients, diluents or adjuvants.

DETAILED DESCRIPTION

In the application, unless otherwise specified explicitly or in context, the following definitions apply. The numbers in the subscript after the symbol "C" define the number of carbon atoms a particular group can contain. For example "C$_{1-6}$ alkyl" means a straight or branched saturated carbon chain having from one to six carbon atoms; examples include methyl, ethyl, n-propyl, isopropyl, n-butyl, sec-butyl, isobutyl, t-butyl, n-pentyl, sec-pentyl, isopentyl, and n-hexyl. Depending on the context, "C$_{1-6}$ alkyl" can also refer to C$_{1-6}$ alkylene which bridges two groups; examples include propane-1,3-diyl, butane-1,4diyl, 2-methyl-butane-1,4diyl, etc. "C$_{2-6}$ alkenyl" means a straight or branched carbon chain having at least one carbon-carbon double bond, and having from two to six carbon atoms; examples include ethenyl, propenyl, isopropenyl, butenyl, isobutenyl, pentenyl, and hexenyl. Depending on the context, "C$_{2-6}$ alkenyl" can also refer to C$_{2-6}$ alkenediyl which bridges two groups; examples include ethylene-1,2-diyl (vinylene), 2-methyl-2-butene-1,4-diyl, 2-hexene-1,6-diyl, etc. "C$_{2-6}$ alkynyl" means a straight or branched carbon chain having at least one carbon-carbon triple bond, and from two to six carbon atoms; examples include ethynyl, propynyl, butynyl, and hexynyl.

"Aryl" means aromatic hydrocarbon having from six to ten carbon atoms; examples include phenyl and naphthyl. "Substituted aryl" means aryl independently substituted with one to five (but preferably one to three) groups selected from C$_{1-6}$ alkanoyloxy, hydroxy, halogen, C$_{1-6}$ alkyl, trifluoromethyl, C$_{1-6}$ alkoxy, aryl, C$_{2-6}$ alkenyl, C$_{1-6}$ alkanoyl, nitro, amino, cyano, azido, C$_{1-6}$ alkylamino, di-C$_{1-6}$ alkylamino, and amido. "Halogen" means fluorine, chlorine, bromine, and iodine.

"Heteroaryl" means a five- or six-membered aromatic ring containing at least one and up to four non-carbon atoms selected from oxygen, sulfur and nitrogen. Examples of heteroaryl include thienyl, furyl, pyrrolyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, triazinyl, tetrazinyl, and like rings.

"Hydroxy protecting groups" include, but is not limited to, ethers such as methyl, t-butyl, benzyl, p-methoxybenzyl, p-nitrobenzyl, allyl, trityl, methoxymethyl, methoxyethoxymethyl, ethoxyethyl, tetrahydropyranyl, tetrahydrothiopyranyl, dialkylsilylethers, such as dimethylsilyl ether, and trialkylsilyl ethers such as trimethylsilyl ether, triethylsilyl ether, and t-butyldimethylsilyl ether; esters such as benzoyl, acetyl, phenylacetyl, formyl, mono-, di-, and trihaloacetyl such as chloroacetyl, dichloroacetyl, trichloroacetyl, trifluoroacetyl; and carbonates such as methyl, ethyl, 2,2,2-trichloroethyl, allyl, benzyl, and p-nitrophenyl. Additional examples of hydroxy protecting groups may be found in standard reference works such as Greene and Wuts, *Protective Groups in Organic Synthesis* 2d Ed., 1991, John Wiley & Sons, and McOmie; and *Protective Groups in Organic Chemisty*, 1975, Plenum Press.

"Ph" means phenyl; "ipr" means isopropyl; "DAST" means diethylainino sulfur trifluoride.

The substituents of the substituted alkyl, alkenyl, alkynyl, aryl, and heteroaryl groups and moieties described herein, may be alkyl, alkenyl, alkynyl, aryl, heteroaryl and/or may contain nitrogen, oxygen, sulfur, halogens and include, for example, lower alkoxy such as methoxy, ethoxy, butoxy, halogen such as chloro or fluoro, nitro, amino, and keto.

The term "taxane" or "taxane core" refers to moieties with a framework of the structure:

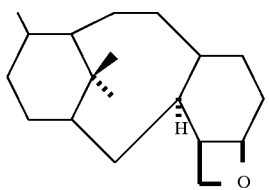

The cyclopropane group which can be constituted from $R^7$ and $R^{19}$ of formula I can alternatively be referred to as "7β,8β-methano" group as in *Tetrahedron Letters* 1994, Vol 35, No 43, pp 7893–7896, 1994 or as "cyclopropa" group as in U.S. Pat. No. 5,254,580 issued Oct. 19, 1993.

A preferred embodiment are compounds with the structure II, or pharmaceutically acceptable salts thereof, having the following groups:
$R^A$=-hydrogen, $R^C$=-hydrogen, $R^9$=$R^{9'}$=oxo (ketone), L=oxygen, $R^{10'}$=—H, $R^{14}$=—H, $R^7$=$R^{7'}$=—H.

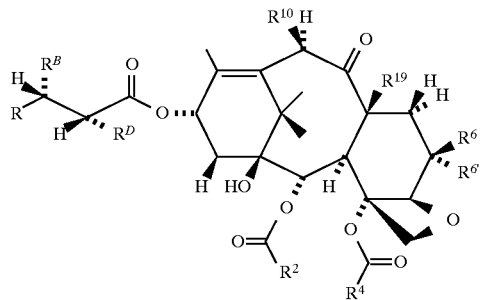

II

R includes 2-furanyl (2-furyl), 2-thienyl, 3-furanyl (3-furyl), 3-thienyl, phenyl, napthyl, 4-hydroxyphenyl, 4-methoxyphenyl, 4-fluorophenyl, 4-trifluoromethylphenyl, 2-propynyl, benzyl, phenethyl, phenylethenyl, 3,4-dimethoxyphenyl, 2-(2-furanyl)ethenyl, 2-methylpropyl, $C_{3-6}$ cycloalkyl, cyclohexylmethyl, cyclohexylethyl and the like.

R also includes $C_{3-6}$ alkyl including n-propyl, n-butyl, sec-butyl, isopropyl, 2-methyl-propyl, isobutyl, $C_{3-6}$ alkenyl including 1-(1-propenyl), 1-(2-propenyl),2-propenyl, 2-(1-butenyl), 1-(2-butenyl), 1-(3-butenyl), 2-(1-butenyl), 2-(2-butenyl), 2-(3-butenyl), and 1-(2-methyl-1-propenyl) (isobutenyl), t-butyl, or —$Z^1$—$R^3$; $Z^1$ is a direct bond, $R^3$ is aryl including phenyl, substituted aryl including p fluoro phenyl and p-methyl phenyl, $C_{3-6}$ cycloalkyl including cyclopropyl, cyclobutyl, cyclopentyl, and cyclohexyl, $C_{3-6}$ cycloalkenyl, cyclic 3–7 membered ring containing either one or two heteroatoms, or heteroaryl such as 2-furyl, 3-furyl, 2-thienyl, or 3-thienyl.

$R^B$ includes —NHC(O)Ph (or substituted phenyl) —NHC(O)O($C_{1-6}$ alkyl), most preferably —NHC(O)OtBu, —NHC(O)OnBu, —NHC(O)OiPr, —NHC(O)OCH$_2$Ph, NHC(O)-heterocycle, including —NHC(O)-2-furyl, —NHC(O)NHR, —NHC(O)N(R)$_2$;

$R^D$ includes hydroxy, OP(O)(OH)$_2$, OCH$_2$OP(O)(OH)$_2$, —OCH$_2$OCH$_2$OP(O)(OH)$_2$, —(OCH$_2$)$_m$OC=OCH$_2$NHR$^x$, —(OCH$_2$)$_m$OC(=O)CH$_2$NR'$_6$R'$_7$, where m is 0–3, —OC(O)CH$_3$, —OC(O)OCH$_2$C(Cl)$_3$, —OCOCH$_2$CH$_2$NH$_3^+$ HCOO$^-$, NHC(O)phenyl, —NHC(O)OC(CH$_3$)$_3$, —OCOCH$_2$CH$_2$COOH, —OCO(CH$_2$)COOH, —OC(O)—Z—C(O)—R', —OC(O)(CH$_2$)$_n$NR$^F$R$^G$, where n is 0–3, or —OC(O)CH$_2$CH$_2$C(O)OCH$_2$CH$_2$OH;

$R^2$ includes -phenyl or substituted phenyl (preferably mono- or di-substitution);

$R^4$ includes most preferably methyl, but could be, $C_{1-4}$ alkyl, $C_{3-5}$ cyclo alkyl, —O—$C_{1-4}$ alkyl, —CH$_2$OCH$_3$, CHOCH$_2$, (oxirane), or —S—$C_{1-4}$ alkyl;

$R^6$ and $R^{6'}$ are independently hydrogen, hydroxy, —O—$C_{1-6}$ alkyl, —OC(O)R$^x$, —OC(O)OR$^x$, —OC(O)NHR$^x$, —OC(O)NR$_2$, —OCH$_2$OR, most preferably —OCH$_2$OCH$_3$, —OCH$_2$OCH$_2$OCH$_3$, —OCH$_2$OCH$_2$OCH$_2$CH$_3$, —OCH$_2$OCH$_2$CH$_2$OCH$_3$, or —OCH$_2$OCH$_2$CH$_2$OH, —OC(R$^x$)$_2$OR, —OCHR$^x$OR, —OCH$_2$SR most preferably —OCH$_2$SCH$_3$ or —OCH$_2$OCH$_2$SCH$_3$, —OC(R$^x$)$_2$SR, —OCHR$^x$SR, OP(O)(OH)$_2$, OCH$_2$OP(O)(OH)$_2$, —OCH$_2$OCH$_2$OP(O)(OH)$_2$, —(OCH$_2$)$_n$OC=OCH$_2$NHR$^x$, —(OCH$_2$)$_n$OC(=O)CH$_2$NR'$_6$R'$_7$, where n is 0–3, —$C_{1-6}$ alkyl, —CH$_2$OR, most preferably —CH$_2$OCH$_3$, —CH$_2$OCH$_2$OCH$_3$, —CH$_2$OCH$_2$OCH$_2$CH$_3$, —CH$_2$OCH$_2$CH$_2$OCH$_3$ or —CH$_2$OCH$_2$CH$_2$OH, or —CH$_2$SR most preferably —CH$_2$SCH$_3$, —CH$_2$OCH$_2$SCH$_3$, provided both $R^6$ and R6' cannot be hydrogen, or $R^6$ and $R^{6'}$ together form an oxo group, or $R^6$ and $R^{6'}$ together form a carbon nitrogen double bond of formula C=N—R or —C=N—OR;

$R^{10}$ is hydrogen, hydroxy, —OC(O)R$^x$, —OC(O)OR$^x$, —O—$C_{1-6}$ alkyl, —OCH$_2$OCH$_3$, —OCH$_2$OCH$_2$OCH$_3$, —OCH$_2$OCH$_2$OCH$_2$CH$_3$, —OCH$_2$OCH$_2$CH$_2$OCH$_3$, —OCH$_2$OCH$_2$CH$_2$OH, —OCH$_2$SCH$_3$, —OCH$_2$OCH$_2$SCH$_3$, —OC(O)NR$^8$R$^9$, $C_{1-6}$alkyl, —(CH$_2$)$_3$C(O)R$^x$, —(CH$_2$)$_3$C(O)OR$^x$, or —(CH$_2$)$_3$CN; most preferably $R^{10}$ is hydrogen, hydroxy, or —OC(O)CH$_3$; and $R^{19}$ is —CH$_3$, or $R^{19}$ and $R^7$ together can form a cyclopropane ring with the proviso that when these substituents are a cydopropane ring, then $R^{7'}$ is hydrogen.

Another preferred embodiment are compounds with the structure III, or pharmaceutically acceptable salts thereof, having the following groups:
$R^A$=-hydrogen, $R^C$=-hydrogen, $R^2$=-phenyl, $R^4$=methyl, $R^7$=$R^{7'}$=—H, $R^9$=$R^{9'}$=oxo (ketone), L=oxygen, $R^{10'}$=—H, $R^{14}$=—H, $R^{19}$=—CH$_3$, This depiction will be used to describe the specific experimental procedures of the invention but in no way implies that the other compounds encompassed by the invention are not amenable to the procedures detailed herein. The structures I=II=III except that some of the variables in I are assigned as above to produce Im. The structures are intended to be derivatives of the generic structure I in which the substituents above have been assigned for clarity in the examples. Concise methods for synthesizing other generic compounds of Structure I not encompassed by simplified formula ImI are described in the text and are well known in the art.

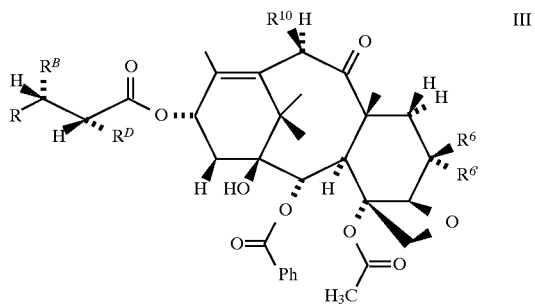

R includes 2-furanyl (2-furyl), 2-thienyl, 3-furanyl (3-furyl), 3-thienyl, phenyl, napthyl, 4-hydroxyphenyl, 4-methoxyphenyl, 4-fluorophenyl, 4-trifluoromethylphenyl, 2-propynyl, benzyl, phenethyl, phenylethenyl, 3,4-dimethoxyphenyl, 2-(2-furanyl) ethenyl, 2-methylpropyl, cyclopropyl, cyclobutyl, cyclopentyl, cyclohexyl, cyclohexylmethyl, cyclohexylethyl and the like.

R also includes $C_{3-6}$ alkyl including n propyl, n-butyl, sec-butyl, isopropyl, 2-methyl-propyl, isobutyl, $C_{3-6}$ alkenyl including 1-(1-propenyl), 1-(2-propenyl),2-propenyl, 2-(1-butenyl), 1-(2-butenyl), 1-(3-butenyl), 2-(1-butenyl), 2-(2-butenyl), 2-(3-butenyl), and 1-(2-methyl-1-propenyl) (isobutenyl), t-butyl, or $-Z^1-R^3$; $Z^1$ is a direct bond, $R^3$ is aryl including phenyl, substituted aryl including p fluoro phenyl and p-methyl phenyl, $C_{3-6}$ cycloalkyl including cyclopropyl, cyclobutyl, cyclopentyl, and cyclohexyl, $C_{3-6}$ cycloalkenyl, cyclic 3–7 membered ring containig either one or two heteroatoms, or heteroaryl such as 2-furyl, 3-furyl, 2-thienyl, or 3-thienyl.

$R^B$ includes —NHC(O)Ph (or substituted phenyl), —NHC(O)O($C_{1-6}$ alkyl), most preferably —NHC(O)OtBu, —NHC(O)OnBu, —NHC(O)OiPr, —NHC(O)OCH$_2$Ph, NHC(O)—heterocycle, including —NHC(O)-2-furyl, —NHC(O)NHR, —NHC(O)N(R)$_2$;

$R^D$ includes hydroxy, OP(O)(OH)$_2$, OCH$_2$OP(O)(OH)$_2$, —OCH$_2$OCH$_2$OP(O)(OH)$_2$, —(OCH$_2$)$_m$OC=OCH$_2$NHR$^x$, —(OCH$_2$)$_m$OC(=O)CH$_2$NR'$_6$R'$_7$, where m is 0–3, —OC(O)CH$_3$, —OC(O)OCH$_2$C(Cl)$_3$, —OCOCH$_2$CH$_2$NH$_3^+$ HCOO$^-$, —NHC(O)phenyl, —NHC(O)OC(CH$_3$)$_3$, —OCOCH$_2$CH$_2$COOH, —OCO(CH$_2$)$_3$COOH, —OC(O)—Z—C(O)—R', —OC(O)(CH$_2$)$_n$NR$^F$R$^G$, where n is 0–3, or —OC(O)CH$_2$CH$_2$C(O)OCH$_2$CH$_2$OH;

$R^6$ and $R^{6'}$ are independently hydrogen, hydroxy, —O—$C_{1-6}$ alkyl, —OC(O)R$^x$, —OC(O)OR$^x$, —OC(O)NHR$^x$, —OC(O)NR$_2$, —OCH$_2$OR most preferably —OCH$_2$OCH$_3$, —OCH$_2$OCH$_2$OCH$_3$, —OCH$_2$OCH$_2$OCH$_2$CH$_3$, —OCH$_2$OCH$_2$CH$_2$OCH$_3$, —OCH$_2$OCH$_2$CH$_2$OH, —OC(R$^x$)$_2$OR, —OCHR$^x$OR, —OCH$_2$SR, most preferably —OCH$_2$SCH$_3$, or —OCH$_2$OCH$_2$SCH$_3$, —OC(R$^x$)$_2$SR, —OCHR$^x$SR, OP(O)(OH)$_2$, OCH$_2$OP(O)(OH)$_2$, —OCH$_2$OCH$_2$OP(O)(OH)$_2$, —(OCH$_2$)$_n$OC=OCH$_2$NHR$^x$, —(OCH$_2$)$_n$OC(=O)CH$_2$NR'$_6$R'$_7$, where n is 0–3, —$C_{1-6}$ alkyl, —CH$_2$OR, most preferably —CH$_2$OCH$_3$, —CH$_2$OCH$_2$OCH$_3$, —CH$_2$OCH$_2$OCH$_2$CH$_3$, —CH$_2$OCH$_2$CH$_2$OCH$_3$ or —CH$_2$OCH$_2$CH$_2$OH or —CH$_2$SR most preferably —CH$_2$SCH$_3$, —CH$_2$OCH$_2$SCH$_3$, provided both R$^6$ and R6' cannot be hydrogen; most preferably one of the substituents R$^6$ and R6' are hydrogen and the other as described above; or R$^6$ and R$^{6'}$ together form an oxo group; or R$^6$ and R$^{6'}$ together form a carbon nitrogen double bond of formula C=N—R or —C=N—OR; and $R^{10}$ is hydrogen, hydroxy, —OC(O)R$^x$, —OC(O)OR$^x$, —O—$C_{1-6}$ alkyl, —OCH$_2$OCH$_3$, —OCH$_2$OCH$_2$OCH$_3$, —OCH$_2$OCH$_2$OCH$_2$CH$_3$, —OCH$_2$OCH$_2$CH$_2$OCH$_3$, —OCH$_2$OCH$_2$CH$_2$OH, —OCH$_2$SCH$_3$, —OCH$_2$OCH$_2$SCH$_3$ or —(O)NR$_6$R'$_7$.

Most preferably $R^{10}$ is hydrogen, hydroxy, or —OC(O)CH$_3$.

The new products that have the general formula I, II, and III display a significant inhibitory effect with regard to abnormal cell proliferation, and have therapeutic properties that make it possible to treat patients who have pathological conditions associated with an abnormal cell proliferation. The pathological conditions include the abnormal cellular proliferation of malignant or non-malignant cells in various tissues and/or organs, including, non-limitatively, muscle, bone and/or conjunctive tissues; the skin, brain, lungs and sexual organs; the lymphatic and/or renal system; mammary cells and/or blood cells; the liver, digestive system, and pancreas; and the thyroid and/or adrenal glands. These pathological conditions can also include psoriasis; solid tumors; ovarian, breast, brain, prostate, colon, stomach, kidney, and/or testicular cancer, Karposi's sarcoma; cholangiocarcinoma; choriocarcinoma; neuroblastoma; Wilm's tumor, Hodgkin's disease; melanomas; multiple myelomas; chronic lymphocytic leukemias; and acute or chronic granulocytic lymphomas. The novel products in accordance with the invention are particularly useful in the treatment of non-Hodgkin's lymphoma, multiple myeloma, melanoma, and ovarian, urothelial, oesophageal, lung, and breast cancers. The products in accordance with the invention can be utilized to prevent or delay the appearance or reappearance, or to treat these pathological conditions. In addition, the compounds of formula I are useful in treating and/or preventing polycystic kidney diseases (PKD) and rheumatoid arthritis.

The compounds of this invention can be made by techniques from the conventional organic chemistry repertoire. Schemes I–XII, which depict processes that compounds within the scope of formula I can be made, are only shown for the purpose of illustration and are not to be construed as limiting the processes to make the compounds by any other methods.

The following procedures describe methods which can be utilized to prepare taxane analogs which contain substituents at C-6 and which are deoxygenated at C-7 and which have surprisingly unexpected anticancer properties, in light of the fact that the 6-α-hydroxy analog of paclitaxel (which has a hydroxy group at C-7) is a known human metabolite of paclitaxel which has been found to be much less cytotoxic than the parent compound and therefore is likely to be much less efficacious J. W. Harris et. al. *J. Med. Chem.* 1994, 37, 706–709; A. Rahlnan et. al. *Cancer Research* 1994, 54, 5543–5546; G. Kumar et. al. *Cancer. Chemother. Pharmcol.* 1995, 36, 129–135.

The synthesis and unexpected enhanced properties of taxane analogs with an alcohol at C-6 in the β-configuration has never before been disclosed.

The compounds I of this invention are 7-deoxy-6-oxygenated or 6-substituted taxane analogs. All of the contemplated analogs can be prepared from a previously reported 6α,7α-diol intermediate 4 (Scheme I) or suitably substituted analogs. The preparation of this diol intermediate is shown in Scheme I.

As shown in Scheme I, the starting material is a taxane analog suitably protected to leave the most reactive hydroxy group at C-7. Compound 1 in Scheme I is protected at the 2' hydroxy group at the sidechain. The two examples of compound 1 actually described utilize silyl protecting groups at the 2' position, but other protecting groups could be utilized. The preparation of intermediates 1 are now well known in the art. The synthesis of diols 4 utilizes precursor 6,7-olefin analogs 3 which are also now known in the art. The compound's 3 can be formed directly from intermediate's 1 upon treatment with a reagent such as DAST as described in the U.S. Pat. No. 5,380,751. The synthesis of olefin 3 described in Scheme I proceeds through the 7-trifluoromethanesulfonate (triflate) intermediates 2 which are prepared as shown in step A. Elimination of the triflate (step B) provides the desired olefins 3. The preparation of 7-O triflates and their conversion into cyclopropanes and olefins has been divulged by Johnson, R. A., et al., *Taxol chemistry*. 7-O-Triflates as precursors to olefins and cyclopropanes. Tetrahedron Letters, 1994.35(43): p. 7893–7896 & by the same authors in WO 94/29288.

The olefin 3 is then hydroxylated with Osmium tetroxide (step C) which is used in either stoichiometric quantifies or catalytically in the presence of a cooxidant such as N-methyl morpholine-N oxide (NMO). A patent application on such diol intermediates which includes some methods of its preparation has been published: Roth et. al. 6,7 EP 0 600 517 A1. A protected taxane diol intermediate has also been described in the literature by Liang et. al. *Tetrahedron Letters* 1995, 36(17) 2901–2904. and ibid. 1995,36(43) 7795–7798. The osmium reagent only reacts from the face of the double bond which is down or α as the taxane core is depicted in this document. Thus this reaction provides only one stereoisomer.

The preferred approach to the initial 7-deoxy-substituted taxanes is shown in Scheme II. An advantage of this approach is it avoids the need for a selective protection of the starting 6,7 diol 4. A new cyclic thiocarbonate 5 is formed (step D)upon reaction with thiocarbonyldiimidazole (or alternatively thiophosgene could be used) under standard conditions of amine base and optional inert solvent. Other standard organic chemistry bases could also be utilized. Reduction of the thiocarbonate 5 (step E) with most preferably, a trialkyl germane such as tri-n-butyl germane provides the C-7 deoxy compound 6 with little, if any, competitive formation of the C-6 deoxy material. Alternatively, a trialkyl tin hydride could be utilized in place of the germanium reagent. The use of the tin hydride reagent also results in competitive deoxygenation at C-10 which produces mixtures which must be separated. The tin reagent is the method of choice for producing C 7 and 10 deoxy -6-substituted analogs if these are the desired targets. The use of trialkyl germane to suppress an unwanted side reaction is not precedented. This reagent has been studied by physical chemists in other radical reactions. J. W. Wilt et.al. *J. Am. Chem. Soc.* 1988, 110, 281–287. The product of step E is a 7-deoxy-6α-hydroxy intermediate 6 which is protected at the sidechain. As shown in Scheme II, deprotection (step F) of the sidechain by standard methods, which are by now well known in the art provides compounds III ($R^D$=—OH, $R^6$=—H, $R^{6'}$=—OH) which are compounds with useful antitumor properties and which are claimed in this invention. The above reactions are demonstrated in Example 1.

An alternative route for synthesizing these same compounds are shown in Scheme III. This strategy for deoxygenating C-7 involves selectively protecting the C-6 hydroxy group of diol 4 (which is down or alpha) using common silyl, ester, or carbonate protecting groups as described in Greene et. al. The most preferred protecting groups are trialkylsilyl esters, acetate, phenoxy acetate, trichoroethylchloroformate, or benzoate. Examples of selectively protected compounds have appeared in the literature X. Liang, D. G. Kingston *Tetrahedron Letters* 1995, 36, 2901–2904. The examples of step G in this patent describe the use of trialkyl silyl protecting groups to provide compounds 7. Formation of a methyl xanthate at C-7 under standard conditions (step H) provides compounds 8. Reaction of compound 8 with trialkyl or aryl stannanes such as tri-n-butyl tin hydride in inert solvents at elevated temperatures which are sufficient for the reaction (usually 700° to 110° C.) provides mixtures of compounds 9 and 10. Sometimes the reaction is carried out in the presence of a radical initiator such as AIBN. The ratio of products is somewhat dependent on reaction conditions since excess tin reagent and higher reaction temperatures favor the formation of the C-10 deoxygenation reaction and thus compound 10. Use of tri-n-butylgermane should suppress the C-10 deoxygenation reaction. Compounds 9 and 10 can be separated chromatographically after deprotection (step J) using either aqueous acid or fluoride sources. The above reactions are demonstrated in Example 1.

Deoxygenation of taxanes at both C-7 and C-10 have been previously reported using similar methodology. Synthetic methodology for the preparation of C-7 deoxygenated Taxanes and their activity has been described in the literature: Chen, S.-H. and V. Farina, Paclitaxel structure-activity relationships and core skeletal rearrangements. ACS Symp. Ser., 1995. 583(Taxane Anticancer Agents): p. 247–61; Chen, S.-H., et al., A Facile Synthesis of 7,10-Dideoxy Taxol and 7-Epi-10-Deoxy Taxol. Tetrahedron Letters, 1993. 34(43): p. 6845–6848; Chen, S.-H., et al., Synthesis of 7-Deoxy- and 7,10-Dideoxytaxol via Radical Intermediates. J. Org. Chem., 1993. 58: p. 5028–5029; Chen, S. H., et al., Taxol(R) Structure-Activity-Relationships—Synthesis And Biological Evaluation Of Taxol Analogs Modified At C-7. Bioorganic & Medicinal Chemistry Letters, 1994. 4: p. 2223–2228; Kingston, D. G. I., A. G. Chaudhary, and J. M. Rimoldi, Modified Taxols. 10. Preparation of 7-Deoxytaxol, a Highly Bioactive Taxol Derivative, and Interconversion of Taxol and 7-epi-Taxol. J. Org. Chem., 1993. 58(15): p. 3798–3799. Chaudhary, A. G., Kingston, D. G. I., Synthesis of 10-deacetoxy taxol and 10-deoxytaxotere, Tetrahedron Letters, 1993, 34(31), 4921–4924.

All of these compounds have hydrogen substituents at C-6.

In the patent literature, U.S. Pat. No. 5,478,854 granted Dec. 26, 1995, Upjohn (WO94/13655), and Holton et. al. (WO94/17050 published Aug. 4,1994) have disclosed C-7 deoxygenated compounds. In patent application WO94/ 17050, Holton claims many substituents at the taxane C-6 position (and the numerous other positions on the whole molecule) including hydroxy and alkoxy, but has no enabling methodology for making these compounds. Both other C-7 deoxy patent publications disclose only hydrogens at the taxane C-6 position.

As shown in Scheme IV, the C-6 alcohol 6 can now be oxidized to the ketone 11 using standard oxidants common in the art. The preferred reagent is TPAP (Tetrapropylammonium perruthenate) as described by Ley in *Aldrichimica Acta* 21(1), 16(1988), and ibid., 22(2), 53 (1989) and *J. Chem. Soc. Chem. Commun.* 1625(1987). This ketone can then be desilylated under a variety of standard conditions to provide compounds III ($R^D$=—OH, $R^6$=$R^{6'}$= oxo (=O)). The above reactions are demonstrated in Example 2, 8, 10, 11.

Reduction of ketone 11 with standard reducing agents such as Sodium borohydride in ethanol under conditions where selective ketone reduction occurs in the presence of esters (or the more hindered C-9 ketone) produces the protected 6β-hydroxy-7-deoxy paclitaxel 12 (Scheme V). Hydride delivery occurrs preferentially from the bottom, less hindered α face. Desilylation of compound 12 provides 6β-hydroxy compounds III ($R^D$=—OH, $R^6$=—OH, $R^{6'}$=—H). The above reactions are demonstrated in Example 3, 9, 10, 11.

As shown in Scheme VI, addition of organometallic reagents to the ketone 11 provides mainly or exclusively tertiary alcohols at C-6 with the alcohol in the 1 configuration (up). This is a result of more facile attack from the bottom face. For example use of trimethyl aluminum provides compound 13 ($R^6$=—OH, $R^{6'}$=—CH$_3$), which is the product of methyl addition to the ketone. Other organometallic reagents such as alkyl lithium reagents, Grignard reagents, or cerium based reagents which are well known in the art would also provide some of the desired products. Desilylation provides compounds III ($R^D$=—OH, $R^6$=—OH, $R^{6'}$=—CH$_3$). The above reactions are demonstrated in Example 4.

As shown in Scheme VII of the experimental section, reductive removal of the C-13 sidechain using tetrabutylammonium borohydride via standard Taxol methodology (N. F. Magri, D. G. I. Kingston, C. Jitrangsri, T. Piccariello *J. Org. Chem.* 1986, 51, 3239–3242) from diol III ($R^D$=—OH, $R^6$=—H, $R^{6'}$=—OH) provides the a hydroxy baccatin which can be selectively protected using standard protecting groups on the 6-hydroxy group to give 15. The examples utilize trialkylsilyl ethers as the protecting group but others are suitable. Protected baccatin 15 can now be coupled with other sidechains using any methodology which is well known in the art. In these examples lactams are employed by using the standard coupling which has been described in U.S. Pat. Nos. 5,229,526 and 5,175,315 to Holton. Desilylation (or suitable deprotection conditions) provides analogs III ($R^D$=—OH, $R^6$=—H, $R^{6'}$=—OH) with alternative sidechains to produce compounds 9. The above reactions are demonstrated in Examples 5, 6, and 7.

As shown in Scheme VIII direct oxidation of the 6a-alcohol of analogs III ($R^D$=—OH, $R^6$=—H, $R^{6'}$=—OH) followed by reduction as described above in Scheme V, provides 6 B-hydroxy analogs with modified sidechains. Alternatively, as shown in Scheme IX, Bis silylated compounds 9 can be selectively deprotected at C-6 using for example acidic Dowex resin suspended in methanol(step W) to provide intermediates 6 which can be oxidized and reduced as described in Schemes IV and V. This produces compounds III ($R^D$=—OH, $R^6$=—OH, $R^{6'}$=—H) with a 6β-hydroxy substituent and modified sidechains. The above reactions are demonstrated in Examples 10 and 11.

As shown in Scheme X, step X, deprotonation of alcohols 17 with a lithium amide base (lithium bistrimethylsilylamide) followed by O-alkylation with bromomethyl methyl ether provides the 6α-methoxymethyl ether analog 17. This reaction illustrates the preparation of hydroxy derivatives at C-6 and demonstrates that conventional alcohol derivatization techniques can be utilized with C-6 alcohols. Other derivatives claimed in this application can be prepared using similar methodology. Deprotection of the 2' hydroxy protecting group under standard conditions, provides the 6-methoxymethyl ethers III ($R^D$=—OH, $R^6$=—OCH$_2$OCH$_3$, $R^{6'}$=—OH). As shown in Scheme M, a similar sequence can be utilized to derivatize 6β-akohols and in this case produced the 6β-methoxymethyl ether analogs III ($R^D$=—OH $R^6$=—OCH$_2$OCH$_3$, $R^{6'}$=—H). The above reactions are demonstrated in Examples 12 and 13.

Condensation of the ketone 11 with hydroxylamine (Scheme XII, step AB) provided two oximes as geometrical isomers E-19 and Z-20 which were separated chromatographically and then desilylated to provide pure III ($R^D$=—OH, $R^6$=$R^{6'}$=—(=N—OH (E)) and III ($R^D$=—OH, $R^6$=$R^{6'}$=—(=N—OH (Z)). O-alkyl or substituted hydroxylamines or hydrazines should also condense similarly with ketones 11.

The 7,19 cyclopropane derivatives could be prepared using conditions known in the art. Selectively protecting the C-6 alcohol of compound 4 to give compound 7, as in Scheme II, step G, followed by treatment with DAST would provide the cyclopropane as described in U.S. Pat. No. 5,254,580 issued Oct. 19, 1993, and European Patent Application 600,517A1 published Jun. 8, 1994. Alternatively compound 7 could be treated with methanesulfonyl chloride or other sulfonylating reagent in pyridine or other amine base with DMAP as a catalyst to provide the C-7 a sulfonate. Heating the sulfonate on silica gel as described by R. A. Johnson in *Tetrahedron Letters*, Vol. 35, No 43, pp 7893–7896 (1994) would provide the 7,19 cyclopropane with an oxygen substitutent at C-6. Heating with other Lewis acids other then silica gel has been noted by others to provide C-7,19 cyclopropanes. Deprotecting of the C-6 hydroxyl group would provide the C-6 α alcohol from which derivatives could be prepared as described above. This alcohol could then be oxidized and reduced as above to provide the C-6 β alcohol and derviatives thereof.

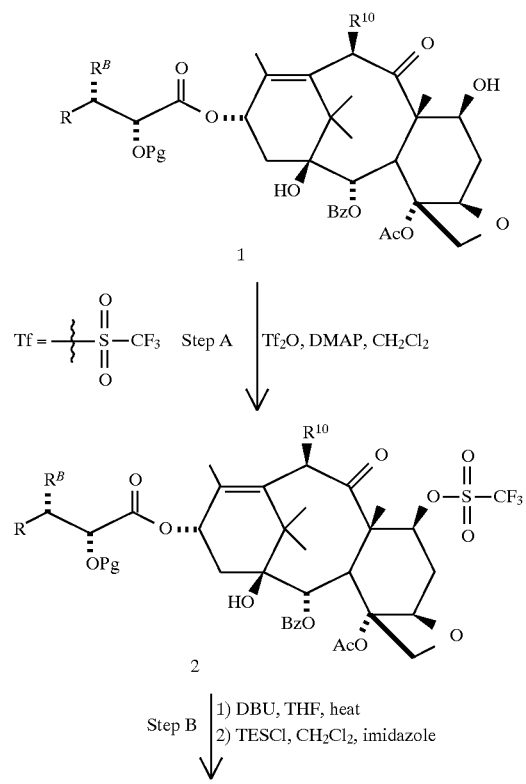

Scheme I

Scheme I
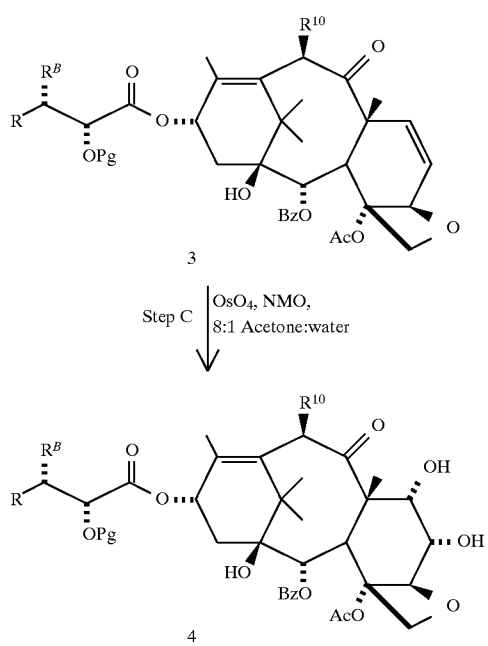
3
Step C | OsO₄, NMO,
8:1 Acetone:water
4
Scheme II
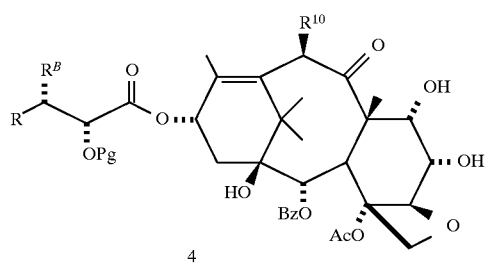
4
step D | <image of thiocarbonyldiimidazole>, DMAP
Scheme II
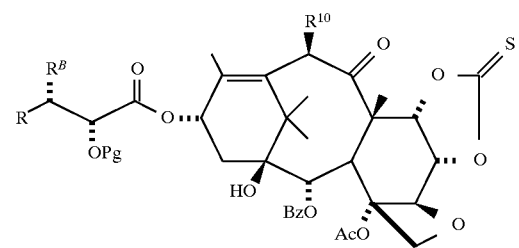
5
step E | Bu₃GeH, AIBN, Toluene,
80° C.
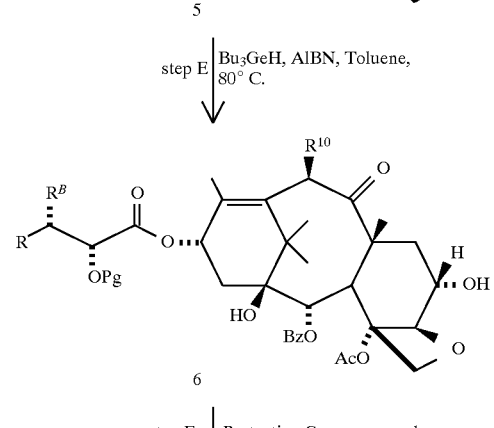
6
step F | Protecting Group removal
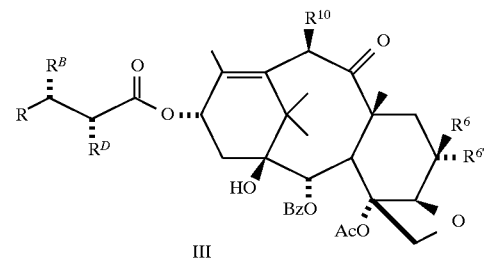
III
$R^D$ = —OH, $R^6$ = —H, R' = —OH
Pg = Protecting group Scheme III
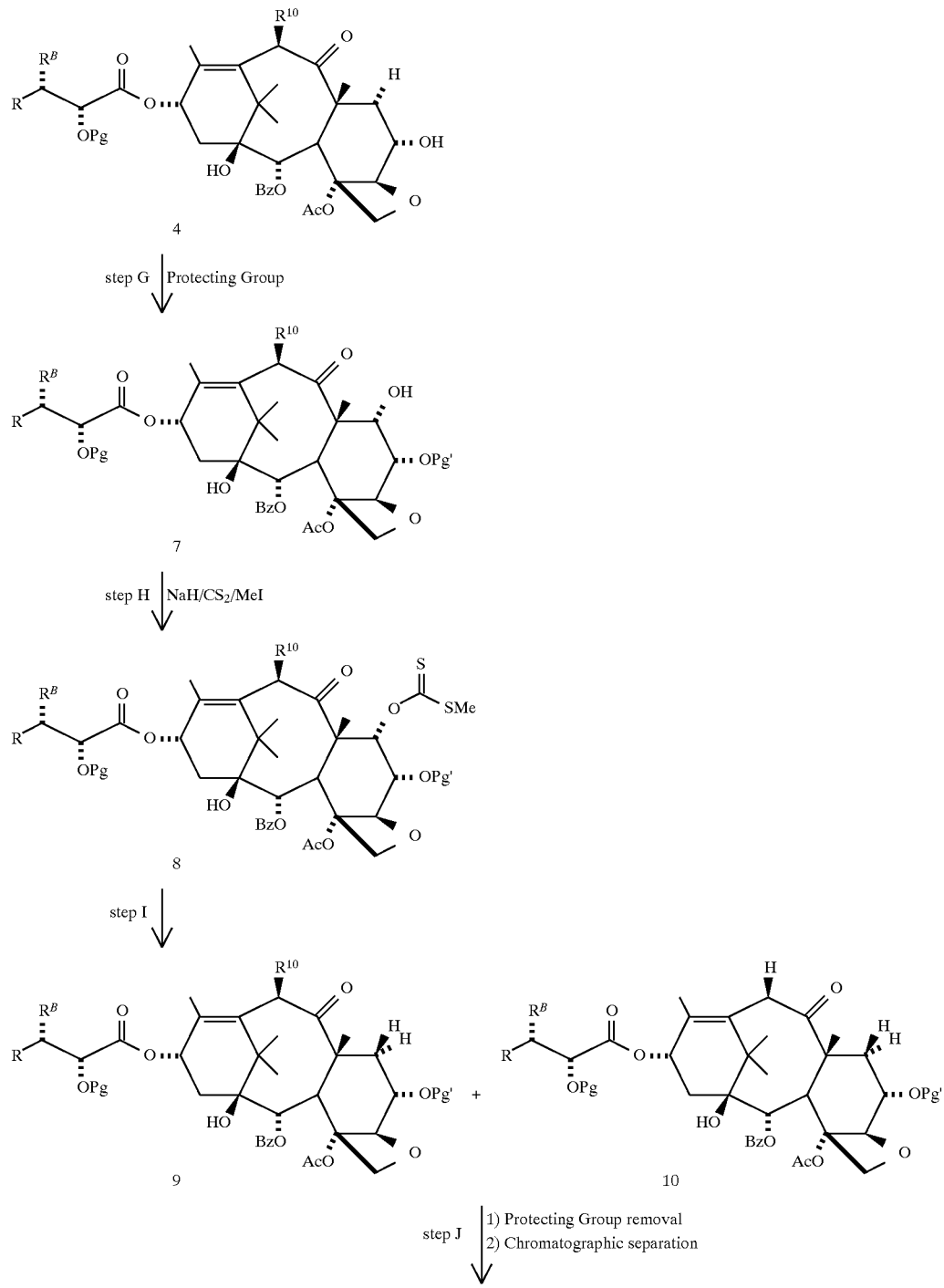

-continued
Scheme III
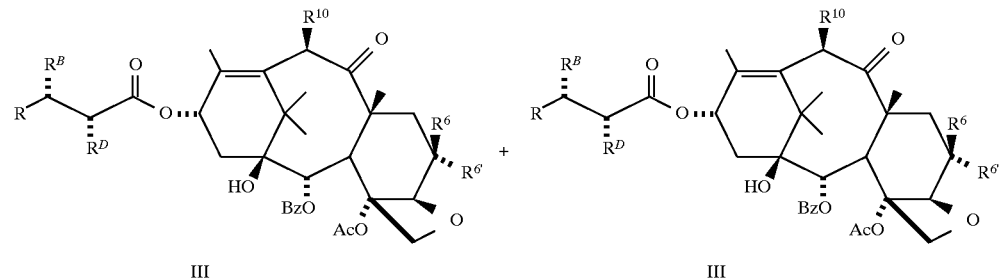
III
$R^D = $ —OH, $R^6 = $ —H, $R^{6'} = $ —OH
III
$R^D = $ —OH, $R^6 = $ —H, $R^{6'} = $ —OH, $R^{10} = $ —H
Pg = Protecting group
Scheme IV
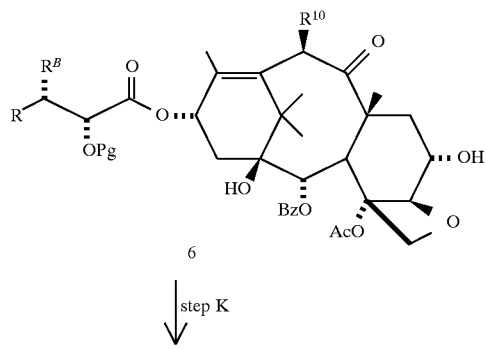
6
↓ step K
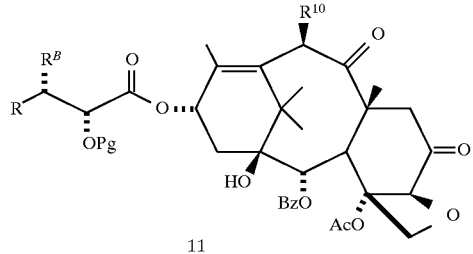
11
↓ step L
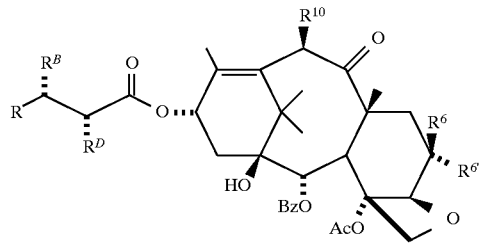
III
$R^D = $ —OH, $R^6 = R^{6'} = $ =O(oxo)
Scheme V
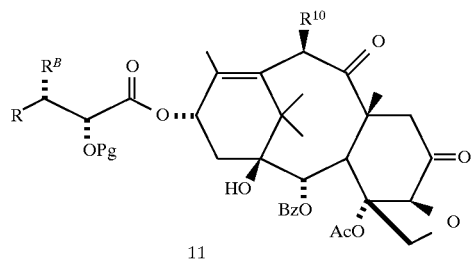
11
↓ step M
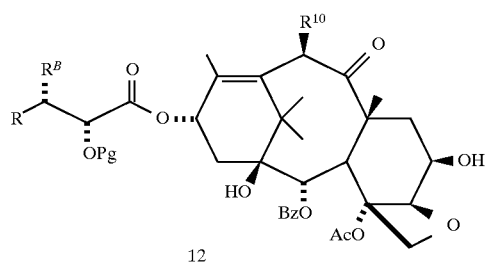
12
↓ step N
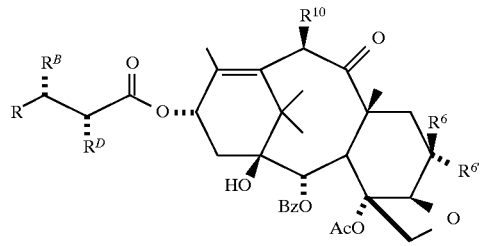
III
$R^D = $ —OH, $R^6 = $ —OH, $R^{6'} = $ —H Scheme VI
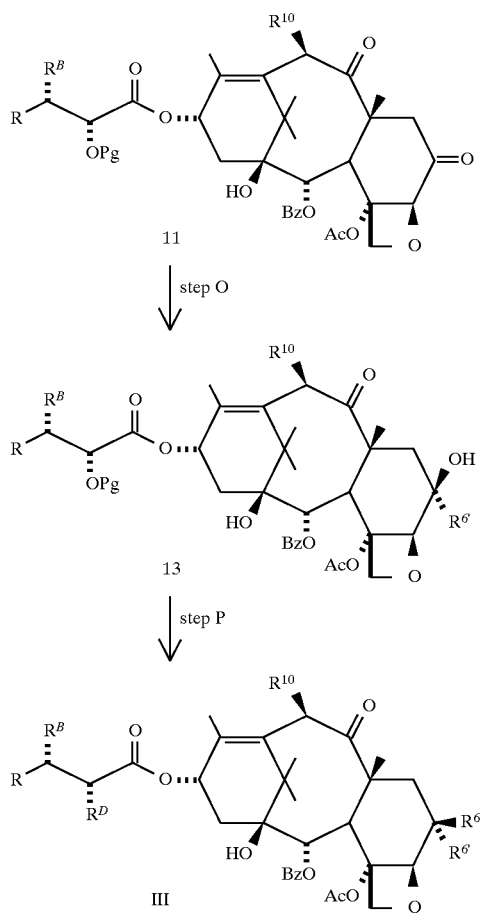
$R^D = -OH, R^6 = -OH, R^{6'} = -CH_3$
Scheme VII
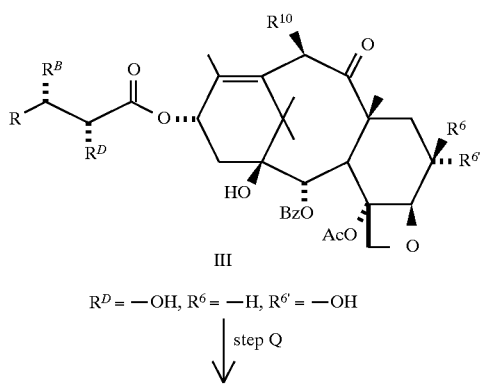
III
$R^D = -OH, R^6 = -H, R^{6'} = -OH$
step Q
-continued
Scheme VII
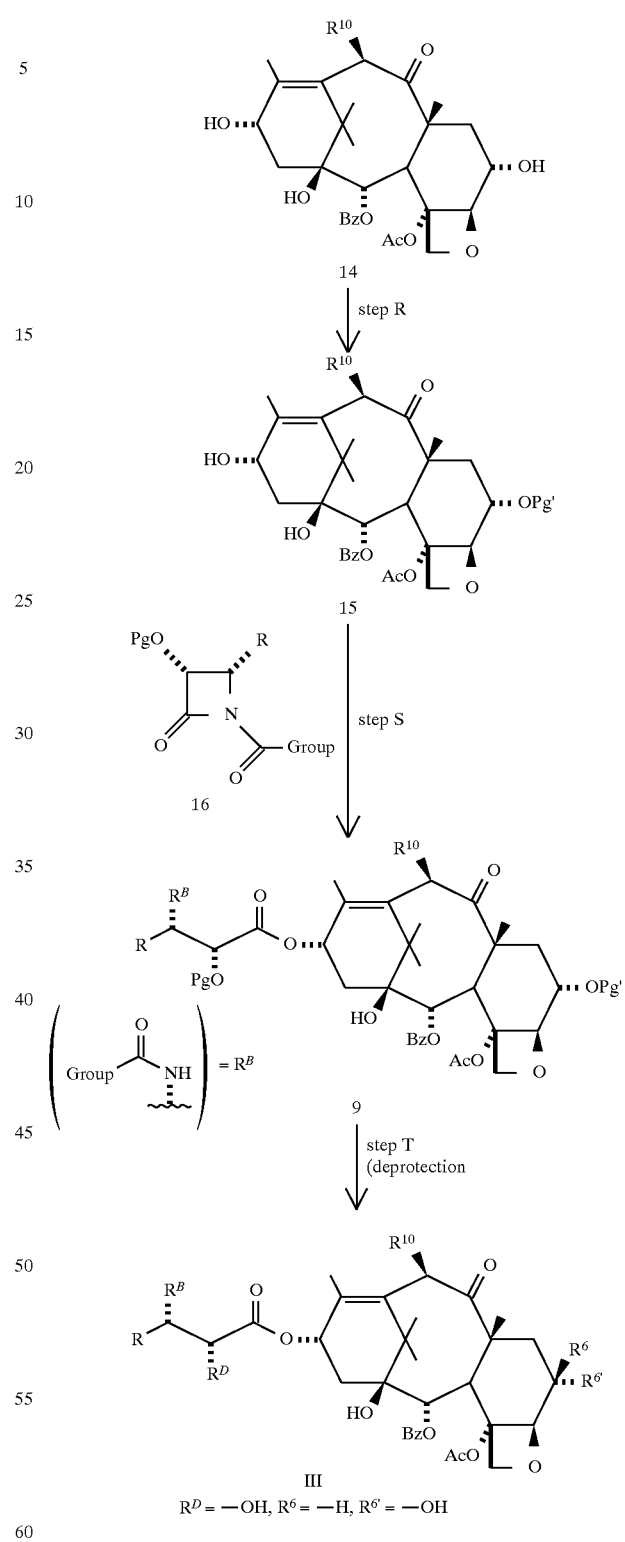
III
$R^D = -OH, R^6 = -H, R^{6'} = -OH$

Scheme VIII
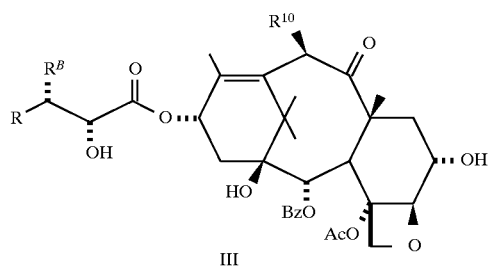
III
$R^D = $ —OH, $R^6 = $ —H, $R^{6'} = $ —OH
step U
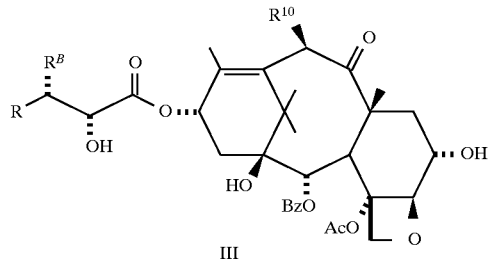
III
$R^D = $ —OH, $R^6 = R^{6'} = $ =O(oxo)
step V
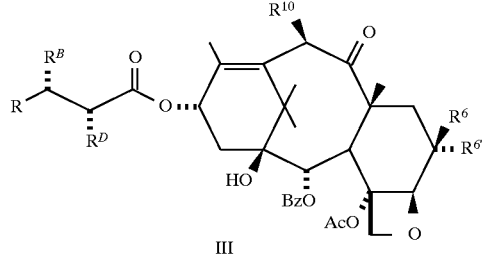
III
$R^D = $ —OH, $R^6 = $ —OH, $R^{6'} = $ —H
Scheme IX
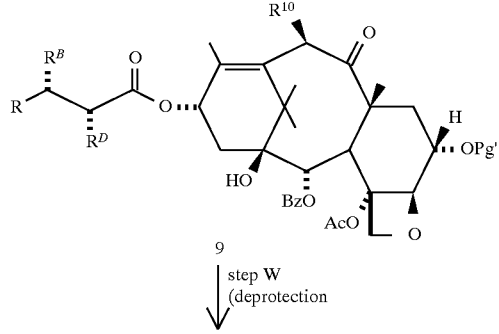
9
step W
(deprotection
Scheme IX
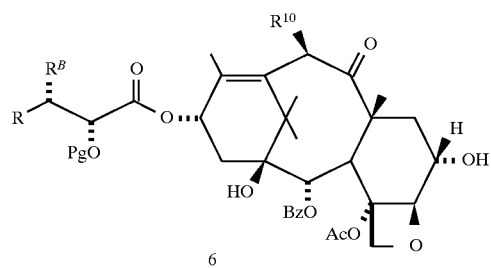
6
Scheme X
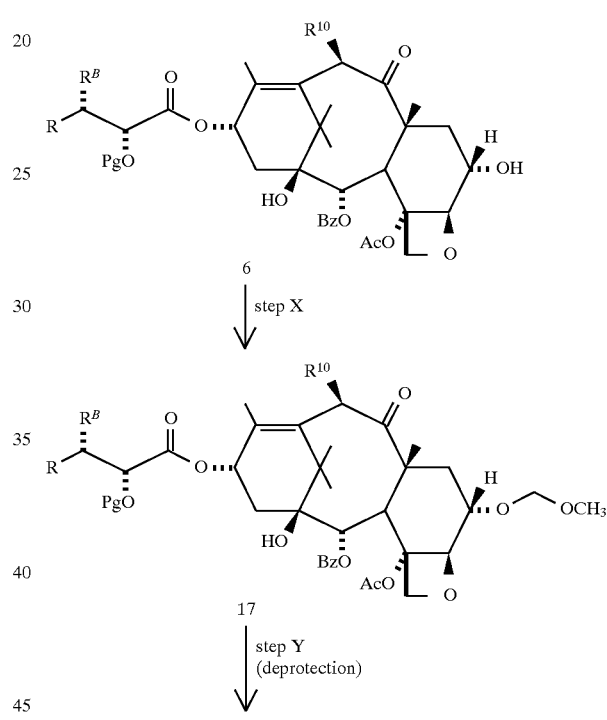
III
$R^D = $ —OH, $R^6 = $ —H, $R^{6'} = $ —OCH$_2$OCH$_3$

Scheme XI
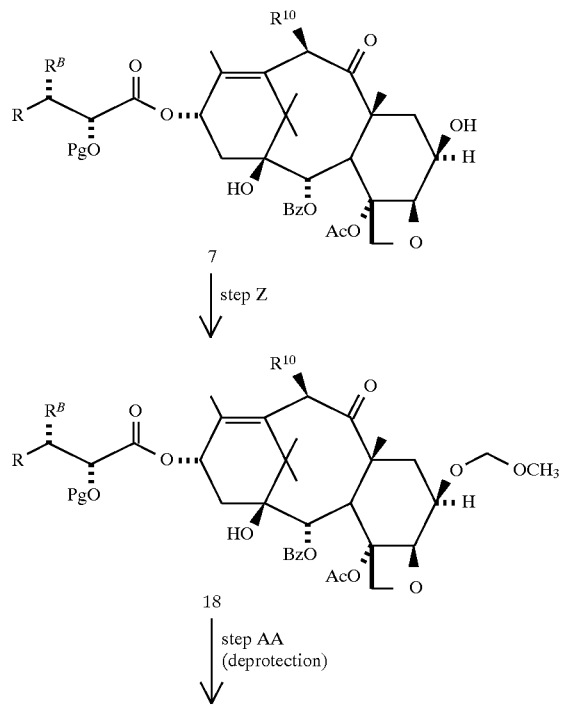
step Z
step AA
(deprotection)
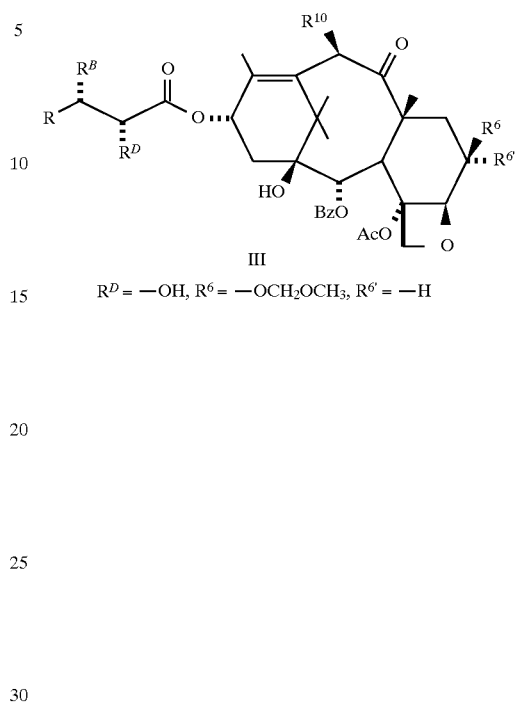
III
$R^D = -OH$, $R^6 = -OCH_2OCH_3$, $R^{6'} = -H$
Scheme XII
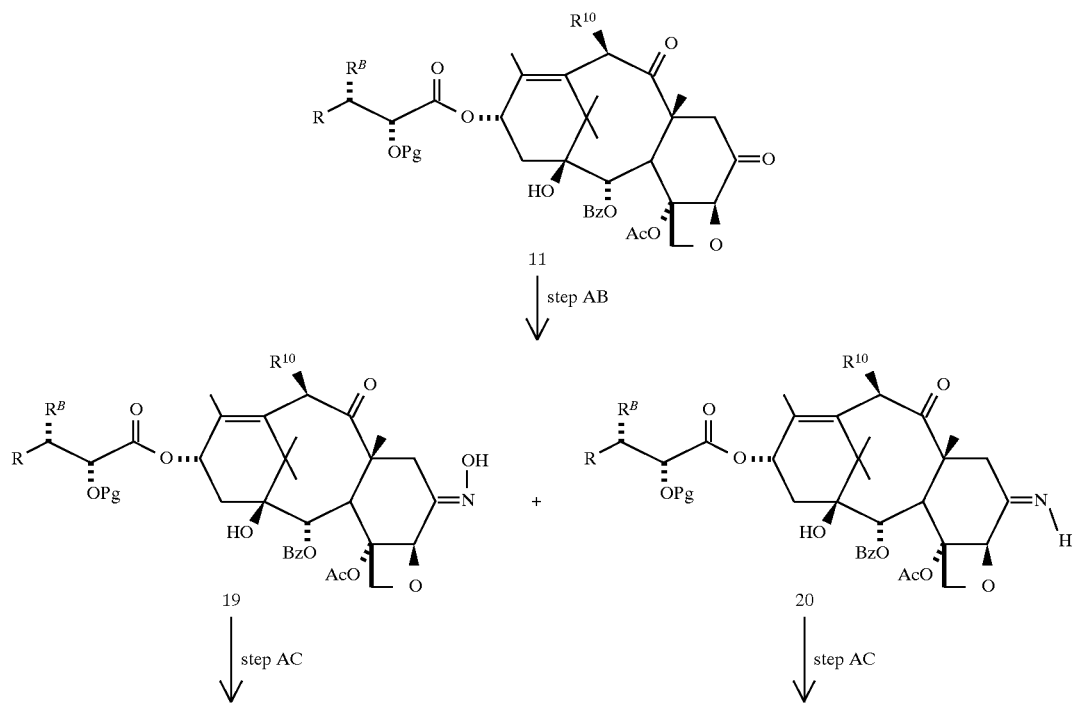
step AB
step AC -continued
Scheme XII

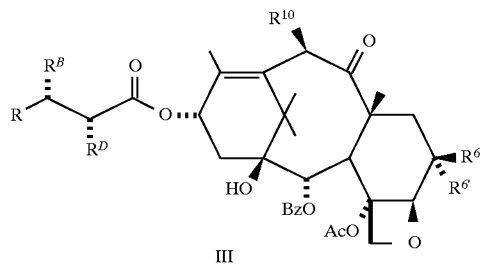

III $R^D = -OH, R^6 = R^{6'} = -(=N-OH(E))$ (E oxime)

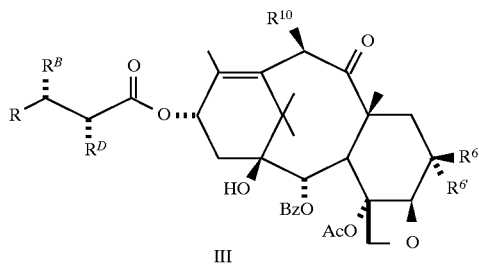

III $R^D = -OH, R^6 = R^{6'} = -(=N-OH(Z))$ (Z oxime)

Using Schemes I–XII, the preparation of Compounds IIIa–IIIr having the formula IV.

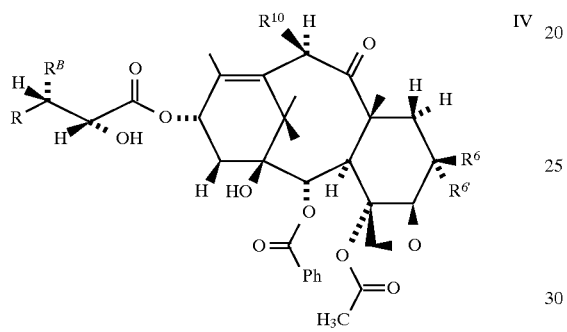

IV in Table 1 below are shown respectively in examples 1–16 that follow.

TABLE 1

| Cmpd. | R | $R^B$ | $R^6$ | $R^{6'}$ | $R^{10}$ |
|---|---|---|---|---|---|
| IIIa | Ph- | PhCOHN— | —H | —OH | AcO— |
| IIIb | Ph- | PhCOHN— | —H | —OH | H— |

| Cmpd. | R | $R^B$ | $R^6$ & $R^{6'}$ together | | $R^{10}$ |
|---|---|---|---|---|---|
| IIIc | Ph- | PhCOHN— | =O | | AcO— |

| Cmpd. | R | $R^B$ | $R^6$ | $R^{6'}$ | $R^{10}$ |
|---|---|---|---|---|---|
| IIId | Ph- | PhCOHN— | —OH | —H | AcO— |
| IIIe | Ph- | PhCOHN— | —OH | —CH$_3$ | AcO— |
| IIIf | 2-furyl- | tBuO$_2$CHN— | —H | —OH | AcO— |
| IIIg | Ph- | nC$_5$H$_{11}$COHN— | —H | —OH | AcO— |
| IIIh | pF-Ph- | PhCOHN— | —H | —OH | AcO— |

| Cmpd. | R | $R^B$ | $R^6$ & $R^{6'}$ together | | $R^{10}$ |
|---|---|---|---|---|---|
| IIIi | 2-furyl- | tBuO$_2$CHN— | =O | | AcO— |

| Cmpd. | R | $R^B$ | $R^6$ | $R^{6'}$ | $R^{10}$ |
|---|---|---|---|---|---|
| IIIj | 2-furyl- | tBuO$_2$CHN— | —OH | —H | AcO— |
| IIIk | Ph- | nC$_5$H$_{11}$COHN— | —OH | —H | AcO— |
| IIIl | pF-Ph- | PhCOHN— | —OH | —H | AcO— |
| IIIm | Ph- | PhCOHN— | —H | —OCH$_2$OCH$_3$ | AcO— |
| IIIn | Ph- | PhCOHN— | —OCH$_2$OCH$_3$ | —H | AcO— |
| IIIq | —CH=C(CH$_3$)$_2$ | PhCOHN— | —OH | —H | AcO— |
| IIIr | Ph- | tBuO$_2$CHN— | —OH | —H | AcO— |

| Cmpd. | R | $R^B$ | $R^6$ & $R^{6'}$ together | | $R^{10}$ |
|---|---|---|---|---|---|
| IIIo | Ph- | PhCOHN— | =N—OH(E) | | AcO— |
| IIIp | Ph- | PhCOHN— | =N—OH(Z) | | AcO— |

The preparation of the starting materials and intermediates, 1a–20a, in Table 2 below, according to Schemes I–XII are described in the examples, and in the section just prior to the examples.

TABLE 2

| Cmpd. | R | $R^B$ | $R^{10}$ | Pg |
|---|---|---|---|---|
| 1a | Ph- | PhCOHN— | AcO— | —SiEt$_3$ |
| 1b | Ph- | PhCOHN— | AcO— | —SitBuMe$_2$ |
| 2a | Ph- | PhCOHN— | AcO— | —SiEt$_3$ |
| 2b | Ph- | PhCOHN— | AcO— | —SitBuMe$_2$ |
| 3a | Ph- | PhCOHN— | AcO— | —SiEt$_3$ |
| 3b | Ph- | PhCOHN— | AcO— | —SitBuMe$_2$ |
| 4a | Ph- | PhCOHN— | AcO— | —SiEt$_3$ |
| 4b | Ph- | PhCOHN— | AcO— | —SitBuMe$_2$ |
| 5a | Ph- | PhCOHN— | AcO— | —SiEt$_3$ |
| 6a | Ph- | PhCOHN— | AcO— | —SiEt$_3$ |
| 6b | Ph- | nC$_5$H$_{11}$COHN— | AcO— | —SiEt$_3$ |

| Cmpd. | R | $R^B$ | $R^{10}$ | Pg | Pg' |
|---|---|---|---|---|---|
| 6c | pF-Ph- | PhCOHN— | AcO— | —SiEt$_3$ | |
| 6d | (CH$_3$)$_2$C=CH— | PhCOHN— | AcO— | —SiEt$_3$ | |
| 6e | Ph- | tBuO$_2$CHN— | AcO— | —SiEt$_3$ | |
| 7a | Ph- | PhCOHN— | AcO— | —SitBuMe$_2$ | —SitBuMe$_2$ |
| 8a | Ph- | PhCOHN— | AcO— | —SitBuMe$_2$ | —SitBuMe$_2$ |
| 9a | Ph- | PhCOHN— | AcO— | —SiEt$_3$ | —SiEt$_3$ |
| 9b | Ph- | PhCOHN— | AcO— | —SitBuMe$_2$ | —SitBuMe$_2$ |
| 9c | 2-furyl- | tBuO$_2$CHN— | AcO— | —SiEt$_3$ | —SiEt$_3$ |
| 9d | Ph- | nC$_5$H$_{11}$COHN— | AcO— | —SiEt$_3$ | —SiEt$_3$ |
| 9e | pF-Ph- | PhCOHN- | AcO— | —SiEt$_3$ | —SiEt$_3$ |
| 9f | (CH$_3$)$_2$C=CH— | PhCOHN— | AcO— | —SiEt$_3$ | —SiEt$_3$ |
| 9g | Ph- | tBuO$_2$CHN— | AcO— | —SiEt$_3$ | —SiEt$_3$ |

| Cmpd. | R | $R^B$ | Pg | Pg' |
|---|---|---|---|---|
| 10a | Ph- | PhCOHN— | —SitBuMe$_2$ | —SiEt$_3$ |
| 10b | Ph- | PhCOHN— | —SitBuMe$_2$ | —SitBuMe$_2$ |

| Cmpd. | R | $R^B$ | $R^{10}$ | Pg |
|---|---|---|---|---|
| 11a | Ph- | PhCOHN— | AcO— | —SiEt$_3$ |
| 11b | Ph- | nC$_5$H$_{11}$COHN— | AcO— | —SiEt$_3$ |
| 11c | pF-Ph- | PhCOHN— | AcO— | —SiEt$_3$ |
| 11d | (CH$_3$)$_2$C=CH— | PhCOHN— | AcO— | —SiEt$_3$ |
| 11e | Ph- | tBuO$_2$CHN— | AcO— | —SiEt$_3$ |
| 12a | Ph- | PhCOHN— | AcO— | —SiEt$_3$ |

| Cmpd. | R | $R^B$ | $R^{6'}$ | $R^{10}$ | Pg |
|---|---|---|---|---|---|
| 13a | Ph- | PhCOHN— | —CH$_3$ | AcO— | —SiEt$_3$ |

| Cmpd. | $R^{10}$ |
|---|---|
| 14a | AcO— |

| Cmpd. | $R^{10}$ | Pg |
|---|---|---|
| 15a | AcO— | —SiEt$_3$ |

| Cmpd. | R | Group | Pg |
|---|---|---|---|
| 16a | 2-furyl- | tBuO$_2$C— | —SiEt$_3$ |
| 16b | Ph- | nC$_5$H$_{11}$COHN— | —SiEt$_3$ |

| Cmpd. | R | $R^B$ | $R^{10}$ | Pg |
|---|---|---|---|---|
| 17a | Ph- | PhCOHN— | AcO— | —SiEt$_3$ |
| 18a | Ph- | PhCOHN— | AcO— | —SiEt$_3$ |
| 19a | Ph- | PhCOHN— | AcO— | —SiEt$_3$ |
| 20a | Ph- | PhCOHN— | AcO— | —SiEt$_3$ |

Some of the schemes refer to a hydroxy protecting group, preferably trialkylsilyl group. It is to be understood that hydroxy protecting group may be a carbonate or ester group —C(O)OR$^x$ or —C(O)R$^x$. Thus when such a group is employed as a hydroxy protecting group, it may either be removed to generate the free hydroxy protecting group or it may remain as a part of the final product.

By now there are many publications teaching the introduction of a wide variety of groups onto a taxane core. By using these well established methods or obvious variants thereof, the starting taxanes of formula VII, or hydroxy protected analogues thereof, can be readily made. For example, for transforming C4-acetoxy into other functional groups see, S. H. Chen et al., *J. Organic Chemistry*, 59, pp 6156–6158 (1994) and PCT application WO 94/14787 published Jul. 7, 1994; for converting C2-benzoyloxy to other groups see, S. H. Chen et al, *Bioorganic and Medicinal Chemistry Letters*, Vol. 4, No. 3, pp 479–482 (1994); K. C. Nicolaou A. et al., *J. Am. Chem. Soc.*, 1995, 117, 2409 and European Patent Application 617,034A1 published Sep. 28, 1994; for modifying C10-acetyloxy see, K.V. Rao et al., J. Med. Chem., 38, pp 3411–3414 (1995), J. Kant et al., *Tetrahedron Letters*, Vol. 35, No. 31, pp 5543–5546 (1994); and U.S. Pat. No. 5,294,637 issued Mar. 15, 1994; for making C10 and/or C7 unsubstituted (deoxy) derivatives see, European Patent Application 590,267A2 published Apr. 6, 1994 and PCT application WO 93/06093 published Apr. 1, 1993; for making C-10 epi hydroxy or acyloxy compounds see PCT application WO 96/03394; for making C-10 deoxyC-10 alkyl analogs see PCT application W095/33740; for making 7β,8β-methano, 6α,7α-dihydroxy and 6,7-olefinic groups see, R. A. Johnson, Tetrahedron Letters, Vol. 35, No 43, pp 7893–7896 (1994), U.S. Pat. No. 5,254,580 issued Oct. 19, 1993, and European Patent Application 600,517A1 published Jun. 8, 1994; for making C7/C6 oxirane see, X. Liang and D. G. I. Kingston, *Tetrahedron Letters*, Vol. 36, No. 17, pp 2901–2904 (1995); for making C7-epi-fluoro see, G. Roth et al, *Tetrahedron Letters*, Vol 36, pp 1609–1612 (1995); for forming C7 esters and carbonates see, U.S. Pat. No. 5,272,171 issued Dec. 21, 1993 and S. H. Chen et al., Tetrahedron, 49, No. 14, pp 2805–2828 (1993); for 9α- and 9β-hydroxy taxanes see, L. L. Klein, *Tetrahedron Letters*, Vol 34, No 13, pp 2047–2050 (1993), PCT application WO 94/08984 published Apr. 28, 1994, U.S. Pat. No. 5,352,806 issued Oct. 4,1994, PCT application WO 94/20485 published Sep. 15, 1994, and G. I. Georg et. al. *Tetrahedron Letters*, Vol 36, No 11, pp 1783–1786 (1995).

DESCRIPION OF SPECIFIC EMBODIMENTS

The specific examples that follow illustrate the syntheses of the compounds of the instant invention, and is not to be construed as limiting the invention in sphere or scope. The method may be adapted to variations in order to produce the compound embraced by this invention but not specifically disclosed. Further, variations of the methods to produce the same compound in somewhat different manner will also be evident to one skilled in the art.

In the following experimental procedures, all temperatures are understood to be in Centigrade (C) when not specified. The nuclear magnetic resonance (NMR) spectral characteristics refer to chemical shifts (δ) expressed in parts per million (ppm) versus tetramethylsilane (TMS) as reference standard. The relative area reported for the various shifts in the proton NMR spectral data corresponds to the number of hydrogen atoms of a particular functional type in the molecule. The nature of the shifts as to multiplicity is reported as broad singlet (bs or br s), broad doublet (bd or br d), broad triplet (bt or br t), broad quartet (bq or br q), singlet (s), multiplet (m), doublet (d), quartet (q), triplet (t), doublet of doublet (dd), doublet of triplet (dt), and doublet of quartet (dq). The solvents employed for taking NMR spectra are acetone-$d_6$ (deuterated acetone). DMSO-$d_6$ (perdeuterodimethylsulfoxide), $D_2O$ (deuterated water), $CDCl_3$ (deuterochloroform) and other conventional deuterated solvents. The infrared (IR) spectral description include only absorption wave numbers ($cm^{-1}$) having functional group identification value.

Celite is a registered trademark of the Johns-Manville Products Corporation for diatomaceous earth.

The abbreviations used herein are conventional abbreviations widely employed in the art. Some of which are: DAB (deacetylbaccatin III); MS (mass spectrometry); HRMS (high resolution mass spectrometry); Ac (acetyl); Ph (phenyl); v/v (volume/volume); FAB (fast atom bombardment); NOBA (m-nitrobenzyl alcohol); min (minute(s)); h or hr(s) (hour(s)); DCC (1,3-dicyclohexylcarbodiimide); BOC (t-butoxycarbonyl); CBZ or Cbz (benzyloxycarbonyl); Bn (benzyl); Bz (benzoyl); Troc (2,2,2-trichloroethyloxycarbonyl), DMS (dimethylsilyl), TBAF (tetrabutylammonium fluoride), DMAP (4-dimethylaminopyridine); TES (triethylsilyl); DMSO (dimethylsulfoxide); THF (tetrahydrofuran); HMDS (hexamethyldisilazane); MeOTf (methyltriflate); NMO (morpholine-N-oxide); $(DHQ)_2PHAL$ (hydroquinine 1,4-phthalazinediyl diether). Tf=triflate=trifluoromethanesulfonate; LRMS (low resolution mass spectrometry); ESI (electrospray ionization).

Preparation of Starting Materials (Scheme I)

2'-O—(triethylsilyl)-paclitaxel [1a]

Paclitaxel (15 g, 17.57 mmol) was dissolved in a solution of 60 mL of pyridine and 60 mL of dichloromethane and then the mixture was cooled to 0° C. Triethylsilyl chloride (11.8 mL, 70.3 nmmol) and the reaction was stirred for 90 min at 0°. The reaction was diluted with ethyl acetate, washed successively with water and then brine, dried over anhydrous magnesium sulfate, filtered, and concentrated in vacuo. The crude material was purified by flash chromatography over silica gel using 2:1 hexane/ethyl acetate as eluent to provide 17.0 g (99%) of the title compound.

2'-O-(t-butyldimethylsilyl)-paclitaxel [1b]

Paclitaxel (146.0 mg, 0.17 mmol) was dissolved in dry N,N-dimethylformamide (1 mL). To this solution imidazole (116.1 mg, 1.7 mmol) and t-butyldimethylsilyl chloride (128.8 mg, 0.85 mmol) were added successively and the mixture was stirred at 60° C. for 1 hour. The reaction mixture was then diluted with ethyl acetate (2 mL), followed by water. The aqueous layer was washed with additional ethyl acetate (2×2 mL). The combined organic layers were then washed with water and brine, dried over sodium sulfate, and evaporated to give crude product. Purification of the crude product by preparative TLC (silica gel, 7:3 hexane: ethyl acetate) furnished 2'-O(t-butyldimethylsilyl)-paclitaxel (157 mg, 95% yield).

2'-O-(triethylsilyl)-7β-O-trifluoromethanesulfonylpaclitaxel [2a]

The alcohol 1a (17 g, 17.5 mmol) and DMAP (8.55 g, 70 mmol) was dissolved in dichloromethane and then the mixture was cooled to 0° C. Trifluoromethanesulfonic anhydride (3.39 mL, 20.1 mmol) was added via syringe and then reaction was allowed to warm to ambient temperature. The reaction was stirred for 2 hours, was diluted with ethyl acetate, washed successively with water and then brine, dried over anhydrous magnesium sulfate, filtered, and concentrated in vacuo. The crude material was purified by flash chromatography over silica gel using 2:1 hexane/ethyl acetate as eluent to provide 17.6 g (91%) of the title compound.

2'-O-(t-Butyldimethylsilyl)-7β-O-trifluoromethanesulfonylpaclitaxel [2b]

2'-(t-butyldimethylsilyl)paclitaxel [1b] (180.0 mg, 0.19 mmol) was dissolved in dry $CH_2Cl_2$ (2 mL). To this solution 4-dimethylaminopyridine (61.0 mg, 0.5 mmol) and trifluoromethanesulfonyl chloride (50 mL, 0.5 mmol) were added successively at 0° C. and the mixture was stirred at room temperature for 1 hour. Then to this solution addtional 4-dimethylamino pyridine (61.0 mg, 0.5 mmol) and trifluoromethanesulfonyl chloride (50 mL, 0.5 mmol) were added successively and the mixture was stirred at room temperature for additional 1.5 hours. The reaction mixture then was diluted with EtOAc (4.0 mL) and the precipitate was filtered off on Celite. The solvent was evaporated, and the residue was purified by preparative TLC (silica gel, 6:4 hexane: EtOAc) to furnish 2'-(t-butyldimethylsilyl)-7-O-trifluoromethanesulfonylpaclitaxel (187.0 mg, 92% yield). $^1$H NMR (CDCl$_3$, TMS, 400 MHz) δ8.12 (d, 2H), 7.73 (d, 2H), 7.60 (t, 1H), 7.53–7.30 (m, 10H), 7.09 (d, 1H, J=8.9, HNH), 6.62 (s, 1H, H$_{10}$), 6.25 (t, 1H, J=9.2, H$_{13}$), 5.76 (q, 1H, J=8.9, 2.6, H$_3$'), 5.74 (d, 1H, J=7.0, H$_2$), 5.49 (dd, 1H, J=7.5, 10.1, H$_7$), 4.94 (d 1H, J=8.6, H$_5$), 4.67 (d, 1H, J=2.0, H$_2$'), 4.37 (d, 1H, J=8.5, H$_{20}$), 4.22 (d, 1H, J=8.5, H$_{20}$), 3.97 (d, 1H, J=7.0, H$_3$),2.85 (m,1H, H$_6$) 2.60 (s, 3H, —CH$_3$), 2.39 (m, 1H, H$_{14}$), 2.19 (s, 3H, —CH$_3$), 2.18 (m, 2 H, H$_6$, H$_{14}$), 2.08 (s, 3H, —CH$_3$), 1.89 (s, 3H, —CH$_3$), 1.22 (s, 3H, —CH$_3$), 1.18 (s, 3H, —CH$_3$), 0.8 (s, 9H), −0.02 (s, 3H), −0.29 (s, 3H). $^{13}$C NMR (CDCL$_3$, TMS, 100 MHz) d 200.97, 171.89, 171.16, 169.34, 167,71, 167.42, 141.75, 138.77, 134.66, 134,45,133.48, 132.46, 130.84, 129.52, 129.47, 129.40, 129.38, 128.65, 127.59, 127.00, 86.39, 83.68, 80.64, 79.25, 76.94, 75.77, 75.74, 74.92, 71.69, 57.97, 56.23, 47.55, 43.75, 36.32, 34.67, 26.76, 26.23, 26.13, 23.47, 22.01,21.29, 18.75, 14.87, 14.80, 11.538, −4.54, −5.20. LRFABMS m/z caled for C$_{54}$H$_{65}$NO$_{16}$F$_3$SiS [MH]+1100, found 1100.

2'-O-(triethylsilyl)-6,7-dehydropaclitaxel [3a]

The triflate 2a (17.6 g, 16mmol) was dissolved in 75 mL of dry THF and then 12.18g (80mmol) of DBU was added. The reaction was heated at reflux for 2 hours and then diluted with ethyl acetate. The organic layer was washed five times with water and then brine, dried over anhydrous magnesium sulfate, filtered, and concentrated in vacuo. The crude product was dissovled in methylene chloride and then 16 mmol of irnidazole and 8 mmol of triethylsilyl chloride were added. The reaction was stirred for 1.5h at ambient temperature, diluted with ethyl acetate, washed with two portions of water, dried over anhydrous magnesium sulfate and concentrated in vacuo. The crude material was purified by flash chromatography over silica gel using 2:1 hexane/ ethyl acetate as eluent to provide 15.0 g (99%) of the title compound.

2'-O-(t-butyldimethylsilyl)-6,7-dehydropaclitaxel [3b]

To a stirred solution of 2'-(t-butyldimethylsilyl)-7β-trifluoromethanesulfonylpaclitaxel [2b], (202.0 mg, 0.18 mmol) in dry dichloromethane (1.0 mL) was added 1,8-diazabicyclo (5,4,0) undec-7-ene (DBU, 300.0 mL, 2.0 mmol). The mixture was kept stirring at 40° C. for 4 hours. The reaction mixture then was diluted with ethyl acetate (2.0 ml) and washed with diluted HCl, diluted NaHCO$_3$ solution, water and brine. The aqueous layer was extracted with additional ethyl acetate (2×2 mL). The combined organic layers were dried over sodium sulfate and evaporated to give crude product. Purification of the crude product by preparative silica gel TLC (7:3 hexane:ethyl acetate) furnished two compounds: 2'-(t-butyldimethylsilyl)-6,7-dehydropaclitaxel [3b] (150.0 mg, 86%) and 6,7-dehydropaclitaxel (21.3 mg, 13.9%). Spectoscopic data for 3b: $^1$H-NMR (CDCl$_3$, TMS, 400 MHz) δ8.12 (d, 2H), 7.73 (d, 2H), 7.60 (t, 1H), 7.53–7.30 (m, 5H), 7.07 (d, 1H, J=8.9, H$_{NH}$), 6.24 (s, 1H, H$_{10}$), 6.25 (t, 1H, J=9.2, H$_{13}$), 6.08 (dd,H, J=9.9,5.6, H$_6$), 5.87 (d, 1H, J=9.9, H$_7$), 5.86 (d, 1H, J=6.5, H$_2$), 5.72 (d, 1H, J=8.6, H$_3$'), 5.12 (d 1H, J=5.5, H$_5$), 4.65 (d, 1H, J=2.0, H$_2$'), 4.45 (d, 1H, J=8.1, H$_{20}$), 4.34 (d, 1H, J=8.1, H$_{20}$), 4.03 (d, 1H, J=6.5, H$_3$), 2.58 (s, 3H, —CH$_3$), 2.44 (m, 1H, H$_{14}$), 2.22 (s, 3H, —CH$_3$), 2.18 (m, 2 H, H$_6$, H$_{14}$), 1.88 (s, 3H, —CH$_3$), 1.83 (s, 3H, —CH$_3$), 1.24 (s, 3H, —CH$_3$), 1.14 (s, 3H, —CH$_3$), 0.79 (s, 9H), —0.05 (s, 3H), −0.32 (s, 3H). $^{13}$C NMR (CDCl$_3$, TMS, 100 MHz) δ205.44, 171.32, 169.56, 169.39, 166.91, 166.87, 141.60, 140.03, 138.27, 134,06, 133.67, 133.61, 131.76, 130.19, 129.16, 128.80, 128.73, 128.71, 128.69, 127.92, 126.96, 126.36, 126.126, 81.22, 81.12, 76.31, 75.82, 75.64, 75.12, 71.23, 60.36, 55.65, 55.40, 35.98, 26.29, 25.49 23.14, 22.12, 22.02, 20.744, 20.46, 18.09, 14.62, 14.17, −5.28, −5.89. LRFABMS m/z calcd for C$_{53}$H$_{64}$NO$_{13}$Si [MH]+950, found 950.

2'-O-(triethylsilyl)-6α-hydroxy-7-epi-paclitaxel [4a]

The olefin 3a was dissolved in 180 mL of acetone and 22.5 mL of water. NMO (4.06 g, 34.74 mmol) was added followed by 10 mole % OsO$_4$ and the reaction was stirred for 12 days. Silica gel was added and the reaction was concentrated in vacuo to provide a near free flowing powder which was placed on top of a flash chromatography silica gel column. Elution with 1:1 hexane/ ethyl acetate provided 13.35 g (86%) of the desired diol.

2'-O-(t-Butyldimethylsilyl)-6α-hydroxy-7-epi-paclitaxel [4b]

To a solution of 2'-O-(t-butyldimethylsilyl)-6,7-dehydropaclitaxel [3b], (60.0 mg, 0.063 mmol) in THF (500 mL, 10 drops H$_2$O) were added osmium tetraoxide (2.5 wt. 2.5% solution in 2-methyl-2-propanol, 150 mL, 0.015 mmol) and 4-methyl morpholine-N-oxide (NMO, 50 mg, 0.42 mmol). The mixture was kept stirring at room temperature for 4 hours. Additional osmium tetraoxide solution (150 mL, 0.015 mmol) was then added to the reaction mixture to accelerate the reaction. The reaction mixture was kept stirring at room temperature for additional 5 hours. To the reaction solution was added sodium bisulfite (25 mg) and the mixture was stirred for 10 minutes, then diluted with EtOAc (1 mL), filtered through Celite, and washed with H$_2$O and brine. The aqueous layer was extracted with additional EtOAc (2×2 mL). The combined organic layers were dried over Na$_2$SO$_4$ and evaporated. Isolation of the residue on preparative TLC plate (silica gel, 1:1 hexane: EtOAc) furnished starting material (7.2 mg, 12%) and a more polar compound 2'-O-(t-butyldimethylsilyl)-6a-hydroxy-7-epi-paclitaxel [4b] (48.0 mg, 78% yield). $^1$H NMR (CDCl$_3$, TMS, 400 MHz) δ8.15 (d, 2H), 7.70 (d, 2H), 7.64–7.26 (m, 6H), 7.07 (d, 1H, J=8.8, HNH), 6.83 (s, 1H, H$_{10}$), 6.29 (t, 1H, J=8.8, H$_{13}$), 5.79 (q, 1H, J=8.8, 2.4, H$_3$'), 5.74 (d, 1H, J=7.6, H$_2$), 4.71 (d, 1H, J=12.0, H$_{7\text{-}OH}$), 4.68 (d, 1H, J=2.0, H$_5$), 4.66 (bs, 2H, H$_{20}$), 4.36 (s, 1H, H$_2$'), 4.18 (m, 1H, H$_6$), 3.87 (d, 1H, J=7.6, H$_3$), 3.70 (q, 1H, J=5.2, 12.0, H$_7$), 2.90 (d, 1H, J=8.2, H$_{6\text{-}OH}$), 2.62 (s, 3H, —CH$_3$), 2.42–2.10 (m, 2H, H$_{14}$) 2.18 (s, 3H, —CH$_3$), 1.90 (s, 3H, —CH$_3$), 1.62 (s, 3H, —CH$_3$), 1.18 (s, 3H, —CH$_3$), 1.12 (s, 3H, —CH$_3$), 0.78 (s, 9H), −0.03 (s, 3H), −0.3 (s, 3H). HRFABMS m/z calcd for C$_{47}$H$_{52}$NO$_{15}$ [MH]+870.3337, found 870.3336.

Example 1

Preparation of 7-deoxy-6α-hydroxypaclitaxel [IIIa]- (Scheme II)

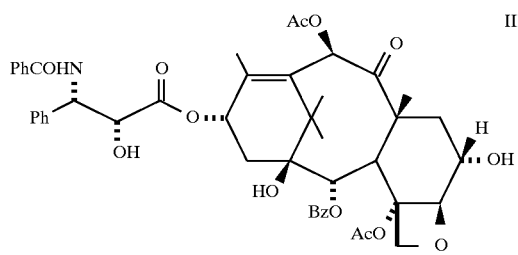

IIIa

The diol 4a (1.773 g, 1.809 mmol), thiocarbonyldiimidazole(0.996 g, 5.427 mmol), DMAP (0.618 g, 5.065 mmol) were dissolved in 50 mL THF and allowed to stir overnight. The reaction was diluted with EtOAc, washed with NaHCO$_3$, and brine. The solution was dried over MgSO$_4$, filtered, and concentrated. The residue was chromatographed over silica gel (1:1 hexane/ethyl acetate) to yield 1.646 g of product 5a (89%).

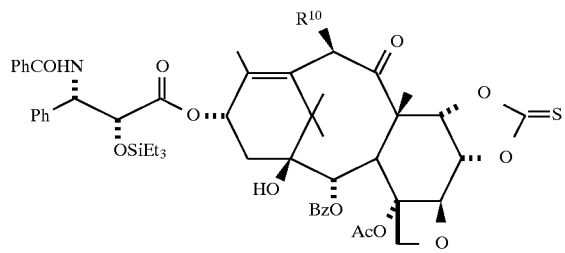

5a

ESILRMS M+NH$_4^{1+}$ calcd. for C$_{54}$H$_{63}$O$_{15}$N$_2$S Si: 1043. Found: 1043.

Anal. calcd. for C$_{54}$H$_{63}$O$_{15}$N S Si: C, 63.20; H, 6.19; N, 1.36. Found: C, 63.04; H, 6.22; N, 1.33.

IR(KBr) 3438(br.), 2958, 1746, 1717,1282, 1236 cm$^{-1}$.

$^1$H NMR (CDCl$_3$, 300 MHz) δ8.15(d, J=7.2 Hz, 2H), 7.74(d, J=7.2 Hz, 2H), 7.63–7.32(m, 11H), 7.12(d, J=9.0 Hz, 1H), 6.87(s, 1H), 6.25(br. t., 1H), 5.83(d, J=6.9Hz, 1H), 5.70(d, J=9.0, 1H), 4.97(d, J=11.4 Hz, 1H), 4.87(s, 1H), 4.72(m, 2H), 4.39(d, J=8.1 Hz, 1H), 4.22(d, J=8.1 Hz, 1H), 4.00(D, J=6.9 Hz, 1H), 2.57(s, 3H), 2.43-2.35(m, 1H), 2.21(s, 3H), 2.16–2.08(m, 1H), 2.03(m, 4H), 1.87(s, 3H), 1.21(s, 3H), 1.17(s, 3H), 0.79(m, 9H), 0.44(m, 6H).

The thiocarbonate 5a (0.200 g, 0.196 mmol), AIBN(cat.), (aza-isobutyrylnitrile (catalytic)) and Bu$_3$GeH(0.479 g, 1.96 mmol) were dissolved in 3 mL toluene under Argon. The reaction mixture was frozen, dried in vacuo, and thawed three times to remove O$_2$. The reaction was heated to 85° C. for 1 hr. The reaction mixture was concentrated and chromatographed over silica gel (1.5:1 hexane/ethyl acetate) to yield 0.137 g of product 6α (72%).

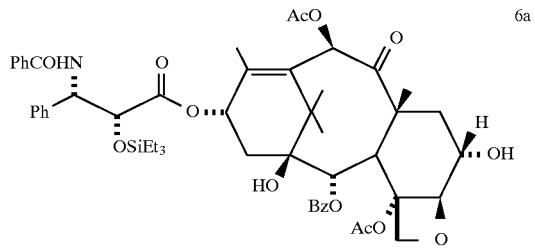

6a

ESILRMS M+H calcd for C$_{53}$H$_{65}$O$_{14}$N Si: 968. Found: 968.

Anal. calcd. for C$_{53}$H$_{65}$O$_{14}$NSi·H$_2$O: C, 64.55; H, 6.85; H, 1.42. Found: C, 64.49; H, 6.82; N, 1.41.

IR(KBr) 3442(br.), 2956, 1734, 1486, 1372, 1244, 710 cm$^{-1}$.

$^1$H NMR (CDCl$_3$, 300 MHz) 8 8.13(d, J=8.7 Hz, 2H), 7.72(d, J=8.4 Hz, 2H), 7.62-7.33(m, 11H), 7.10(d, J=8.7 Hz, 1H), 6.45(s, 1H), 6.24(t, J=8.7 Hz, 1H), 5.71–5.64(m, 2H), 4.80(s, 1H), 4.66(d, J=2.1 Hz, 1H), 4.31(d, J=8.4 Hz, 1H), 4.18–4.14(m, 2H), 3.78(d, J=7.5 Hz, 1H), 2.54(s, 3H), 2.48–2.39(m, 1H), 2.20(s, 3H), 2.17-2.08(m, 1H), 2.02(d, J=9.0 Hz, 2H), 1.90(s,4H), 1.77(s,1H), 1.71(s, 3H), 1.19(s, 3H), 1.10(s, 3H), 0.79(m, 9H), 0.41(m,6H).

To a solution of the 6-a alcohol 6a (7.63 g, 7.89 mmol) in acetonitrile at 0° C. was added 1N HCl (15.78 mL, 15.78 mmol) and the solution stirred for 1 hr. The solution was diluted with ethyl acetate, washed with saturated bicarbonate and brine, dried over MgSO$_4$, and concentrated. The residue was chromatographed over silica gel (2:1 hexane/ethyl acetate) to give 6.07 g of diol III (90%).

ESIHRMS M+H calcd for C$_{47}$H$_{52}$NO$_{14}$854.3388 Found: 854.3377.

IR(KBr) 3436(br.), 2985, 1732, 1648, 1244 cm$^{-1}$.

$^1$H NMR (CDCl$_3$, 300 MHz) 5 8.13(d, J=6.9 Hz, 2H), 7.70(d, J=6.9 Hz, 2H), 7.60–7.26(m, 11H), 6.94(d, J=9.0, 1H), 6.41(s, 1H), 6.20(br. t., 1H), 5.77(d, J=6.3 Hz, 1H), 5.64(d, J=7.5 Hz, 1H), 4.77(s, 2H), 4.28(d, J=8.4 Hz, 1H), 4.16–4.08(m, 2H), 3.76(d, J=7.2 Hz, 1H), 3.48(s, 1H), 2.40–2.36(m, 4H), 2.28–2.19(m, 4H), 2.01–1.80(m, 4H), 1.80 (s, 3H), 1.70(s, 3H), 1.19(s, 3H), 1.10(s, 3H).

$^{13}$C NMR (Acetone, 300 MHz) δ173.5, 170.9, 169.7, 166.5, 141.6, 140.3, 135.5, 134.5, 134.0, 132.1, 131.2, 130.8, 129.4, 129.2, 129.1, 128.3, 128.19, 128.15, 93.7, 85.1, 78.8, 77.3, 76.4, 74.7, 74.6, 71.6, 71.5, 56.8, 53.7, 45.0, 44.3, 43.7, 37.1, 30.5, 28.9, 28.8, 26.6, 23.0, 22.2, 20.6, 16.3, 14.5.

Alternate Deoxygenation Procedure

To a solution of the thiocarbonate 5a (0.201 g, 0.197 mmol)in toluene (6.4 mL) was added Bu$_3$SnH (0.530 ml, 1.97 mmol)and AIBN (cat.). The reaction mixture was refluxed for 15 min., cooled, and concentrated. The residue was chromatographed over silica gel (1:1 hexane/ethyl acetate) to give 120 mg of a mixture of two products (63%). To a solution of the deoxygenation products (0.373 g, 0.386 mmol) in CH$_3$CN (5 mL) at 0° C. was added 1N HCl (0.771 mL, 0.771 mmol). The reaction was stirred at 0° C. for 50 min., diluted with EtOAc, washed with NaHCO$_3$, and brine. The solution was dried over MgSO$_4$ concentrated and the residue chromatographed over silica gel (1:2 hexane/ethyl acetate) to give the desired diol IIIa 176 mg along with 54 mg of the C-10 desacetyl derivative IIIb.

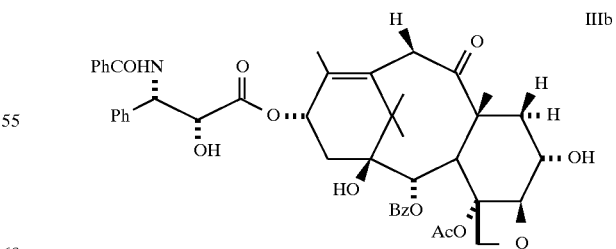

IIIb

C-10 desacetyl diol [IIIb]:

ESIHRMS M+H calcd. for C$_{45}$H$_{50}$NO$_{12}$796.3333. Found: 796.3361.

IR(KBr) 3436(br.), 1728, 1648, 1272, 1108 cm$^{-1}$.

$^1$H NMR (CDCl$_3$, 300 MHz) δ8.13(d, J=8.4 Hz, 2H), 7.72(d, J=8.4 Hz, 2H), 7.63–7.30(m, 11H), 6.96(d, J=8.7 Hz, 1H), 6.11(t, J=9.0, 1H), 5.78(d, J=9.0 Hz, 1H), 5.65(d, J=7.5

Hz, 1H), 4.77–4.73(m, 2H), 4.28(d, J=7.8 Hz, 1H), 4.16–4.06(m, 2H), 3.96(d, J=6.6 Hz, 1H), 3.80(d, J=16.5 Hz, 2H), 3.47–3.31(m, 3H), 2.44–2.36(m, 4H), 2.27–2.20(m, 1H), 1.95(d, J=9.0 Hz, 2H), 1.68(s, 3H), 1.66(s, 3H), 1.15(s, 3H), 1.08(s, 3H).

Alternate preparation of title compound of example 1 (Scheme III)

2'-O-(t-Butyldimethylsilyl)-6α-hydroxy-7-epi-paclitaxel [4b] (7.2 mg) was dissolved in dry N,N-dimethylformamide (400 mL). To this solution imidazole (22 mg, 44 eq.) and t-butyldimethylsilyl chloride (28 mg, 25 eq.) were added successively and the mixture was stirred at 70° C. for 14 hours. The reaction mixture was then diluted with ethyl acetate (2 mL) and washed with diluted HCl, diluted NaHCO$_3$, and water followed by brine. The combined organic layers were dried over sodium sulfate and evaporated to give crude product Purification of the crude product by preparative TLC (silica gel, 7:3 hexane:ethyl acetate) furnished 2',6α-O-di(t-butyldimethylsilyl)paclitaxel [7a] (7.5 mg, 83% yield).

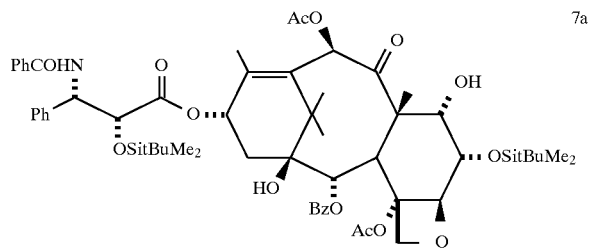

$^1$H NMR (CDCl$_3$, TMS, 400 MHz) δ 8.15 (d, 2H), 7.70 (d, 2H), 7.64–7.26 (m, 6H), 7.08 (d, 1H, J=8.8, H$_{NH}$, 6.87 (s, 1H, H$_{10}$), 6.29 (t, 1H, J=8.8, H$_{13}$), 5.78 (q, 1H, J=8.8,2.4, H$_3$'), 5.73 (d, 1H, J=7.6, H$_2$), 4.74 (d, 1H, J=2.0, H$_5$), 4.66 (s, 1H, H$_2$'), 4.34 (2d, 2H, J=9.0, H$_{20}$), 4.18 (m, 1H, H$_6$), 3.98 (d, 1H, J=7.6, H$_3$), 3.92 (d, 1H, J=12.0, H$_{7-OH}$), 3.58 (q, 1H, J=12.0, H$_7$), 2.64 (s, 3H, —CH$_3$), 2.5 (m, 1H, H$_{14}$), 2.20 (s, 3H, —CH$_3$), 2.1 (m, 1H, H$_{14}$), 1.92 (s, 3H, —CH$_3$), 1.63 (s, 3H, —CH$_3$), 1.19 (s, 3H, —CH$_3$), 1.14 (s, 3H, —CH$_3$), 0.90 (s, 9H), 0.78 (s, 9H), 0.09 (s, 3H), 0.07 (s, 3H), −0.03 (s, 3H), −0.3 (s, 3H). LRFABMS m/z calcd for C$_{59}$H$_{79}$O$_{15}$NSi$_2$ [MH]+1098, found 1098.

To a solution of 2',6α-O-di(t-butyldimethylsilyl) paclitaxel [7a] (43.5 mg) in anhydrous THF was added sodium hydride (4.0 mg, 4 eq.). The reaction mixture was stirred for 15 minutes until the mixture turned yellow. To this yellow mixture were added carbon disulfide (148 mL, 60 eq.) and methyl iodide (144 mL, 60 eq.). The reaction was allowed to proceed at room temperature for 30 minutes. At this time the reaction mixture was diluted with ethyl acetate, followed by water. The aqueous layer was washed with additional ethyl acetate (2×4 mL). The combined organic layers were then washed with water and brine, and after drying over sodium sulfate, the solution was filtered and evaporated to yield the crude mixture which was subjected to preparative TLC three times (silica gel, 4:1 hexane : ethyl acetate) to afford 2',6α-O-di(t-butyldimethylsilyl)-7-epi-O—(Smethylthiocarboxy)paclitaxel [8a] (28.4 mg, 60% yield), 2',6α-O-di(t-butyldimethylsilyl)-2,7-epi--di (Smethylthiocarboxy)-1-benzoyl-2-debenzoylpaclitaxel (7.6 mg, 14% yield), and 2',6α-O-di(t-butyldimethylsilyl)-2,7-di(Smethylthiocarboxy)-1-benzoyl-2-debenzoylpaclitaxel (8.0 mg, 15% yield).

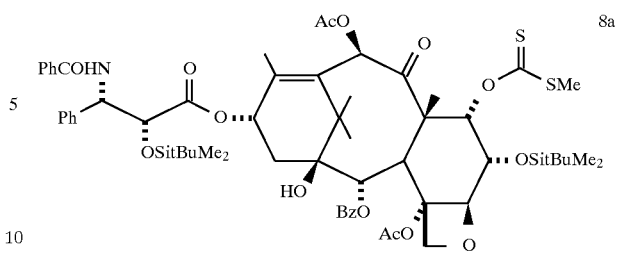

$^1$H-NMR for 2',6α-O-di(t-butyldinethylsilyl)-7-epi-O—(S-methylthiocarboxy)-paclitaxel [8a] (CDCl$_3$, TMS, 400 MHz) δ8.16 (d, 2H, J=7.26), 7.75 (d, 2H, J=7.0), 7.60 (t, 1H, J=7.5), 7.55–7.32 (m, 5H), 7.10 (d, 1H, J=9.0, H$_{NH}$), 6.29 (t, 1H, J=8.39, H$_{13}$), 6.26 (s, 1H, H$_{10}$), 6.17 (d, 1H, J=3.51, H7), 5.80 (q, 1H, J=9.0, 2.0, H$_3$'), 5.74 (d, 1H, 1=7.02, H$_2$), 4.77 (d 1H,J=4.42, H$_5$), 4.69 (d, 1H, J=2.0, H$_2$'), 4.59 (d, 1H, J=8.39, H$_{20}$), 4.35 (q, 1H, J=4.58, 3.66, H$_6$), 4.30 (d, 1H, J=8.26, H$_{20}$), 4.20 (d, 1H, J=7.02, H$_3$), 2.67 (s, 3H, —CH$_3$), 2.60 (s, 3H, —CH$_3$), 2.58 (m, 1H, H$_{14}$), 2.13 (s, 3H, —CH$_3$), 2.12 (m, H$_{14}$), 2.04 (s, 3H, —CH$_3$), 1.81 (s, 3H, —CH3), 1.19 (s, 3H, —CH$_3$), 1.14 (s, 3H, —CH$_3$), 0.80 (s, 9H), 0.78 (s, 9H), −0.003 (s, 3H), −0.008 (s, 3H), −0.04 (s, 3H), −0.32 (s, 3H). $^{13}$C NMR for 2',6α-O-di(t-butyldimethylsilyl)-7-epi-O—(Smethylthiocarboxy)paclitaxel (CDCl$_3$, TMS, 100 MHz) 5 216.4 (C xanthyl), 205.3 (C9), 171.3 (C1'), 169.1 (C4 carbonyl), 168.7 (C10 carbonyl), 166.9 (C2 carbonyl), 166.8 (C amide), 141.3 (C12), 138.3, 134.1 133.7 (C11), 132.8, 131.7, 130.2 129.1, 128.8, 128.7, 128.7, 127.9, 127.0, 126.4,90.1 (C5), 86.6 (C7), 85.4 (C4), 79.2 (C20), 78.6 (C1), 77.0 (C10), 75.8 (C2), 75.1 (C2'), 74.1 (C6), 71.1 (C13), 56.3 (C8), 55.6 (C3'), 42.4 (C3), 40.6 (C15), 36.3 (C14), 26.0 (Cl7), 25.5,25.5,23.5 (SCH$_3$), 21.7 (C16), 20.7 (C10 OAc), 19.8 (C19), 19.8 (C4 OAc), 18.1, 17.8, 15.5 (C18), −5.1, −5.2, −5.2, −5.9. HRFABMS for 2',6α-O-di(t-butyldimethylsilyl)-7-epi-O(Smethylthiocarboxy) paclitaxel: [MNa]+, molecular formula: C$_{61}$H$_{81}$O$_{15}$NS$_2$Si$_2$Na, error: 0.5 ppm.

$^1$H NMR for 2',6α-O-di(t-butyldimethylsilyl)-2,7-epi-O-di(S-methylthiocarboxy)-l-benzoyl-2-debenzoylpaclitaxel: (CDCl$_3$, TMS, 400 MHz) δ7.79 (d, 2H, J=7.0), 7.74 (d, 2H, J=7.0), 7.55–7.44 (m, 4H), 7.38–7.26 (m, 7H), 7.05 (d, 1H, J=9.16, H$_{NH}$), 6.78 (d, 1H, J=6.72, H$_2$), 6.65 (t, 1H, J=7.94, H$_{13}$), 6.26 (s, 1H, H$_{10}$), 6.17 (d, 1H, J=3.36, H$_7$), 5.86 (q, 1H, J=8.70, 2.4, H$_3$'), 4.93 (d, 1H, J=8.65, H$_{20}$), 4.78 (d 1H, J=5.03, H$_5$), 4.71 (d, 1H, J=2.14, H$_2$'), 4.43 (d, 1H, J=8.75, H20), 4.41 (q, 1H, J=4.78, 3.15, H$_6$), 4.39 (d, 1H, J=6.35, H$_3$), 3.57 (q, 1 H, J=15.72, 7.03, H$_{14}$), 2.65 (s, 3H, —CH$_3$), 2.62 (s, 3H, —CH$_3$), 2.51 (s, 1H, —CH3), 2.40 (q, 1 H, J=15.72, 7.03, H$_{14}$), 2.12 (s, 3H, —CH$_3$), 2.07 (s, 3H, —CH$_3$), 1.90 (s, 3H, —CH3), 1.24 (s, 3H, —CH$_3$), 1.22 (s, 3H, —CH$_3$), 0.81 (s, 9H), 0.77 (s, 9H), 0.06 (s, 3H), 0.03 (s, 3H), −0.03 (s, 3H), −0.32 (s, 3H). $^{13}$C NMR (CDCl$_3$, TMS, 100 MHz) δ216.2 (2 C xanthyl), 205.0 (C9), 171.0 (C1'), 169.5 (C4 carbonyl), 168.6 (C10 carbonyl), 166.9 (C amide), 164.8 (C1 carbonyl), 143.0 (C12), 138.3, 134.4 132.9 (C11), 131.5, 130.6, 130.3 129.6, 128.6, 128.6, 128.0, 127.7, 127.2, 126.4, 90.1 (C5), 88.9 (C1), 86.8 (C7), 85.4 (C4), 84.9 (C2), 79.4 (C20), 77.0 (C10), 75.4 (C2'), 73.9 (C6), 70.9 (C13), 56.6 (C8), 55.5 (C3'), 44.2 (C15),40.5 (C3), 31.4 (C14), 29.6 (C17), 25.5,25.5,23.5 (SCH$_3$), 22.8 (C16), 21.3 (C19), 20.7 (C10 OAc), 19.8 (SCH$_3$), 18.4 (C4 OAc), 18.1, 17.9, 15.6 (C18), —5.0, —5.2, −5.2, −6.0. HRFABMS m/z calcd for C$_{63}$H$_{83}$O$_{15}$NS$_4$Si$_2$Li [MLi]+ 1284.4344, found 1284.4319, error: 2.0 ppm.

$^1$H NMR for 2',6α-O-di(t-butyldimethylsilyl)-2,7-di(S-methylthiocarboxy)-1-benzoyl-2-debenzoylpaclitaxel:

(CDCl$_3$, TMS, 400 MHz) δ7.81 (d, 2H, J=7.0), 7.75 (d, 2H, J=7.0), 7.55–7.44 (m, 4H), 7.38–7.26 (m, 7H), 7.04 (d, 1H, J=9.00, H$_{NH}$), 6.84 (d, 1H, J=7.18, H$_2$), 6.84 (d, 1H, J=9.31, H$_7$), 6.61 (s, 1H, H$_{10}$), 6.59 (t, lH, J=8.09, H$_{13}$), 5.68 (q, 1H, J=8.70, 2.6, H$_3$'), 4.83 (d 1H, J=1.47, H$_5$), 4.74 (d, 1H, J=8.24, H$_{20}$), 4.68 (d, 1H, J=2.28, H$_2$'), 4.51 (d, 1H, J=8.24, H20), 4.37 (d, 1H, J=7.24, H$_3$), 4.26 (q, 1H, J=9.31, 1.98, H$_6$), 3.65 (q, 1 H, J=16.17, 8.24, H$_{14}$), 2.63 (s, 3H, —CH$_3$) ,2.54 (s, 3H, —CH$_3$), 2.45 (s, 3H, —CH$_3$),2.28 (q, 1 H=16.17,8.24, H$_{14}$), 2.12 (s, 3H, —CH$_3$), 2.08 (s, 3H, —CH$_3$), 1.89 (s, 3H, —CH$_3$), 1.25 (s, 3H, —CH$_3$), 1.22 (s, 3H, —CH$_3$), 0.83 (s, 9H), 0.76 (s, 9H), 0.04 (s, 3H), 0.02 (s, 3H), –0.05 (s, 3H), –0.33 (s, 3H). HRFABMS m/z calcd for C$_{63}$H$_{83}$O$_{15}$NS$_4$Si$_2$Li [MLi]$^+$ 1284.4344, found 1284.4316, error: 2.2 ppm.

To the solufion of 2',6α-di-O—(t-butyldimethylsilyl)-7α-O-(S-methylxanthyl)paclitaxel [8a] (12.0 mg) in toluene (750 mL) were added tributyltin hydride (40 mL), azobis (isobutyronitrile) (AIBN) (9 mg), and H$_2$O (1 drop). The reaction was allowed to proceed at 85° C. for 6 hours. The reaction was worked up by standard methods to yield the crude mixture which was subjected to preparative TLC (silica gel, 7:3 hexane: EtOAc), affording 2',6α-di4—(t-butyldimethylsilyl)-10-deacetoxy-7-deoxypaclitaxel [10] (8.2 mg, 76% yield).

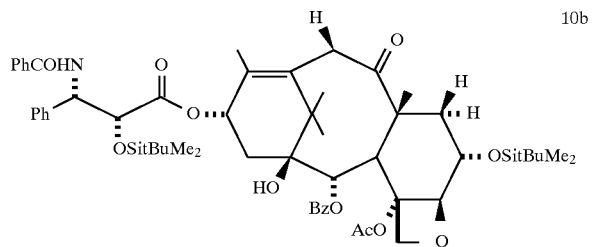

$^1$H NMR (CDCl$_3$, TMS, 400 MHz) δ8.14 (d, 2H, J=8.4), 7.75 (d, 2H, 1=8.4), 7.59 (t, 1H, J=7.5) 7.54–7.30 (m, 5H), 7.10 (d, 1H, J=8.7, H$_{NH}$), 6.20 (t, 1H, J=8.0, H$_{13}$), 5.74 (bd, 1H, J=8.9, H$_3$'), 5.66 (d, 1H, J=7.3, H$_2$), 4.72 (d, 1H, J=2.3, H$_5$), 4.64 (d, 1H, J=2.0, H$_2$'), 4.31 (d, 1H, J=8.9, H$_{20}$), 4.28 (d, 1H, J=8.9, H$_{20}$), 4.15 (m, 1H, H$_6$), 4.09 (d, 1H, J=7.3, H$_3$), 3.85 (d, 1H, J=16.8, H$_{10}$), 3.35 (bd, 1H, J=15.0, H$_{10}$), 2.47 (q, 1H, J=15.3,9.8, H$_{14}$), 2.08 (q, 1H, J=15.1,8.1, H$_{14}$), 2.18 (t, J=12.2, H$_7$), 1.61 (q, 1H, J=12.5,6.4, H$_7$), 2.59 (s, 3H, —CH$_3$), 1.81 (s, 3H, —CH$_3$), 1.66 (s, 3H, —CH$_3$), 1.17 (s, 3H, —CH$_3$), 1.08 (s, 3H, —CH3), 0.85 (s, 9H), 0.80 (s, 9H), 0.02 (s, 3H), 0.002 (s, 3H), –0.05 (s, 3H), –0.32 (s, 3H). $^{13}$C NMR (CDCl$_3$, TMS, 100 MHz) δ 211.2 (C9), 171.4 (C1'), 169.5 (C4 carbonyl), 167.0 (C amide), 166.8 (C2 carbonyl), 138.5 (C12), 134.1, 133.6 (C11), 133.3, 133.0 131.7, 130.2, 129.3, 128.7, 128.7, 128.6, 127.8, 127.0, 126.4, 92.5 (C5), 85.0 (C4), 79.1 (C1), 77.4 (C20), 76.0 (C2), 75.2 (C2'), 72.7 (C6), 71.5 (C13), 55.8 (C3'), 55.0 (C8), 44.4 (C10), 44.0 (C3), 43.5 (C15), 43.5 (C7), 36.4 (C14), 25.8 (C17), 25.5, 25.2,23.9 (C16), 23.2 (C4 OAc), 18.1, 18.1, 16.9 (C18), 14.2 (C19), –4.8, –4.9, –5.3, –5.9.

To a solution of 2',6α-O-di(t-butyldimethylsilyl)-7α-(S-methylthiocarboxy)paclitaxel [8a] (12.0 mg) in toluene (750 mL) were added tributyltin hydride (40 mL), azoisobutylnitrile (AIBN) (9 mg), and water (1 drop). The reaction was allowed to proceed at 75° C. for 3 hours. At this time the reaction mixture was diluted with ethyl acetate, followed by water. The aqueous layer was washed with additional ethyl acetate (2×4 mL). The combined organic layers were then washed with water and brine, and after drying over sodium sulfate, the solution was filtered and evaporated to yield the crude mixture which was subjected to preparative TLC (silica gel, 7:3 hexane : ethyl acetate), affording a mixture of 2',6α-di-O-(t-butyldimethylsilyl)- 7-deoxypaclitaxel [9b] and 2',6α-di-O(t-butyldimethylsilyl)-10-deacetoxy-7-deoxypaclitaxel [10b] (total 8.2 mg).

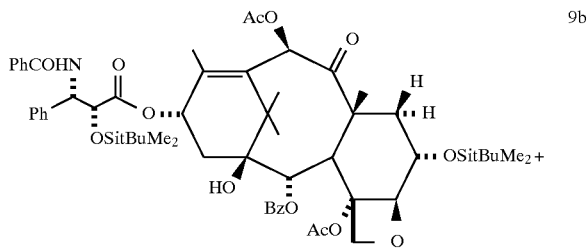

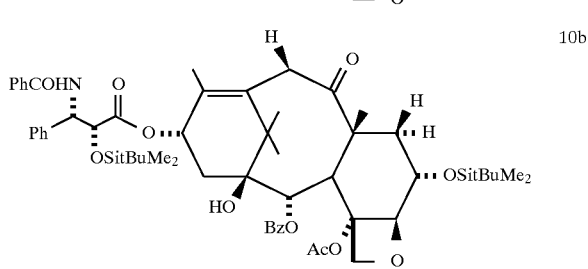

To a solution of the mixture of 2',6α-0-di(t-butyldimethylsflyl)-7-deoxypachitaxel [9b] and 2',6α-di-O—(t-butyldimethylsilyl)-10-deacetoxy7-deoxypaclitaxel [10b] (total 7.0 mg) in anhydrous THF (600 mL), was added HF and pyridine solution (150 mL). The reaction proceeded at room temperature for 4 hours. At this time the reaction mixture was diluted with ethyl acetate, followed by water. The aqueous layer was washed with additional ethyl acetate (2×4 mL). The combined organic layers were then washed with sodium bicarbonate solution, water and brine, and after drying over sodium sulfate, the solution was filtered and evaporated to yield the crude mixture which was subjected to repeated preparative TLC (silica gel, 3:2 hexane:ethyl acetate), affording 7-deoxy-6α-hydroxypaclitaxel [IIIa] (3.2 mg) and 10-deacetoxy-7-deoxy-6α-hydroxypaclitaxel [IIIb] (2.5 mg).

$^1$H-NMR for 7-deoxy-6α-hydroxypaclitaxel [IIIa]: (CDCl$_3$, TMS, 400 MHz) δ8.16 (d, 2H), 7.72 (d, 2H), 7.62 (t, 1H), 7.54–7.30 (m, 5H), 6.96 (d, 1H, J=8.9, NH), 6.44 (s, 1H, H$_{10}$), 6.22 (t, 1H, J=9.9, H$_{13}$), 5.80 (q, 1H, J=8.9, 2.3,H$_3$'), 5.66 (d, 1H, J=7.4, H$_2$), 4.79 (d, 1H, J=4.7, H$_5$), 4.78 (m, 1H, H$_2$'), 4.31 (d, 1H, J=8.4, H$_{20}$), 4.18 (d, 1H, J=8.4, H$_{20}$), 4.12 (m, 1H, H$_6$), 3.79 (d, 1H, J=7.2, H$_3$), 3.51 (d, 1H, J=4.7, H$_2$'-OH), 2.44–2.23 (m, 2H, H$_6$, H$_{14}$), 2.42 (s, 3H, —CH$_3$), 2.22 (s, 3H, —CH$_3$), 2.05–1.95 (m, 2H, H$_7$), 1.83 (s, 3H, —CH$_3$), 1.73 (s, 3H, —CH$_3$), 1.22 (s, 3H, —CH$_3$), 1.13 (s, 3H, —CH$_3$). $^{13}$C NMR for 7-deoxy6α-hydroxypaclitaxel (CDCl$_3$, TMS, 100 MHz) δ204.8 (C9), 172.8 (C1'), 170.7 (C4 carbonyl), 169.5 (C10), 167.1 (C amide), 167.1 (C2 carbonyl), 140.3 (C12), 137.9, 133.7, 133.5 (C1), 132.0, 130.2, 129.1, 128.8, 128.7, 128.4, 127.0, 126.9, 92.7 (C5), 83.7 (C4), 79.0 (C1), 76.3 (C20), 75.3 (C2), 73.9 (C10), 73.1 (C2'), 72.3 (C13), 70.8 (C6), 55.0 (C3'), 53.3 (C8), 45.0 (C3), 44.1 (C7), 42.9 (C15), 35.9 (C14), 26.2 (C17), 22.6 (C4 OAc), 21.4 (C16), 20.7 (C10 OAc), 15.1 (C18), 14.4 (C19). HRFABMS for 7-deoxy-6α-hydroxypaclitaxel: m/z [MNa]+876.3204, molecular formula: C$_{47}$HS$_{51}$O$_{14}$NNa, requires: 876.3207, error: 0.3 ppm.

$^1$H NMR for 10-deacetoxy-7-deoxy-6α-hydroxypaclitaxel [IIIb]: (CDCl$_3$, TMS, 400 MHz) δ 8.15 (d, 2H), 7.74 (d, 2H), 7.62 (t, 1H) 7.54–7.30 (m, 5H), 7.00

(d, 1H, J=8.4, H$_{NH}$), 6.13 (t, 1H, 1=8.8, H$_{13}$), 5.79 (q, 1H, J=8.9, 2.7, H$_3$'), 5.68 (d, 1H, J=7.0, H$_2$), 4.79 (bs, 1H, H$_5$), 4.77 (q, 1H, J=2.4, 5.2, H$_2$'), 4.30 (d, 1H, J=8.4, H$_{20}$), 4.17 (d, 1H, J=8.4, H$_{20}$), 4.12 (m, 1H, H$_6$), 3.98 (d, 1H, J=6.9, H$_3$), 3.80 (d, 1H, J=16.6, H$_{10}$), 3.49 (d, 1H, J=5.3, H$_2$'-OH), 3.36 (bd, 1H, J=15.6, H$_{10}$), 2.41-2.26 (m, 2H, H$_{14}$), 2.00-1.96 (m, 2H, H$_7$), 2.41 (s, 3H, —CH$_3$), 1.70 (s, 3H, -H3), 1.68 (s, 3H, —CH$_3$), 1.17 (s, 3H, —CH$_3$), 1.1 (s, 3H, —CH3). $^{13}$C NMR for 10-deacetoxy-7-deoxy-6α-hydroxypaclitaxel (CDCl$_3$, TMS, 100 MHz) δ210.1 (C9), 172.8 (C1'), 170.7 (C4 carbonyl), 167.0 (C amide), 167.0 (C2 carbonyl), 138.0 (C12), 133.7, 133.6 (C1), 132.3, 131.9, 130.2, 129.2, 129.0, 128.7, 128.7, 128.6, 128.3, 127.0, 126.9, 92.6 (C5), 83.7 (C4), 78.9 (C1), 76.4 (C20), 75.5 (C2), 73.1 (C2'), 72.6 (C13), 70.8 (C6), 55.4 (C8), 55.0 (C3'), 44.8 (C3), 44.2 (C10), 44.1 (C7), 42.7 (C15), 36.1 (C14), 25.2 (C17), 23.4 (C16), 22.7 (C4 OAc), 15.5 (C18), 14.0 (C19). HRFABMS for 10-deacetoxy-7-deoxy-6α-hydroxypaclitaxel: m/z [MNa]$^+$ 818.3131, molecular formula: C$_{45}$H$_{49}$O$_{12}$NNa, requires: 818.3152, error: 2.7 ppm.

Example 2

Preparation of 7-deoxy-6ketopaclitaxel [IIIc]-(Scheme IV)

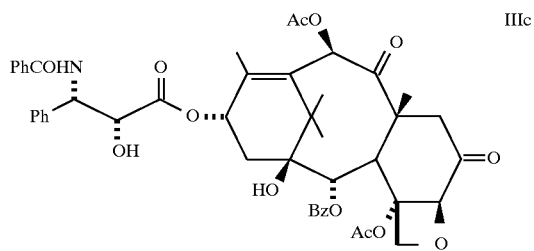

IIIc

A solution of the alcohol 6a (0.193 g, 0.2 mmol) and NMO(0.049 g, 0.419 mmol) in CH$_2$Cl$_2$(3 mL) was stirred over 4 Å molecular sieves for 10 min. before TPAP(10 mole %) was added as a solid. The reaction was stirred for 15 hrs. The solution was filtered through celite, concentrated, diluted with EtOAc, washed with Na$_2$SO$_3$, and brine. The solution was dried over MgSO$_4$, filtered, and concentrated. The residue was chromatographed over silica gel (1:1 hexane/ethyl acetate) to give 0.145 g of ketone 11a (75%).

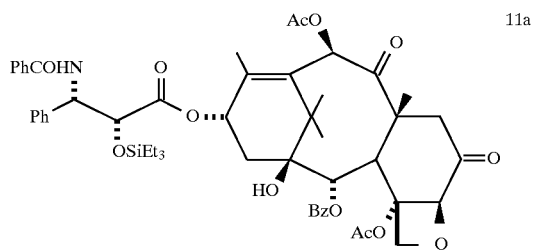

11a

ESILRMS M+H calcd for C$_{53}$H$_{64}$O$_{14}$N Si: 966. Found: 966.

Anal. calcd. for C$_{53}$H$_{63}$O$_{14}$N Si-H$_2$O: C, 64.48; H, 6.65; N, 1.42. Found: C, 64.73; H, 6.54; N,1.36.

IR(KBr) 3442(br.), 2956, 1730, 1666, 1484, 1372, 1242 cm$^{-1}$.

$^1$H NMR (CDCl$_3$, 300 MHz) δ 8.14(d, J=6.9 Hz, 2H), 7.71(d, J=8.7 Hz, 2H), 7.60–7.31(m, 11H), 7.09(d, J=9.0 Hz, 1H), 6.42(s, 1H), 6.27(br. t., 1H), 5.74–5.69(m, 2H), 4.82(s, 1H), 4.68(d, J=2.1 Hz, 1H), 4.39( dd, J=19.5, 8.7 Hz, 2H), 4.13(d, J=7.5 Hz, 1H), 3.15(d, J=14.1 Hz, 1H), 2.59(s, 3H), 2.51–2.42(m, 1H), 2.31(d, J=13.8 Hz, 1H), 2.20(s, 3H), 2.19–2.10(m, 1H), 1.91(s, 3H), 1.72(s, 1H), 1.67(s, 3H), 1.22(s, 3H), 1.11(s, 3H), 0.79(m, 9H), 0.42(m, 6H).

A solution of the silyl ketone 11a (0.051 g, 0.053 mmol) in CH$_3$CN was cooled to 0 ° C. and HCl(1N, 0.106 mL, 0.106 mmol) was added. The reaction was stirred at 0° C. for 1 hr. The reaction was diluted with EtOAc, washed with NaHCO$_3$, and brine. The solution was dried over MgSO$_4$, filtered, and concentrated. The residue was chromatographed over silica gel (1:1 hexane/ethyl acetate) and recrystallized from ethyl acetate/hexane to yield 0.041 g of the title compound, ketone IIIc (80%).

ESIHRMS (M+Na calcd. for C$_{47}$H$_{49}$O$_{14}$N Na: 874.3051. Found: 874.3014.

IR(KBr) 3448(br.), 2955, 1732, 1654, 1374, 1242 cm$^{-1}$.

$^1$H NMR (CDCl$_3$, 300 MHz) δ 8.15(d, J=6.0 Hz, 2H), 7.70(d, J=6.9 Hz, 2H), 7.64–7.34(m, 11H), 6.90(d, J=9.3 Hz, 1H), 6.39(s, 1H), 6.25(t, J=8.4 Hz, 1H), 5.80(d, J=9.0, 1H), 5.70(d, J=7.5, 1H), 4.79(s, 2H), 4.42(d, J=8.4 Hz, 1H), 4.35(d, J=8.4 Hz, 1H), 4.11(d, J=7.5 Hz, 1H), 3.47(d, J=5.4 Hz, 1H), 3.11(d, J=13.8 Hz, 1H), 2.50-2.42(m, 4H), 2.33–2.25(m, 3H), 2.20(s, 3H), 1.84(s, 4H), 1.66(s, 3H), 1.22(s, 3H), 1.12(s, 3H).

$^{13}$C NMR (CDCl$_3$, 75.5 MHz) δ 202.4,202.1, 172.9, 170.9, 169.6, 167.3, 166.8, 141.0, 137.9, 133.9, 133.6, 133.3, 132.0, 130.3, 129.1, 129.0, 128.9, 128.7, 128.4, 127.1, 127.0, 85.0, 84.4, 78.7, 78.2, 76.6, 75.2, 73.7, 73.1, 72.2, 55.0, 53.0, 51.0,45.2,43.0,36.1, 26.2,22.6,21.6,20.7, 16.3, 14.5.

Example 3

Preparation of 7-deoxy-6-β-hydroxypaclitaxel [IIId] -(Scheme V)

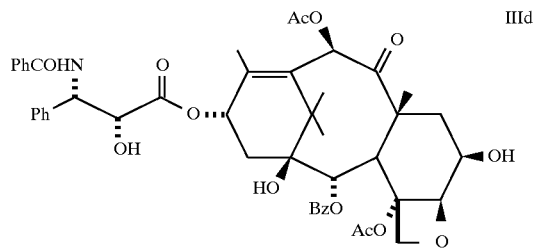

IIId

The ketone IIa (0.084 g, 0.087 mmol) was dissolved in 3 mL of ETOH and cooled to 0° C. NaBH$_4$ (0.003 g, 0.087 mmol) was added as a solid and the reaction was stirred at 0° C. for 1 hr.. The reaction was quenched with H$_2$O, diluted with ethyl acetate and washed with brine. The solution was dried over MgSO$_4$ and concentrated. The residue was chromatographed over silica gel (1:1 hexane/ethyl acetate) to give 0.0693 g of 6-β alcohol 12a (82%).

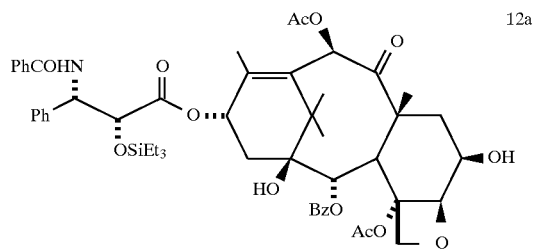

12a

ESILRMS M-H calcd. for C$_{53}$H$_{64}$O$_{14}$N Si: 966. Found: 966

IR(KBr) 3442(br.), 2956, 1732, 1664, 1485, 1372, 1242 cm$^{-1}$.

$^1$H NMR (CDCl$_3$, 300 MHz) δ 8.14(d, J=7.2 Hz, 2H), 7.71(d, J=76.9 Hz, H), 7.54–7.29(m, 11H), 7.07(d, J=7.1 Hz, 1H), 6.44(s, 1H), 6.24(br. t., 1H), 5.69(d, J=7.8 Hz, 1H), 4.97(d, J=8.4 Hz, 1H), 4.65(s, 1H), 4.46(d, J=8.1 Hz, 1H), 4.24(m, 2H), 3.65(d, J=6.9 Hz, 1H), 2.75(br. d., 1H), 2.53(s, 3H), 2.45–2.35(m, 1H), 2.22–2.10(m, 5H), 1.86(s, 3H), 1.77(s, 3H), 1.19(s, 3H), 1.10(s, 3H), 0.78(m, 9H), 0.41(m, 6H).

The silyl ether 12a (0.063 mg, 0.065 mmol) was dissolved in 5 mL of CH$_3$CN and cooled to 0° C. and HCl(1N, 0.130 mL, 0.130 mmol) was added and the reaction was stirred for 1 hr.. The solution was diluted with ethyl acetate and washed with NaHCO$_3$, brine. The solution was dried over MgSO$_4$, filtered, and concentrated. The residue was chromatographed over silica gel (1:2 hexane/ethyl acetate) to give 0.053 g of the title compound, diol IIId (95%).

ESILRMS M-Hcalcd for C$_{47}$H$_{50}$O$_{14}$N:852. Found: 852.

Anal. calcd. for C$_{47}$H$_{51}$O$_{14}$N: C, 66.11; H, 6.02; N, 1.64. Found: C, 65.92; H, 6.14; N, 1.54.

IR(KBr) 3442(br.), 2945, 1732, 1648, 1372, 1242 cm$^{-1}$.

$^1$H NMR (CDCl$_3$, 300 MHz) δ 8.14(d, J=6.9, 2H), 7.71(d, J=7.2 Hz, 2H), 7.61–7.25(m, 11H), 6.93(d, J=9.0 Hz, 1H), 6.41(s, 1H), 6.19(br. t., 1H), 5.78(d, J=6.3 Hz, 1H), 5.68(d, J=7.2Hz, 1H), 4.95(d, J=8.4 Hz, 1H), 4.78(m, 1H), 4.46(d, J=8.4 Hz, 1H), 4.22(m,2H), 3.66(d, J=6.9 Hz, 1H), 3.47(d, J=5.4 Hz, 1H), 2.72(br. d., 1H), 2.39(s, 3H), 2.35–2.24(m, 2H), 2.19(s, 3H), 2.18–2.11(m,1H), 1.85–1.76(m, 2H), 1.78 (s, 3H), 1.56 (s,3H), 1.18(s, 3H), 1.10(s, 3H).

Example 4

Preparation of 7-deoxy-6β-hydroxy-6α-methylpaclitaxel [IIIe]-(Scheme VI)

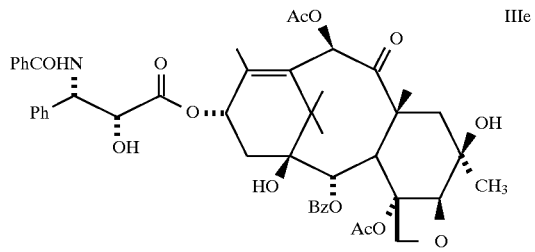

A solution of the silyl ketone 11a (0.100 g, 0.104 mmol) was dissolved in CH$_2$Cl$_2$, cooled to −20° C., and Me$_3$Al (2.0M in hexane, 0.415 mL, 0.830 mmol) was added via syringe. The reaction was stirred at −15° to −20° C. for 30 min. The reaction was quenched with H$_2$O, diluted with EtOAc, washed with brine. The solution was dried over MgSO$_4$, filtered, and concentrated. The residue was chromatographed over silica gel (1:1 hexane/ethyl acetate) to yield 0.090 g of tertiary alcohol 13a (88%).

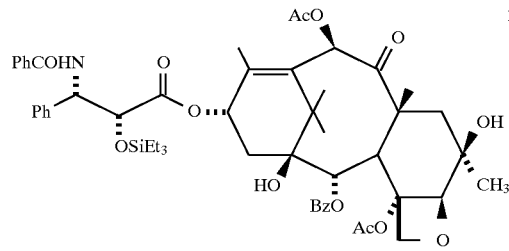

ESILRMS M+NH$_4$$^+$ calcd for C$_{54}$H$_{71}$O$_{14}$N$_2$Si: 999. Found: 999.

Anal. calcd. for C$_{54}$H$_{67}$O$_{14}$NSi-H$_2$O: C, 64.84; H, 6.95; N, 1.40. Found: C, 64.56; H, 6.86; N, 1.21.

IR(KBr) 3444(br.), 2956, 1734, 1244, 710 cm$^{-1}$.

$^1$H NMR (CDCl$_3$, 300 MHz) d 8.14(d, J=6.9 Hz, 2H), 7.71(d, J=6.9 Hz, 2H), 7.60–7.31(m, 11H), 7.08(d, J=9.0 Hz, 1H), 6.42(s, 1H), 6.24(br. t., 1H), 5.73–5.64(m, 2H), 4.67(d, J=2.1 Hz, 1H), 4.57(s, 1H), 4.43(d, J=8.1 Hz, 1H), 4.30(d, J=8.7 Hz, 1H), 3.73(d, J=6.9 Hz, 1H), 3.22(s, 1H), 2.55(s, 3H), 2.43–2.35(m, 1H), 2.19(s, 3H), 2.14–2.06(m, 1H), 1.98 - 1.81 (m, 2H), 1.88(s, 3H), 1.75(s, 3H), 1.27(s, 3H), 1.19(s, 3H), 1.09(s, 3H), 0.78(m, 9H), 0.44(m, 6H).

The 2' protected tertiary alcohol 13a (0.077 g, 0.078 mmol) was dissolved in 3 mL of THF and was shaken with Bu$_4$NF (0.086 mL, 1.0M in THF, 0.086 mmol) diluted with ethyl acetate and washed with H$_2$O, brine. The solution was dried over MgSO$_4$, filtered, and concentrated. The residue was chromatographed over silica gel (1:1 hexane/ethyl acetate) to give 0.0572 g of tertiary alcohol IIIe (85%).

ESIHRMS M+Na calcd for C$_{48}$H$_{53}$O$_{14}$N Na: 890.3364. Found: 890.3389.

IR(KBr) 3442(br.), 1736, 1648, 1372, 1242 cm$^{-1}$. $^1$H NMR (CDCl$_3$, 300 MHz) δ 8.14(d, J=7.2 Hz, 2H), 7.71(d, J=7.2 Hz, 2H), 7.61–7.33(m, 11H), 6.94(d, J=9.0 Hz, 1H), 6.39(s, 1H), 6.19(br. t., 1H), 5.78(d, J=8.7 Hz, 1H), 5.68(d, J=6.9 Hz, 1H), 4.77(m, 1H), 4.55(s, 1H), 4.42(d, J=8.4 Hz, 1H), 4.28(d, J=8.4 Hz, 1H), 3.71(d, J=6.9 Hz, 1 H), 3.44(d, J=5.1 Hz, H), 3.19(s, 1H), 2.41(s, 3H), 2.35–2.25(m, 2H), 2.20(s, 3H), 1.81–1.74(m, 2H), 1.77 (s, 3H), 1.74 (s, 3H), 1.25(s, 3H), 1.18(s, 3H), 1.10(s, 3H).

$^{13}$C NMR (CDCl$_3$, 75.5 Hz) δ 205.0, 172.6, 170.1, 166.9, 140.0, 137.8, 133.6, 131.9, 130.1, 129.1, 128.9, 128.7, 128.6, 128.2, 126.9, 126.8,89.9,81.7, 78.8, 75.4, 73.7, 73.0, 72.1, 68.2, 54.8, 53.5, 48.6, 44.5, 42.7, 35.8, 31.3, 26.1, 22.5,21.3,20.7, 16.2, 14.3.

Example 5

Preparation of 3'desphenyl-3'-(2-furyl)-3'N-debenzoyi-3'N-tbutoxycarbonya6α-hydroxy-7-deoy-paclitaxel [IIIf]-(Scheme VII)

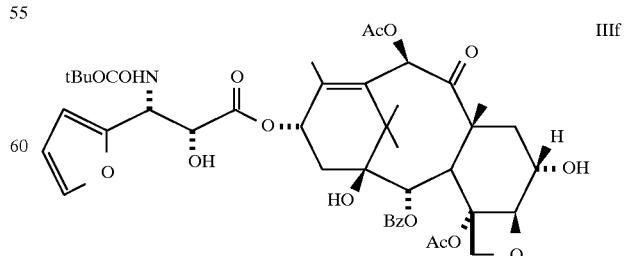

A solution of diol 6a (6.07 g, 7.10 mmol) in methylene chloride was treated with tetrabutylammonium borohydride (3.02 g, 11.73 mmol) at ambient temperature for 60 hours. Acetic acid (25.66 mL) was added slowly to the reaction mixture and the solution concentrated. The residue was chromatographed over silica (4:1 hexane/ethyl acetate) to give 3.27 g of baccatin derivative 14a.

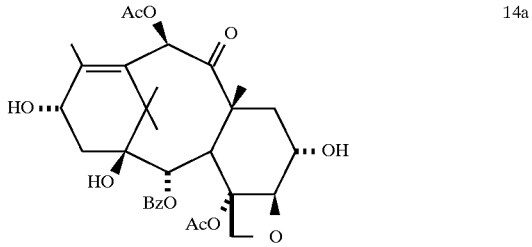

The baccatin derivative 14a (3.27 g, 5.58 mmol) was dissolved in DMF with imidazole (1.18 g, 17.30 mmol). TESCl (2.81 mL, 16.74 mmol) was added and the reaction was stirred for 1 hr. The reaction was diluted with EtOAc, and washed with $H_2O$ then brine. The solution was dried over $MgSO_4$, filtered, and concentrated. The residue was chromatographed over silica gel (2:1 hexane/ethyl acetate) to give 2.592 g (52%) of the monosilylated baccatin 15a.

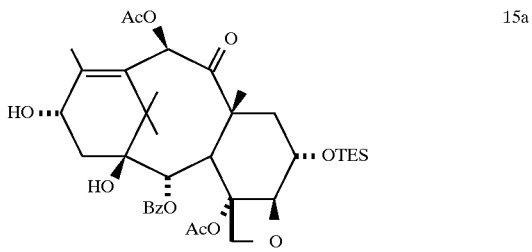

ESILRMS M-H calcd. for $C_{37}H_{51}O_{11}Si$: 699. Found: 699.
IR(KBr) 3528(br.), 2956, 1714, 1454, 1372, 1230 $cm^{-1}$.
$^1$H NMR ($CDCl_3$, 300 MHz) d 8.07(d, J=8.57 Hz, 2H); 7.61–7.43(m, 3H); 6.44(s, 1H); 5.57(d, J=7.2 Hz, 1H); 4.84(br. s, 1H); 4.70(d, J=1.84 Hz, 1H); 4.23(ab q, J=16.9, 8.36 Hz, 2H); 4.16–4.10(m, 1H); 3.95(d, J=7.3 Hz, 1H); 2.36–2.14(m, 9H); 2.05(s, 4H); 1.71–1.56(m, 5H); 1.06(s, 6H); 0.88(m, 9H); 0.52(m, 6H).

The monosilyl baccatin derivative 15a (1.00 g, 1.43 mmol) was dissolved in THF and cooled to −78° C. n-BuLi (0.72 mL, 2.5 M in hexanes, 1.79 mmol) was added and the reaction was stirred at −78° C. for 10 min. The lactam 16a (i)-cis- 3-4-(2-furyl)-3-triethylsilyoxy-N-t-butoxycarbonylazetidin-2-one (2.10 g, 5.71 mmol) was added as a solution in THF. The reaction was warmed to 0° C. and stirred at 0° C. for 50 min. The reaction was diluted with EtOAc, washed with $NH_4Cl$ and then brine. The solution was dried over $MgSO_4$, filtered, and concentrated. The residue was chromatographed over silica gel (20% ethyl acetate/ hexane) to give 1.319 g of product 9c (86%).

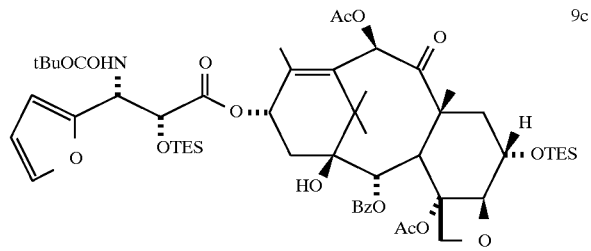

The bis silyl ether 9c (1.32 g, 1.149 mmol) was dissolved in $CH_3CN$ and cooled to 0OC. Aqueous HCl (4.6 mL, 1N, 4.6 mmol) was added and the reaction was stirred at 0° C. for 45 min. The reaction was diluted with EtOAc, washed with NaHCO3, and then brine. The solution was dried over MgSO4, filtered, and concentratedin vacuo. The residue was chromatographed over silica gel(1:1 hexane/ EtOAc). The reaction was not complete. The starting material was resubjected to the reaction conditions. The reaction was diluted with EtOAc, washed with $NaHCO_3$, and then brine. The solution was dried over MgSO4, filtered, and concentrated. The residue was chromatographed over silica gel(1:1 EtOAc/hexane) to give 945 mg of diol IIIf (91%)
ESILRMS M+H calcd. for $C_{43}H_{54}O_{16}N$: 840. Found: 840.
IR(KBr) 3446(br.), 2980, 1716, 1496, 1452, 1370, 1242 $cm^{-1}$.
Anal. calcd. for $C_{43}H_{55}O_{17}N \cdot H_2O$: C, 60.20; H, 6.23; N, 1.63. Found: C, 60.43; H, 6.28; N, 1.55.
$^1$H NMR ($CDCl_3$, 300MHz) d 8.11(d, J=7.1 Hz, 2H); 7.63-7.41(m, 4H); 6.46(s, 1H); 6.38(m, 1H); 6.31(m, 1H); 6.22(t, J=9.2, 1H); 5.66(d, J=7.0 Hz, 1H); 5.34(d, J=8.0 Hz, 1H); 5.20(d, J=10.1 Hz, 1H); 4.79(s, 1H); 4.70 (s, 1H); 4.30(d, J=7.9 Hz, 1H); 4.14–4.08(m, 2H); 3.80(d, J=7.1 Hz, 1H); 3.24(br. s, 1H); 2.42–2.38(m, 4H); $^2$.33–2.22(m, 4H); $^2$.10-1.96(m, 2H); 1.89(s, 3H); 1.71(s, 4H); 1.33(s, 9H); 1.22(s, 3H); 1.13(s, 3H).

Example 6

Preparation of [IIIg]

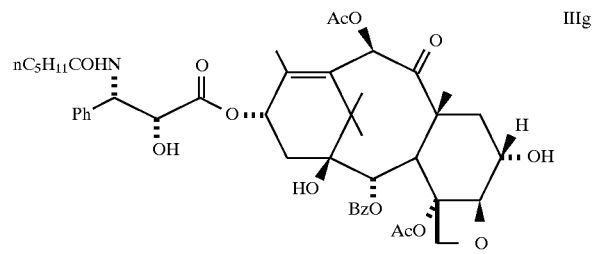

The monosilyl baccatin derivative 15a (1.400 g, 2.00 mmol) was dissolved in THF and cooled to −78° C. n-BuLi (1.0 mL, 2.5 M in hexanes, 2.5 mmol) was added and the reaction was stirred at −780° C. for 15 min. Lactam 16b (3R, $^4$S)-N-hexanoyl-4-phenyl-3-triethylsilyoxyazetidin-2-one (3.00 g, 8.00 mmol) was added as a solution in THF. The reaction was warmed to 0° C., stirred at 0° C. for 50 min., diluted with EtOAc, washed with $NH_4Cl$, and then brine. The solution was dried over $MgSO_4$, filtered, and concentrated in vacuo. The residue was chromatographed over silica gel (20% ethyl acetate/hexane) to give 1.615 g of bis silyl ether 9d (75%).

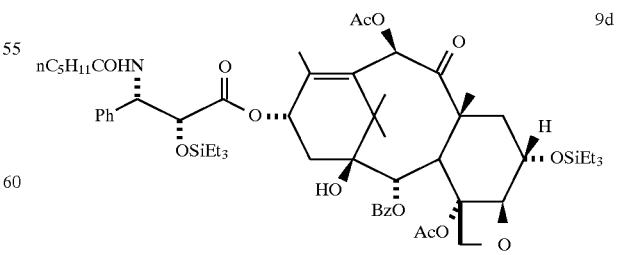

ESILRMS M-H calcd. for $C_{58}H_{84}O_{14}N Si_2$: 1074. Found: 1074.
IR(KBr) 3440(br.), 2958, 1736, 1682, 1496, 1372, 1244 cm7$^{-1}$.

Anal. calcd. for $C_{58}H_{85}O_{14}N$ $Si_2$: C, 64.71; H, 7.96; N, 1.30. Found: C, 64.48; H, 7.97; N, 1.30.

$^1$H NMR (CDC13, 300 MHz) d 8.11(d, J=7.03 Hz, 2 H); 7.60–7.46(m, 3H); 7.37-7.22(m, 5H); 6.44(s, 1H); 6.34(d, J=9.13 Hz, 1H); 6.23(t, J=9.01 Hz, 1H); 5.63(d, J=7.41 Hz, 1H); 5.54(d, J=7.76 Hz, 1H); 4.68(d, J=2.08 Hz, 1H); 4.55(d, J=1.97 Hz, 1H); 4.25(s, 2H); 4.14(m, 1H);

3.87(d, J=7.35 Hz, 1H); 2.50(s, 3H); 2.45–2.37(m, 1H); 2.22–2.09(m, 7H); 1.91(s, 3H); 1.75(s, 1H); 1.71–1.64(m, 4H); 1.61(s, 2H); 1.53(br. t, 2H); 1.24–1.18(m, 8H); 1.11(s, 3H); 0.91–0.86(m, 9H); 0.81–0.73(m, 9H);

0.57–0.49(m, 6H); 0.47–0.25(m, 6H).

The bis silyl ether 9d (1.652 g, 1.54 mmol) was dissolved in $CH_3CN$ and cooled to 0° C. HCl (3.18 mL, 1.0N, 3.18 mmol) was added and the reaction was stirred at 0° C. for 75 min., diluted with EtOAc, washed with $NaHCO_3$, and then brine. The solution was dried over $MgSO_4$, filtered, and concentrated. The residue was chromatographed over silica gel (60% ethyl acetate/ hexane) to give 1.144 g (87%) of diol IIIg .

ESILRMS M+H calcd. for $C_{46}H_{58}O_{14}N$: 848. Found: 848.

IR(KBr) 3420(br.), 2956, 1726, 1636, 1452, 1372, 1246 $cm^{-1}$.

Anal. calcd. for C46 H57–014 N: C, 65.16; H, 6.78; N, 1.65. Found: C, 64.82; H, 6.71; N, 1.54.

$^1$H NMR (CDC13, 300 MHz) d 8.11(d, J=7.36 Hz, 2H); 7.63–7.58(m, 1H); 7.52–7.47(m, 2H); 7.39–7.31(m, 5H); 6.43(s, 1H); 6.19–6.13(m, 2H); 5.64(d, J=7.3 Hz, 1H); 5.56(d, J=6.66 Hz, 1H); 4.76(s, 1H); 4.64(m, 1H); 4.28(d, J=8.42 Hz, 1H); 4.13(d, J=8.27 Hz, 1H); 4.08(m, 1H); 3.75(d, J=7.35 Hz, 1H); 3.38(d, J=5.37 Hz, 1H); 2.41–2.27 (m, 4H); 2.24–2.14(m, 6H); 2.04–1.97(m, 2H); 1.88–1.82 (m, 4H); 1.73–1.70(m, 4H); 1.55(s, 4H); 1.22–1.20(m, 6H); 1.12(s, 2H); 0.83–0.78(m, 3H).

Example 7

Preparation of [IIIh]-(Scheme VII)

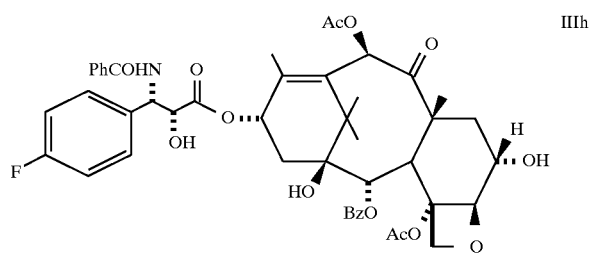

The monosilyl baccatin derivative 15a (0.800 g, 1.14 mmol) was dissolved in THF and cooled to –78° C. n-BuLi (0.571 mL, 2.5M in hexanes, 1.428 mmol) was added and the reaction was stirred at –78° C. for 15 min. Lactam 16c (±)-cis-N-benzoyl-4-(4-fluorophenyl)-3-triethylsilyoxyazetidin-2-one (2.42 g, 6.065 mmol) was added as a solution in THF. The reaction was stirred at –78° C. for 30 min. and at 0° C. for 30 min.. The reaction was diluted with EtOAc, washed with $NH_4Cl$, and then brine. The solution was dried over $MgSO_4$ filtered, and concentrated. The residue was chromatographed over silica gel (20% ethyl acetate/ hexane) to give 1.094 g of bis silyl ether 9e (75%).

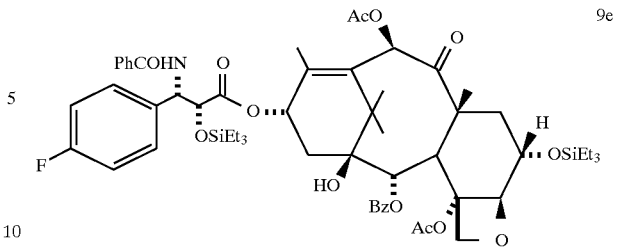

ESILRMS M+H calcd. for $C_{59}H_{79}O_{14}N$ $Si_2F$: 1100. Found: 1100.

IR(KBr) 3444(br.), 2956, 1736, 1671, 1482, 1370, 1232 $cm^{-1}$.

Anal. calcd. for $C_{59}H_{78}O_{14}N$ $Si_2F$: C, 64.40; H, 7.14; N, 1.27. Found: C, 64.14; H, 6.95; N, 1.31.

$^1$H NMR (CDCl$_3$, 300 MHz) d 8.11(d, J=6.99 Hz, 2H); 7.72–7.70(m, 2H); 7.61–7.30(m, 9H); 7.08(t, J=8.85 Hz, 2H); 6.43(s, lH); 6.25(t, =8.83 Hz, 1H); 5.67–5.61(m, 2H); 4.68(d, J=2.09 Hz, 1H); 4.61(d, J=1.97 Hz, 1H); 4.264.24(m, 2H); 4.14(m, 1H); 3.88(d, J=7.33 Hz, 1H);

2.52(s, 3H); 2.46–2.37(m, 1H); 2.23–2.11(m, 4H); 1.91(s, 3H); 1.71–1.65(m, 6H); 1.25–1.17(m, 3H); 1.09(s, 3H); 0.93–0.77(m, 18H); 0.59–0.32(m, 12H).

The bis silyl ether 9e (0.419 g, 0.381 mmol) was dissolved in $CH_3CN$ and cooled to 0° C. HCl (0.152 mL, 1.0N, 0.152 mmol) was added and the reaction was stirred at 0° C. for 1 hr.. Diluted with EtOAc, washed with $NaHCO_3$, brine. The solution was dried over $MgSO_4$, fitered, and concentrated. The residue was chromatographed over silica gel (2:1 ethyl acetate/hexane) to give 0.289 g (72%) of diol IIIh and approximately 15% of the other sidechain diastereomer.

ESILRMS M-H calcd. for $C_{47}H_{49}O_{14}N$ F: 870. Found: 870.

IR(KBr) 3427(br.), 2948, 1729, 1652, 1511, 1371, 1237 $cm^{-1}$.

Anal. calcd. for $C_{47}H_{50}O_{14}N$ F: C, 64.74; H, 5.78; N, 1.61. Found: C, 64.52; H, 5.95; N, 1.53.

$^1$H NMR (CDCl$_3$, 300 MHz) d 8.13(d, J=8.22 Hz, 2H); 7.69(d, J=8.14 Hz, 2H); 7.60–7.34(m, 9H); 7.09(t, J=8.51 Hz, 2H); 6.90(d, J=9 Hz, 1H); 6.42(s, 1H); 6.21(t, J=9 Hz, 1H); 5.76(d, J=7.4 Hz, 1H); 5.64(d, J=7.3 Hz, 1H); 4.77–4.74(m, 2H); 4.29(d, J=8.67 Hz, 1H); 4.14(d, J=8.43 Hz, 1H); 4.134.07(m, 1H); 3.77(d, J=7.16 Hz, 1H); 3.57(br. s, 1H); 2.40(s, 3H); 2.35–2.19(m, 5H); 2.05–1.97(m, 3H); 1.81(s, 3H); 1.70(s, 4H); 1.89(s, 3H); 1.11(s, 3H).

Example 8

Preparation of [IIIi]-(Scheme VIII)

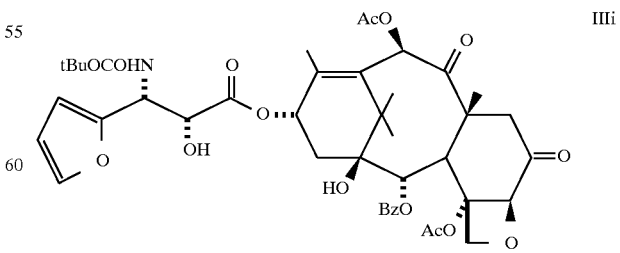

Diol IIIf (0.945 g, 1.125 mmol) and NMO (0.276 g, 2.36 inmol) were dissolved in $CH_2Cl_2$ and stirred over 4 Å molecular sieves for 10 min. and cooled to 0° C. before TP?AP (0.040 g, 0.1125 mmol) was added. The reaction was stirred for 1 hrs. at 0° C. The reaction was filtered through celite and concentrated. The residue was dissolved in EtOAc, washed with Na$_2$S$_2$O$_3$, brine. The solution was dried over MgSO$_4$, filtered and concentrated. The residue was chromatographed over silica gel(1:1 hexanel EtOAc) to give 0.327 g of ketone IIIi (35%).

ESILRMS M-H calcd. for C$_{43}$H$_{50}$O$_{16}$N: 836. Found: 836.

IR(KBr) 3450(br.), 2982, 1730, 1498, 1370, 1240 cm$^{-1}$.

Anal. calcd. for C$_{43}$H$_{51}$O$_{16}$N: C, 61.64; H, 6.13; N, 1.67. Found: C, 61.59; H, 6.24; N, 1.69.

$^1$H NMR (CDCl$_3$, 300 MHz) d 8.10(d, J=8.48 Hz, 214); 7.62–7.58(m, 1H); 7.52–7.47(m, 214); 7.41(br. s, 114); 6.42(s, 114); 6.38–6.36(m, 1H); 6.32–6.31(m, 1H); 6.24(t, 1=9 Hz, 114); 5.69(d, J=7.15 Hz, 1H); 5.27(ab q, J=40.25, 9.89 Hz, 2H); 4.80(s, 1H); 4.72–4.70(m, 1H); 4.36(ab q, J=28.4,8.36 Hz, 2H); 4.14(d, J=7.12 Hz, 1H); 3.25(d, J=5.49 Hz, 1H); 3.12(d, J=13.92 Hz, 1H); 2.46–2.41(m, 4H); 2.37–2.29(m, 2H); 2.21(s, 3H); 1.90(s, 3H); 1.69–1.65(m, 4H); 1.32(s, 9H); 1.24(s, 3H); 1.13(s, 3H).

Example 9

Preparation of [IIIj]-Scheme VIII

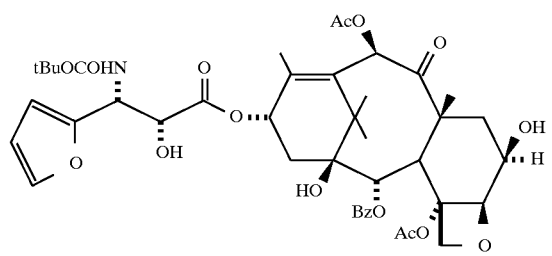

The ketone IIIi (0.300 g, 0.358 mmol) was dissolved in EtOH and cooled to 0° C. before NaBH$_4$ (0.014 g, 0.358 mmol) was added as a solid. The reaction was stirred at 0° C. for 1 hr. The reaction was diluted with EtOAc, washed with H$_2$O, and then brine. The solution was dried over MgSO$_4$, filtered, and concentrated. The residue was chromatographed over silica gel(1:1 hexane/EtOAc) to give 0.237 g of diol IIIj (79%).

ESILRMS M-H calcd. for C$_{43}$H$_{52}$O$_{16}$N: 838. Found: 838.

IR(KBr) 3450(br.), 2980, 1716, 1498, 1452, 1370, 1240 cm$^{-1}$.

Anal. calcd. for C$_{43}$H$_{53}$O$_{16}$N: C, 61.49; H, 6.36; N, 1.67. Found: C, 61.34; H, 6.42; N, 1.57.

$^1$H NMR (CDCl$_3$ 300 MHz) d 8.12 (d, J=7.19 Hz, 2H); 7.61–7.58(m, 1H); 7.51–7.48(m, 2H); 7.40(s, 1H); 6.45(s, 1H), 6.35(m, 1H); 6.31(m, 1H); 6.23(t, J=9 Hz, 1H); 5.69–5.67(d, J=7.2 Hz, 1H); 5.27(ab q, J=40.25, 9.89 Hz, 2H); 4.96(d, J=8.51 Hz, 1H); 4.68(m, 1H); 4.34(d, J=8.4 Hz, 1H); 4.21(m, 2H); 3.67(d, J=7.2 Hz, 1H); 3.27(br. d, 1H); 2.72(br. d, 1H); 2.40–2.20(m, 9H); 1.85(s, 3H); 1.76(s, 3H); 1.68(s, 3H); 1.44–1.40(m, 1H); 1.32(s, 9H); 1.21(s, 3H); 1.12(s, 3H).

Example 10

Preparation of [IIIk]-(Scheme IX, V)

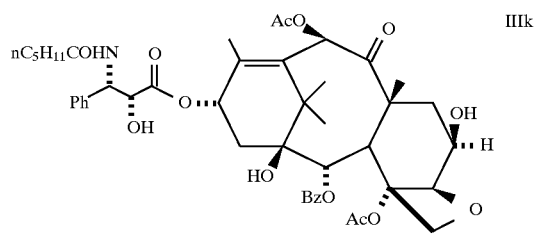

Bis silyl ether 9d (0.917 g, 0.853 mmol) was dissolved in MeOH and cooled to 0° C. A catalytic amount of Dowex H$^+$ resin was added and the reaction was stirred at 0° C. for 3 hr. The reaction was filtered, and concentrated. The residue was chromatographed over silica gel(1.5:1 hexane/ EtOAc) to give 0.729 g of monodeprotected alcohol 6b (89%).

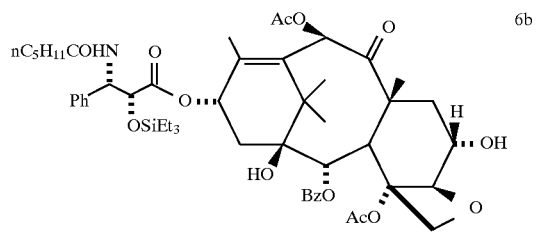

ESILRMS M+H calcd. for C$_{52}$H$_{72}$O$_{14}$N Si: 962. Found: 962.

IR(KBr) 3438(br.), 2956, 1733, 1496, 1371, 1243 cm$^{-1}$.
Anal. calcd. for C$_{52}$H$_{71}$O$_{14}$N Si: C, 64.91; H, 7.44; N, 1.46. Found: C, 64.76; H, 7.33; N,.1.50.

$^1$H NMR (CDCl$_3$, 300 MHz) d 8.11(d, J=8.52 Hz, 2H); 7.59–7.56(m, 1H); 7.53–7.48(m, 2H); 7.37–7.22(m, 5H); 6.46(s, 1H); 6.33(d, J=9 Hz, 1H); 6.22(br. t, 1H); 5.65(d, J=7.3 Hz, 1 H); 5.53(d, J=8.1 Hz, 1 H); 4.79(s, 1H); 4.55(d, J=2.05 Hz, 1H); 4.30(d, J=8.13 Hz, 1H); 4.15(d, J=8.1 Hz,1H); 4.12(m, 1H); 3.78(d, J=7.45 Hz, 1H); 2.50(s, 3H); 2.45–2.37(m, 2H); 2.22–2.17(m, 7H); 2.03(d, J=9 Hz, 2H); 1.89(s, 4H); 1.71(s, 4H); 1.24–1.12(m, 12H); 0.79–0.74(m, 9H); 0.45–0.29(m, 6H).

The monosilyl alcohol 6b (0.720 g, 0.749 mmol) and NMO (0.184 g, 1.573 mmol) were dissolved in CH$_2$Cl$_2$ and stirred over 4 Å molecular sieves for 15 min. before TPAP (0.026 g, 0.075 mmol) was added. The reaction was stirred for 1 hr. The reaction was filtered through celite and concentrated. The residue was dissolved in EtOAc, washed with Na$_2$S$_2$O$_3$, brine. The solution was dried over MgSO$_4$, filtered and concentrated. The residue was chromatographed over silica gel(2:1 hexane/EtOAc) to give 0.648 g of silyl ketone lb (90%).

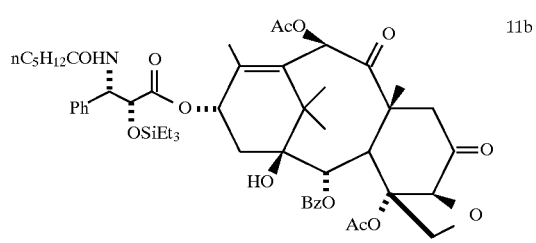

ESILRMS M+H calcd. for C$_{52}$H$_{70}$O$_{14}$N Si: 960. Found: 960.
IR(film) 3437(br.), 2956, 1729, 1676 1241, 752, 709 cm$^{-1}$.

Anal. calcd. for C₅₂H₆₉O₁₄N Si: C, 65.05; H, 7.24; N, 1.46. Found: C, 64.83; H, 7.23; N, 1.49.

¹H NMR (CDCl₃, 300 MHz) d 8.12(d, J=8.55 Hz, 2H); ⁷.62–7.57(m, 1H); 7.53–7.48(m, 2H); ⁷.39–7.23(m, 5H); 6.43(s, 1H); 6.35(d, J=9.4 Hz, 1H); 6.25(t, J=9.2 Hz, 1H); 5.71(d, J=7.3 Hz, 1H); 5.57(d, J=7.8 Hz, 1H); 4.81(s,1H); 4.58(d, J=2.1 Hz, 1H); 4.38(dd, J=17, 8.4 Hz, 2H); 4.12(d, J=7.4 Hz, 1H); 3.14(d, J=13.6 Hz, 1H); 2.55(s, 3H); 2.47–2.17(m, 8H); 1.91–1.87(m, 4H); 1.67(s, 3H); 1.62(s, 3H); 1.53(m, 2H); 1.26(s, 3H); 1.23–1.18(m, 4H); 1.12(s, 3H); 0.81–0.74(m, 9H); 0.49–0.28(m, 6H).

Silyl ketone 11b (0.300 g, 0.313 mmol) was dissolved in EtOH and cooled to 0° C. before NaBH₄ (0.012 g, 0.313 mmol) was added as a solid. The reaction was stirred at 0° C. for 1 hr.. The reaction was diluted with EtOAc, washed with H₂O, brine. The solution was dried over MgSO₄, filtered, and concentrated. The residue was chromatographed over silica gel(2:1 hexane/EtOAc). The residue was dissolved in CH₃CN and cooled to 0° C. HCl (0.626 mL, 1N, 0.626 mmol) was added and the reaction was stirred at 0° C. for 1 hr.. The reaction was diluted with EtOAc, washed NaHCO₃, brine. The solution was dried over MgSO₄, filtered, and concentrated. The residue was chromatographed over silica gel(1:2 hexane/EtOAc) to give 0.216 g of diol IIIk (82%).

ESILRMS M-H calcd. for C₄₆H₅₆O₁₄N: 846. Found: 846.

IR(KBr) 3440(br.), 2931, 1735, 1637, 1452, 1371, 1239 cm⁻¹.

Anal. calcd. for C₄₆H₅₇O₁₄N: C, 65.16; H, 6.78; N, 1.65. Found: C, 64.86; H, 6.72; N, 1.56.

¹H NMR (CDCl₃, 300 MHz) d 8.10(d, J=8.5 Hz, 2H); 7.60–7.29(m, 8H); 6.41(s, 1H); 6.17–6.14(m, 2H); 5.66(d, J=7.1 Hz, 1H); 5.54(d, J=9.0 Hz, 1H); 4.91(d, J=8.3 Hz, 1H); 4.65–4.62(m, 1H); 4.41(d, J=8.2 Hz, 1H); 4.20(d, J=8.2 Hz, 2H); 3.62(d, J=7.0 Hz, 1H); 2.70(d, J=7.5 Hz, 1H); 2.34(s, 3H); 2.31–2.13(m, 8H); 1.84–1.75(m, 8H); 1.52(m, 2H); 1.25–1.17(m, 8H); 1.09(s, 3H); 0.79(m, 3H).

Example 11

Preparation of [III 1]-(Scheme IX, V)

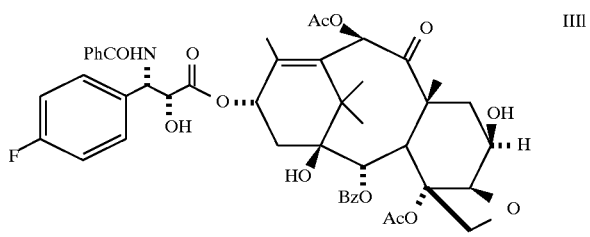

Bis silyl ether 9e (0.575 g, 0.523 mmol) was dissolved in MeOH and cooled to 0OC. A catalytic amount of Dowex H⁺ resin was added and the reaction was stirred at 0° C. for 3 hr.. The reaction was filtered, and concentrated. The residue was chromatographed over silica gel(2:1 hexane/EtOAc) to give 0.313 g of monosilyl ether 6c (61%).

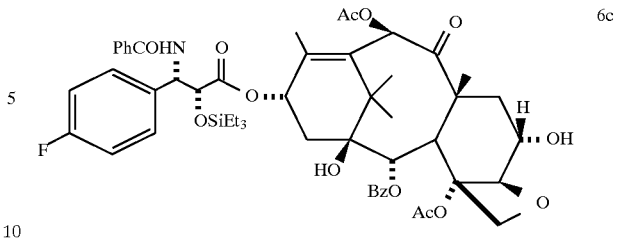

ESILRMS M+H calcd. for C₅₃H₆₅O₁₄N Si F: 986. Found: 986.

IR(KBr) 3439(br.), 2955, 1732, 1510, 1483, 1371, 1235 cm⁻¹.

Anal. calcd. for C₅₃H₆₄O₁₄N Si F: C, 64.55; H, 6.54; N, 1.42. Found: C, 64.54; H, 6.46; N, 1.49.

¹H NMR (CDCl₃, 300 MHz) d 8.12(d, J=6.9 Hz, 2H); 7.70(d, J=7.16 4 Hz, 2H); 7.60–7.29(m, 8H); 7.07(m, 3H); 6.45(s, 1H); 6.23(br. t, 1H); 5.64(d, J=7.5 Hz, 1H); 4.80(s, 1H); 4.61(s, 1H); 4.31(d, J=8.3 Hz, 1H); 4.17–4.10(m, 2H); 3.79–3.72(m, 2H); 2.52(s, 3H); 2.50–2.37(m, 2H); 2.19(s, 3H); 2.01(d, J=8.9 Hz, 2H); 1.89(s, 3H); 1.85–1.81(m, 1H); 1.71–1.67(m, 4H); 1.19(s, 3H); 1.10(s, 3H); 0.83–0.78(m, 9H); 0.51–0.36(m, 6H).

The monosilyl alcohol 6c (0.305 g, 0.309 mmol) and NMO (0.076 g, 0.649 mmol) were dissolved in CH₂Cl₂ and stirred over 4 Å molecular sieves for 10 min. before TPAP (0.011 g, 0.03 mmol) was added. The reaction was stirred for 1 hr. The reaction was filtered through celite and concentrated. The residue was dissolved in EtOAc, washed with Na₂S₂O₃, brine. The solution was dried over MgSO₄, filtered and concentrated. The residue was chromatographed over silica gel(2:1 hexane/EtC)Ac) to give 0.266 g of 11c (87%).

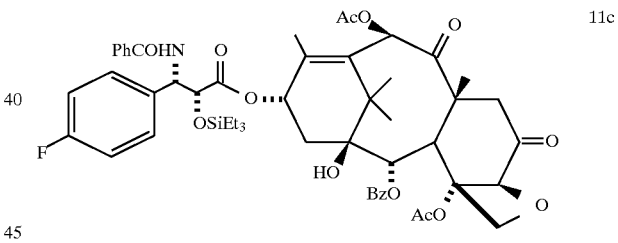

ESILRMS M-H calcd. for C₅₃H₆₁O₁₄N Si F: 982. Found: 982.

IR(filn) 3439(br.), 2956, 1728, 1679 1371, 1241 cm⁻¹.

Anal. calcd. for C₅₃H₆₂O₁₄N Si F: C, 64.68; H, 6.35; N, 1.42. Found: C, 64.66; H, 7.08; N, 1.49.

¹H NMR (CDCl₃, 300 MHz) d 8.13(d, J=7.1 Hz, 2H); 7.71(d, J=7.1 Hz, 2H); 7.58–7.45(m, 4H); 7.40–7.28(m, 4H); 7.11–7.05(m, 3H); 6.42(s, 1H); 6.27(t, J=9.2 Hz, 1H); 5.71–5.69(m, 2H); 4.81(s, 1H); 4.64(m, 1H); 4.39(ab q, J=19.4, 8.19 Hz, 2H); 4.12(d, J=7.3 Hz, 1H); 3.13(d, J=14.2 Hz, 1H); 2.57(s, 3H); 2.49–2.40(m, 2H); 2.19–2.10(m, 4H); 1.91(s, 3H); 1.74(s, 1H); 1.66(s, 3H); 1.21(s, 3H); 1.11(s, 3H); 0.84–0.79(m, 9H); 0.55–0.37(m, 6H).

The silyl ketone 11c (0.260 g, 0.264 mmol) was dissolved in EtOH and cooled to 0° C. before NaBH₄ (0.010 g, 0.264 mmol) was added as a solid. The reaction was stirred at 0° C. for 1 hr. The reaction was diluted with EtOAc, washed with H₂O, brine. The solution was dried over MgSO₄, filtered and concentrated. The residue was dissolved in CH₃CN and cooled to 0° C. HCl (0.528 mL, 1N, 0.528 mmol) was added and the reaction was stirred at 0° C. for 1 hr. The reaction was diluted with EtOAc, washed Na HCO₃, brine. The solution was dried over MgSO₄, filtered, and concentrated. The residue was chromatographed over silica gel(1:2 hexane/EtOAc) to give 0.182 g (79%) of diol III 1.

ESILRMS M-H calcd. for $C_{47}H_{49}O_{14}N$ F: 870. Found: 870.

IR(KBr) 3430(br.), 2944, 1731, 1652, 1510, 1485, 1371, 1238 cm$^{-1}$.

Anal. calcd. for $C_{47}H_{50}O_{14}N$ F: C, 64.74; H, 5.78; N, 1.61. Found: C, 64.44; H, 5.77; N, 1.55.

$^1$H NMR (CDCl₃, 300 MHz) d 8.13(d, J=8.5 Hz, 2H); 7.68(d, J=8.2 Hz, 21H); 7.60–7.34(m, 9H); 7.07(t, J=8.6 Hz, 2H); 6.91(d, J=8.9 Hz, 1H); 6.40(s, 1H); 6.19(br. t, 1H); 5.74(d, J=8.7 Hz, 1H); 5.67(d, J=7.1 Hz, 1H); 4.93(d, J=8.1 Hz, 1H); 4.72(m, 1H); 4.43(d, J=7.8 Hz, 1H); 4.21(d, J=8.4 Hz, 2H); 3.64(d, J=6.9 Hz, 1H); 3.53(d, J=4.73 Hz, 1H); 2.69(d, J=7.3 Hz, 1H); 2.38–2.32(m, 4H); 2.28–2.15(m, 4H); 1.85–1.74(m, 8H); 1.20(s, 3H); 1.09(s, 3H).

Example 12

Preparation of [IIIm] (Scheme X)

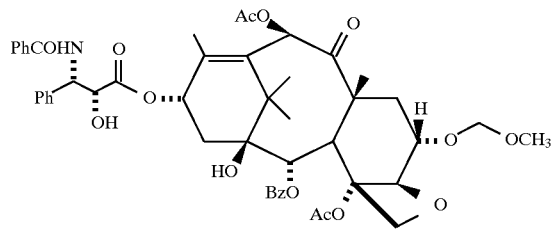

IIIm

The alcohol 6a (0.513 g, 0.531 mmol) was dissolved in THF (10 mL) and cooled to −50° C. LiHMDS (0.637 mL, 1M in THF, 0.637 mmol) was added and the reaction was stirred at −50° C. for 15 min.. MOMBr (0.052 mL, 0.637 mmol) was added and the reaction was allowed to warm to 0° C. over 30 min. and and stirred at 0° C. for 1 hr. The reaction was quenched with H20, and extracted with ethyl acetate. The solution was dried over MgSO₄, filtered, and concentrated. The residue was chromatographed over silica gel (1:1 hexane/ethyl acetate) to give 0.476 g of methoxymethyl ether 17a (89%).

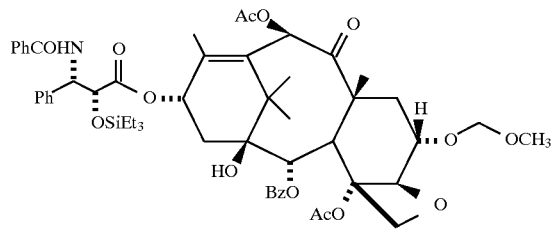

17a

ESILRMS M+H calcd. for $C_{55}H_{70}O_{15}N$ Si: 1012. Found: 1012.

IR(KBr) 3442(br.), 2954, 1734, 1670, 1483, 1371, 1232 cm$^{-1}$.

Anal calcd. for $C_{55}H_{69}O_{15}N$ Si: C, 65.26; H, 6.87; N, 1.38. Found: C, 65.58; H, 6.88; N, 1.43.

$^1$H NMR (CDCl₃, 300 MHz) d 8.15(d, J=8.5 Hz, 2H), 7.71(d, J=8.5 Hz, 2H); 7.61–7.28(m, 11H); 7.11(d, J=8.1 Hz, 1H); 6.48(s, 1H); 6.24(br. t, 1H); 5.69(t, J=9.9 Hz, 2H); 4.86(s, 1H); 4.774.63(m, 3H); 4.30(ab q, J=20.5, 8.5 Hz, 2H); 4.14(m, 1H); 3.90(d, J=7.0 Hz, 1H); 3.32(s, 3H); 2.55–2.42(m, 4H); 2.21–2.10(m, 5H); 2.04–1.91(m, 4H); 1.25–1.12(m, 6H); 0.93–0.77(m, 9H); 0.50–0.37(m, 6H).

The silyl ether 17a (0.446 g, 0.441 mmol) was dissolved in 15 mL of CH₃CN and cooled to 0° C. HCl (0.882 mL, 1N, 0.882 mmol) was added and the reaction was stirred at 0° C. for 1 hr.. The reaction was quenched with NaHCO₃(sat), and extracted with ethyl acetate. The solution was dried over MgSO₄, filtered, and concentrated. The residue was chromatographed over silica gel (1:2 hexane/ethyl acetate) to give 0.344 g of methoxymethyl ether IIIm (87%).

ESILRMS M+H calcd. for $C_{49}H_{56}O_{15}N$: 898. Found: 898.

IR(KBr) 3428(br.), 2948, 1734, 1664, 1485, 1371, 1232 cm$^{-1}$.

Anal calcd. for $C_{49}H_{55}O_{15}N$: C, 65.54; H. 6.17; N, 1.56. Found: C, 65.37; H,6.06; N, 1.37.

$^1$H NMR (CDCl₃, 300 MHz) d 8.15(d, J=8.5 Hz, 2H); 7.71(d, J=8.5 Hz, 2H); 7.63–7.34(m, 11H); 6.94(d, J=9.5 Hz, 1H); 6.43(s, 1H); 6.21(t, J=9.9 Hz, 1H); 5.80(dd, J=17.8, 9.9 Hz, 1H); 5.64(d, J=7.8 Hz, 1H); 4.81(s, 1H); 4.77–4.74(m, 1H); 4.60(ab q, J=8.9, 6.8 Hz, 2H); 4.27(ab q, J=18.8, 8.4 Hz, 2H); 4.14–4.07(m, 1H); 3.87(d, J=7.8 Hz, 1H); 3.41(d, J=5.8 Hz, 1H); 3.30(s, 3H); $^2$.46–2.37(m, 4H); 2.28–2.10(m, 5H); 1.93–1.87(m, 1H); 1.81(s, 3H); 1.71–1.68(m, 4H); 1.20(s, 3H); 1.12(s, 3H).

Example 13

Preparation of [IIIn]-(Scheme XI)

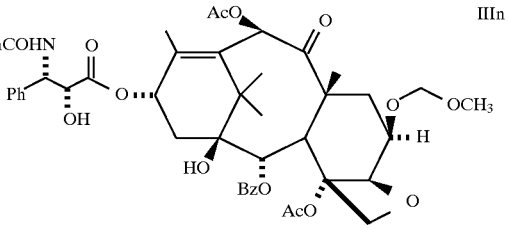

IIIn

The alcohol 7a (0.472 g, 0.488 mmol) was dissolved in THF (6 mL) and cooled to −50° C. LiHMDS (0.586 mL, 1M in THF, 0.586 mmol) was added and the reaction was stirred at −50° C. for 15 min.. MOMBr (0.048 mL, 0.586 mmol) was added and the reaction was allowed to warm to 0° C. over 30 min. and and stirred at 0° C. for 1 hr. The reaction was quenched with H₂O, and extracted with ethyl acetate. The solution was dried over MgSO₄, filtered, and concentrated. The residue was chromatographed over silica gel (1:1 hexane/ethyl acetate) to give 0.451 g of monosilyl methoxymethyl ether 18a (91%).

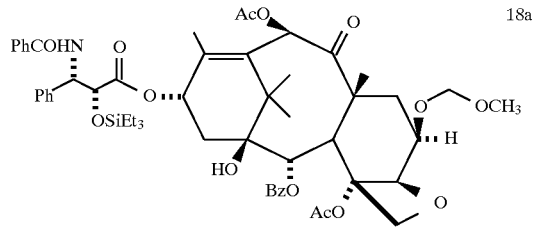

18a

ESILRMS M+H calcd. for $C_{55}H_{70}O_{15}N$ Si: 1012. Found: 1012.

IR(KBr) 3445(br.), 2955, 1731, 1670, 1483, 1371, 1242 cm$^{-1}$.

Anal calcd. for $C_{55}H_{69}O_{15}N$ Si: C, 65.26; H, 6.87; N, 1.38. Found: C,65.23; H, 6.88; N, 1.33.

$^1$H NMR (CDC13, 300 MHz) d 8.15(d, J=7.0 Hz, 2H); 7.73(d, J=7.1 Hz, 2H); 7.60–7.29(m, 11H); 7.10(d, J=8.9 Hz,

1H); 6.47(s, 1H); 6.23(br. t, 1H); 5.74–5.68(m, 2H); 5.02(d, J=7.5 Hz, 1H); 4.67(m, 1H); 4.57(ab q, J=11.4, 6.9 Hz, 2H); 4.30–4.17(m, 2H); 3.64(d, J=7.0 Hz, 1H); 3.32(s, 3H); 2.52(s, 3H); 2.38–2.10(m, 6H); 1.88–1.84(m, 6H); 1.76(s, 1H); 1.20(s, 3H); 1.12(s, 4H); 0.8340.78(m, 9H); 0.50–0.35 (m, 6H).

The silyl ether 18a (0.428 g, 0.423 mmol) was dissolved in 10 mL of CH$_3$CN and cooled to 0° C. HCl (0.846 mL, 1N, 0.846 mmol) was added and the reaction was stirred at 0° C. for 1 hr. The reaction was quenched with NaHCO3(sat), and extracted with ethyl acetate. The solution was dried over MgSO4, filtered, and concentrated. The residue was chromatographed over silica gel (1:2 hexane/ethyl acetate) to give 0.343 g of methoxymethyl ether IIIn (90%).

ESILRMS M+H calcd. for $C_{49}H_{56}O_{15}N$: 898. Found: 898.

IR(KBr) 3436(br.), 2930, 1730, 1664, 1485, 1371, 1241 cm$^{-1}$.

Anal calcd. for $C_{49}H_{55}O_{15}N$: C, 65.54; H. 6.17; N, 1.56. Found: C, 65.52; H,6.22; N, 1.52.

$^1$H NMR (CDCl$_3$, 300 MHz) d 8.15(d, J=7.1 Hz, 2H); 7.73(d, J=8.5 Hz, 2H); 7.64–7.32(m, 11H); 6.98(d, J=8.8 Hz, 1H); 6.44(s, 1H); 6.18(t, J=9.5 Hz, 1H); 5.78(d, J=8.5 Hz, 1H); 5.71(d, J=7.25 Hz, 1H); 5.00(d, J=7.05 Hz, 1H); 4.79–4.76(m, 1H); 4.56(ab q, J=11.5,6.9 Hz, 2H); 4.39(d, J=7.7 Hz, 1H); 4.26–4.21(m, 1H); 4.16(d, J=7.8 Hz, 1H); 3.64(d, J=7.2 Hz, 1H); 3.51(d, J=4.9 Hz, 1H); 3.33–3.30(m, 3H); 2.38(s, 3H); 2.33–2.22(m, 6H); 1.88(s, 4H); 1.79–1.71 (m, 4H); 1.20(s, 3H); 1.13(s, 3H).

Example 14

Preparation of [19a] [20a]-(Scheme XII)

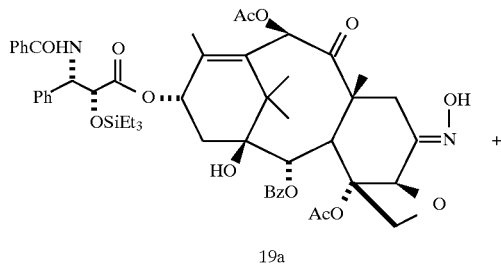

19a

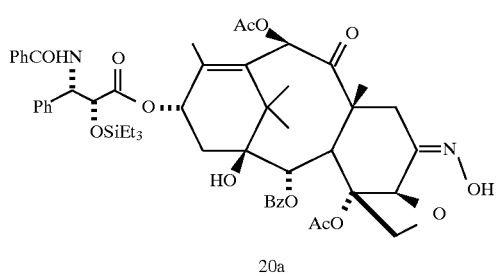

20a

The silyl ketone 11a (0.251 g, 0.260 mmol) was dissolved in 5 mL of MeOH along with NH$_2$OH-HCl (0.112 g, 1.613 mmol) and DABCO (0.050 g, 0.442 mmol) with heating and allowed to stir for 20 minutes. The reaction was diluted with ethyl acetate and washed with H$_2$O twice and brine. The solution was dried over MgSO$_4$, filtered, and concentrated. The residue was chromatographed over silica gel (20% CH$_3$CN/CH$_2$Cl$_2$) to give 0.116 g (46%) of oxime 19a; and 0.0876 g (34%) of oxime 20a.

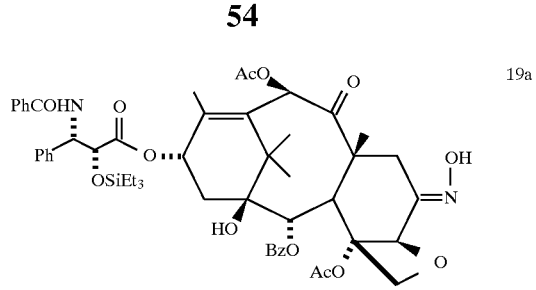

19a

ESILRMS M+H calcd. for $C_{53}H_{65}O_{14}N_2$Si: 981. Found: 981.

Anal. calcd. for $C_{53}H_{64}O_{14}N_2$Si-H$_2$O: C, 63.71; H, 6.46; N, 2.80. Found: C, 63.65; H, 6.48; N, 2.74.

IR(KBr) 3440(br.), 2956, 1734, 1236, 710 cm$^{-1}$.

$^1$H NMR (CDCl$_3$, 300 MHz) 8 8.14(d, J=7.2 Hz, 2H), 7.71(d, J=76.9 Hz, 2H), 7.54–7.29(m, 11H), 7.07(d, J=7.1 Hz, 1H), 6.43 (s, 1H), 6.24(br. t., 1H), 5.70 (m, 2H), 5.56 (d, J=8.4 Hz, 1H), 4.65(s, 1H), 4.46(d, J=8.1 Hz, 1H), 4.30 (d, J=8.1 Hz, 1H), 3.88 (d, J=6.9 Hz, 1H), 2.90 (br. d., 1H), 2.53(s, 3H), 2.45–2.35(m, 2H), 2.22 (s, 3H), 2.15 (m, 1H), 1.89(s, 1H), 1.70(s, 3H), 1.19(s, 3H), 1.12 (s, 3H), 0.78(m, 9H), 0.41(m, 6H).

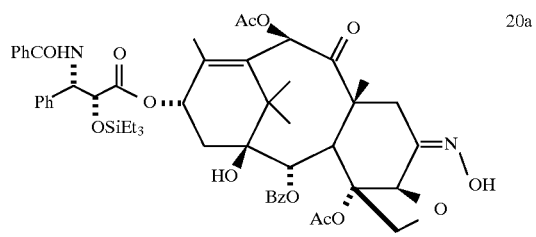

20a

ESILRMS M+H calcd. for $C_{53}H_{65}O_{14}N_2$ Si: 981. Found: 981

Anal. calcd. for $C_{53}H_{64}O_{14}N_2$Si-2H$_2$O: C, 62.58; H, 6.74; N, 2.75. Found: C, 63.01; H, 6.40; N, 2.75.

IR(KBr) 3438(br.), 2956, 1734, 1238, 710 cm$^{-1}$.

$^1$H NMR (CDCl$_3$, 300 MHz) 8 8.14(d, J=7.2 Hz, 2H), 7.71(d, J=76.9 Hz, H), 7.54–7.29(m, 11H), 7.07(d, J=7.1 Hz, 1H), 6.52 (s, 1H), 6.24(br. t., 1H), 5.70 (m, 2H), 5.16 (d, J=8.4 Hz, 1H), 4.65(s, 1H), 4.46(d, J=8.1 Hz, 1H), 4.24(d, J=8.1 Hz, 1H), 3.88 (d, J=6.9 Hz, 1H), 3.10 (br. d., 1H), 2.53(s, 3H), 2.45–2.35(m, 2H), 2.22 (s, 3H),2.15 (m, 1H), 1.89(s, 1H), 1.81 (s, 3H), 1.19(s, 3H), 1.12 (s, 3H), 0.78(m, 9H), 0.41(m, 6H).

Example 15

Preparation of [IIIo]-(Scheme XII)

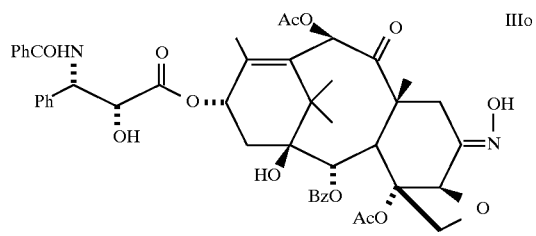

IIIo

The silyl oxime 19a (0.080 g, 0.0816 mmol) was dissolved in 3 mL of THF and was shaken with Bu$_4$NF (1.0M in THF, 0.090 mL, 0.090 mmol), diluted with ethyl acetate, and washed with brine. The solution was dried over MgSO$_4$ and concentrated. The residue was chromatographed over silica gel (20% CH$_3$CN/CH$_2$Cl$_2$) to give 0.060 g of oxime IIIo (85%).

ESILRMS M+H calcd. for C47H51O14N2: 867. Found: 867.

IR(KBr) 3430(br.), 1734, 1648, 1372, 1240 cm$^{-1}$.

$^1$H NMR (CDCl$_3$, 300 MHz) δ 8.14(d, J=7.2 Hz, 2H), 7.71(d, J=7.2 Hz, 2H), 7.64–7.31(m, 12H), 6.96(d, J=8.4 Hz, 1H), 6.49(s, 1H), 6.19(t, J=8.7 Hz, 1H), 5.78–5.71(m, 2H), 5.14(s, 1H), 4.77–4.75(m, 1H), 4.41(d, J=8.1 Hz, 1H), 4.23(d, J=8.7 Hz, 1H), 3.85(d, J=7.2 Hz, 1H), 3.51(d, J=5.4 Hz, 1H), 3.51(br. s., 1H), 3.07(d, J=16.8 Hz, 1H), 2.49–2.30 (m, 2H), 2.38 (s, 3H), 2.21(s, 3H), 1.89 (s, 1H), 1.81(s, 3H), 1.78(s, 3H), 1.55(m, 1H), 1.20 (s, 3H), 1.14(s, 3H).

$^{13}$C NMR (DMSO, 300 MHz) δ 204.4, 172.6, 170.4, 169.1, 166.2, 165.3, 150.3, 140.4, 139.2, 134.5, 133.6, 132.7, 131.3, 129.8, 129.6, 128.8, 128.3, 127.4, 81.3, 79.1, 76.9, 75.9, 75.1, 73.6, 69.3, 56.3, 52.5, 44.9, 42.6, 41.3, 34.9, 25.9, 22.4, 21.4, 20.5, 14.8, 13.9.

Example 16

Preparation of [IIIg]-(Scheme XII)

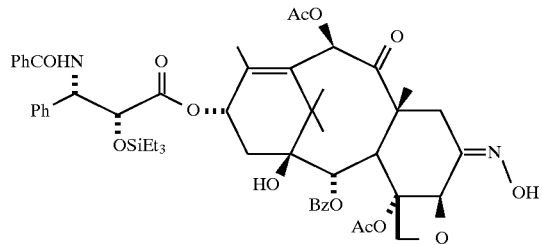

The silyl oxime 20a (0.110 g, 0.112 mmol) was dissolved in 3 mL of THF and was shaken with Bu$_4$NF (1.0M in THF, 0.123 mL, 0.123 mmol) diluted with ethyl acetate and washed with brine. The solution was dried over MgSO$_4$ and concentrated. The solid was recrystallized from acetone/hexane to give 0.060 g of oxime IIIp (62%).

ESILRMS M+H calcd. for C$_{47}$H$_5$O$_{14}$N2: 867. Found: 867.

IR(KBr) 3432(br.), 1716, 1646, 1372, 1238 cm$^{-1}$.

$^1$H NMR (CDCl$_3$, 300 MHz) δ 8.14(d, J=7.2 Hz, 2H), 7.70(d, J=7.2 Hz, 21H), 7.63–7.33(m, 11H), 6.95(d, J=9.0 Hz, 1H), 6.40(s, 1H), 6.20(t, J=8.7 Hz, 1H), 5.77(d, J=9.6 Hz, 1H), 5.67(d, J=7.5 Hz, 1H), 5.53(s, 1H), 4.77(m, 1H), 4.37(d, J=8.4 Hz, 1H), 4.28(d, J=8.7 Hz, 1H), 3.87(d, J=7.8 Hz, 1H), 3.54(d, J=5.1 Hz, 1H), 2.84(d, J=14.4 Hz, 1H), 2.44–2.23(m, 4H), 2.39 (s, 3H), 2.20(s, 3H), 1.93(s, 1H), 1.80(s, 3H), 1.69(s, 3H), 1.20(s, 3H), 1.13(s, 3H).

$^{13}$C NMR (DMSO, 300 MHz) δ204.3, 172.6, 170.2, 169.2, 166.2, 165.4, 149.8, 140.2, 139.2, 134.4, 133.5, 132.7, 131.3, 129.8, 129.6, 128.8, 128.3, 127.4, 127.4, 82.3, 80.1, 76.8, 75.4, 75.2, 73.6, 73.2, 69.3, 56.3, 51.7, 43.4, 42.6, 35.6, 34.8, 30.7, 25.8, 22.2, 21.4, 20.5, 15.4, 13.8.

Example 17

Preparation of [9f]-(Scheme VII)

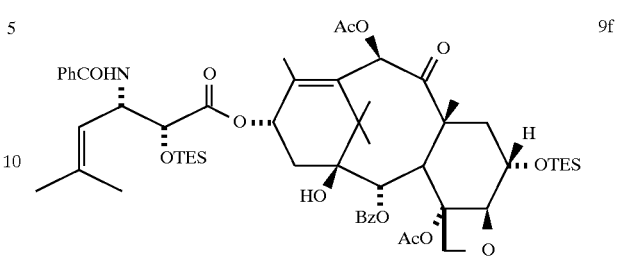

The monosilyl baccatin derivative 15a (1.261 g, 1.80 mmol) was dissolved in THF (15 mL) and cooled to −50° C. n-BuLi (1.35 mL, 1.6M in hexanes, 2.16 mmol) was added and the reaction was stirred at -500C for 15 min. The lactam 16c(3R,4S)-N-benzoyllisobutenyl-3-triethylsilyloxyazetidin-2-one(3.24 g, 9.00 mmol) was added as a solution in THF(10 mL) and the flask was rinsed with THF (2×5 mL). The reaction was warmed to 0° C. and stirred at 0° C. for 45 min.. The reaction was diluted with EtOAc, washed with NH$_4$Cl, H$_2$O, brine. The solution was dried over MgSO$_4$, filtered, and concentrated. The residue was chromatographed twice over silica gel (30% ethyl acetate/hexane) to give 1.718 g of product (90%) as a 4:1 mixture of diastereomers.

ESILRMS M+H calcd. for C$_{57}$H$_{82}$O$_{14}$N Si$_2$: 1060. Found: 1060.

IR(KBr) 3445(br.), 2956, 2878, 1737, 1717, 1271 cm$^{-1}$.

Anal calcd. for C$_{57}$H$_{81}$O$_{14}$N Si$_2$: C, 64.56; H, 7.70; N, 1.32. Found: C, 64.69; H, 7.74; N, 1.36.

$^1$H NMR (CDCl$_3$, 300 MHz) d 8.12(d, J=7.2 Hz, 2H), 7.72–7.33(m, 8H), 6.63(d, J=8.5 Hz, 1H), 6.44(s, 1H), 6.11(t, J=8.7 Hz, 1H), 5.63(d, J=7.6 Hz, 1H), 5.39(d, J=8.9 Hz, 1H), 5.30–5.24(m, 1H), 4.69(d, J=2.1 Hz, 1H), 4.39(d, J=2.4 Hz, 1H), 4.33–4.25(m, 2H), 4.16(m, 1H), 3.90(d, J=7.5 Hz, 1H), 2.53–2.38(m, 4H), 2.32–2.14(m, 8H), 2.04–1.87(m, 7H), 1.78(s, 4H), 1.18(s, 3H), 1.10(s, 3H), 1.03–0.97(m, 9H), 0.95–0.87(m, 9H), 0.71–0.63(m, 6H), 0.58–0.50(m, 6H).

Example 18

Preparation of [IIIq]-(Scheme IX,X)

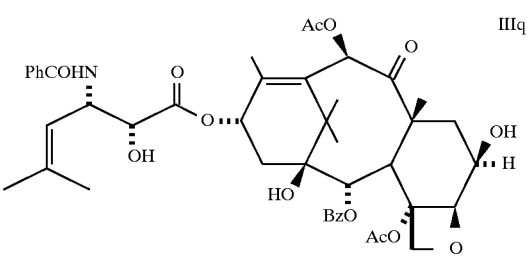

The bis silyl ether 9f (0.44 g, 0.415 mmol) was dissolved in MeOH and a catalytic amount of Dowex H$^+$ was added. The reaction was allowed to stir overnight. The reaction was diluted with EtOAc, washed with NaHCO$_3$(sat.), H$_2$O, brine. The solution was dried over MgSO$_4$, filtered, concentrated. The residue was chromatographed over silica gel (1:1 ethyl acetate/hexane) to give 0.151 g of product (39%).

ESILRMS M+H calcd. for $C_{51}H_{68}O_{14}N$ Si: 946. Found: 946.

IR(KBr) 3445(br.), 2956, 1733, 1452, 1271, 1242 cm$^{-1}$.

Anal calcd. for $C_{51}H_{67}O_{14}N$ Si: C, 64.74; H, 7.14; N, 1.48. Found: C, 64.60; H, 7.25; N, 1.37.

$^1$H NMR (CDCl$_3$, 300 MHz) d 8.12(d, J=7.2 Hz, 2H), 7.72–7.57(m, 3H), 7.49–7.33(m, 5H), 6.51–6.45(m, 2H), 6.10(t, J=9.1 Hz, 1H), 5.65(d, J=7.5 Hz, 1H), 5.38(d, J=8.9 Hz, 1H), 5.29–5.23(m, 1H), 4.80(s, 1H), 4.39(d, J=2.6 Hz, 1H), 4.30(d, J=8.4 Hz, 1H), 4.19(d, J=8.3 Hz, 1H), 4.14–4.03(m, 2H), 3.81(d, J=7.4 Hz, 1H), 2.53–2.40(m, 4H), 2.34–2.23(m, 2H), 2.20–2.18(m, 6H), 2.03–1.86(m, 7H), 1.78(s, 4H), 1.17(s, 3H), 1.08(s, 3H), 1.02–0.89(m, 9H), 0.71–0.56(m, 6H).

The alcohol 6d ( 1.162 g, 1.23 mmol), was dissolved in CH$_2$Cl$_2$(30 mL). 4 Å sieves were added and the reaction was stirred for 15 minutes. NMO(0.302g, 2.583 mmol) was added and the reaction was stirred for 1.5 hrs. The reaction mixture was filtered through Celite and concentrated. The residue was chromatographed over silica gel (1:1 ethyl acetate/hexane) to give 1.046g of product (90%).

ESILRMS M+H calcd. for $C_{51}H_{66}O_{14}N$ Si: 944. Found: 944.

IR(KBr) 3442(br.), 2957, 1732, 1485, 1269, 1241 cm$^{-1}$.

Anal calcd. for $C_{51}H_{65}O_{14}N$ Si: C, 64.88; H, 6.94; N, 1.48. Found: C, 64.99; H, 7.00; N, 1.40.

$^1$H NMR (CDCl$_3$, 300 MHz) d 8.12(d, J=8.5 Hz, 2H), 7.72–7.59(m, 3H), 7.50–7.34(m, 5H), 6.64(d, J=8.3 Hz, 1H), 6.47(s, 1H), 6.15(t, J=8.8 Hz, 1H), 5.71(d, J=7.5 Hz, 1H), 5.41(d, J=8.9 Hz, 1H), 5.32–5.25(m, 1H), 4.82(s, 1H), 4.44–4.35(m, 3H), 4.16(d, J=6.8 Hz, 1H), 3.16(d, J=13.7 Hz, 1H), 2.56–2.44(m, 4H), 2.40–2.21(m, 4H), 2.20–2.14(m, 4H), 1.91(s, 3H), 1.87(s, 3H), 1.79(s, 4H), 1.21(s, 3H), 1.12(s, 3H), 1.04–0.93(m, 9H), 0.72–0.56(m, 6H).

The ketone 11d(1.05 g, 1.11 mmol) was dissolved in EtOH(40 mL) and cooled to 0° C. NaBH$_4$(0.042 g, 1.11 mmol) was added and the reaction was stirred at 0° C. for 25 minutes. The reaction was diluted withEtOAc, quenched with H20, washed with brine. The solution was dried over MgSO4, filtered, concentrated. The residue was chromatographed over silica gel (75% diethyl ether/hexane) to give 0.811 g of 2'-O-triethylsilyl protected product (77%).

ESILRMS M+H calcd. for $C_{51}H_{68}O_{14}N$ Si: 946. Found: 946.

IR(KBr) 3446(br.), 2957, 1732, 1660, 1272, 1240 cm$^{-1}$.

Anal calcd. for $C_{51}H_{69}O_{15}N$ Si: C, 63.53; H, 7.21; N, 1.45. Found: C, 63.95; H, 7.26; N, 1.21.

$^1$H NMR (CDCl$_3$, 300 MHz) d 8.13(d, J=8.5 Hz, 2H), 7.72–7.59(m, 3H), 7.50–7.33(m, 5H), 6.49–6.41(m, 2H), 6.10(t, J=9.2 Hz, 1H), 5.70(d, J=7.2 Hz, 1H), 5.39(d, J=8.8 Hz, 1H), 5.31–5.22(m, 1H), 4.97(d, J=8.5 Hz, 1H), 4.45(d, J=8.2 Hz, 1H), 4.39(m, 1H), 4.28–4.23(m, 2H), 3.69(d, J=7.1 Hz, 1H), 2.76(br. s, 1H), 2.50–2.40(m, 4H), 2.35–2.16 (m, 5H), 2.08–2.04(m, 1H), 1.95(s, 3H), 1.87(s, 3H), 1.86–1.78(m, 7H), 1.18(s, 3H), 1.11(s, 3H), 1.02–0.93(m, 9H), 0.71–0.54(m, 6H).

The silyl ether(0.775 g, 0.819 mmol) was dissolved in CH$_3$CN (45 mL), and cooled to 0° C. HCl (1.64 mL, 1N, 1.64 mmol) was added and the reaction was stirred at 0° C. for 45 minutes. The reaction was diluted with EtOAc, washed with NaHCO$_3$(sat.), H$_2$O, brine. The solution was dried over MgSO$_4$, filtered, and concentrated. The residue was chromatographed over silica gel( 30% CH$_3$CN/CH$_2$Cl$_2$) to give 0.5004 g of IIIq (73%).

ESILRMS M+H calcd. for $C_{45}H_{54}O_{14}N$: 832. Found: 832.

IR(KBr) 3442(br.), 2938, 1732, 1646, 1271, 1240 cm$^{-1}$.

Anal calcd. for $C_{45}H_{53}O_{14}N$: C, 64.97; H, 6.42; N, 1.68. Found: C, 64.85; H, 6.50; N, 1.53.

$^1$H NMR (CDCl$_3$, 300 MHz) d 8.13(d, J=8.5 Hz, 2H), 7.70–7.59(m, 3H), 7.51–7.45(m, 3H), 7.40–7.35(m, 2H), 6.44–6.41(m, 2H), 6.17(t, J=7.6 Hz, 1H), 5.70(d, J=7.2 Hz, 1H), 5.45(d, J=9.0 Hz, 1H), 5.30–5.23(m, 1H), 4.97(d, J=8.3 Hz, 1H), 4.45(d, J=8.3 Hz, 1H), 4.35(s, 1H), 4.24(d, J=8.1 Hz, 2H), 3.68(d, J=7.0 Hz, 1H), 3.58(br. s, 1H), 2.74(br. s, 1H), 2.41–2.38(m, 5H), 2.25–2.14(m, 5H), 1.86(s, 3H), 1.82–1.78(m, 10H), 1.22(s, 3H), 1.12(s, 3H).

Example 19

Preparation of [9g]-(Scheme VII)

The monosilyl baccatin derivative 15a (1.001 g, 1.43 mmol) was dissolved in THF (10 mL) and cooled to –50° C. n-BuLi (1.0725 mL, 1.6M in hexanes, 1.716 mmol) was added and the reaction was stirred at –50° C. for 15 min. The lactam 16d (3R,4S)-N-t-butoxycarbamoyl4-phenyl-3-triethylsilyoxyazetidin-2-one (1.188 g, 3.146 mmol) was added as a solution in THF (10 mL) and the flask was rinsed with THF (2×5 mL). The reaction was warmed to 0° C. over 30 minutes and stirred at 0° C. for 30 minutes. The reaction was diluted with EtOAc, washed with NH$_4$Cl, H$_2$O, brine. The solution was dried over MgSO$_4$, filtered, and concentrated. The residue was chromatographed over silica gel (10% to 20% ethyl acetate/ hexane) to give 1.453 g of product 9 g (94%).

ESILRMS M+H calcd. for C$_{57}$H$_{84}$O$_{15}$N Si$_2$: 1078. Found: 1078.

IR(KBr) 3448(br.), 2957, 1717, 1494, 1369, 1243 cm$^{-1}$.

Anal calcd. for C$_{57}$H$_{83}$O$_{15}$N Si$_2$: C, 63.48; H, 7.76; N, 1.30. Found: C, 63.54; H, 7.56; N, 1.33.

$^1$H NMR (CDCl$_3$, 300 MHz) d 8.11(d, J=8.5 Hz, 2H), 7.60–7.25(m, 8H), 6.46(s, 1H), 6.29(t, J=8.3 Hz, 1H), 5.63 (d, J=7.4 Hz, 1H), 5.49(d, J=9.4 Hz, 1H), 5.29(d, J=8.9 Hz, 1H), 4.71(d, J=2.1 Hz, 1H), 4.53(s, 1H), 4.26(ab q, J=12.4, 8.6 Hz, 2H), 4.16(m, 1H), 3.90(d, J=7.3 Hz, 1H), 2.53(s, 3H), 2.46–2.35(m, 1H), 2.24–2.16(m, 5H), 2.03(s, 3H), 1.72–1.62(m, 5H), 1.28(s, 9H), 1.25(s, 3H), 1.12(s, 3H), 0.98–0.87(m, 9H), 0.83–0.72(m, 9H), 0.62–0.50(m, 6H), 0.45–0.29(m, 6H).

Example 20

Preparation of [IIIr]-(Scheme IX.X)

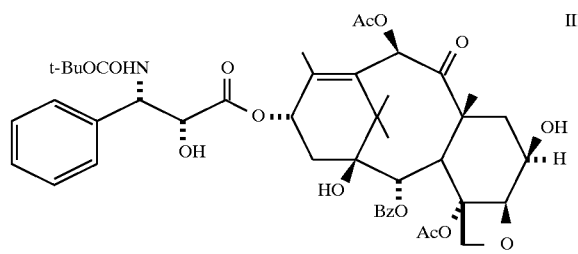

The bis silyl ether 9 g (1.431 g, 1.328 mmol) was dissolved in MeOH(60 mL) and cooled to 0° C. and a catalytic amount of Dowex H$^+$ was added. The reaction was stirred at 0° C. for five hours. The reaction was diluted with EtOAc, washed with NaHCO$_3$(sat.), H$_2$O, brine. The solution was dried over MgSO$_4$, filtered, concentrated. The residue was chromatographed over silica gel (1:1 ethyl acetate/ hexane) to give 0.832 g of 6e (65%).

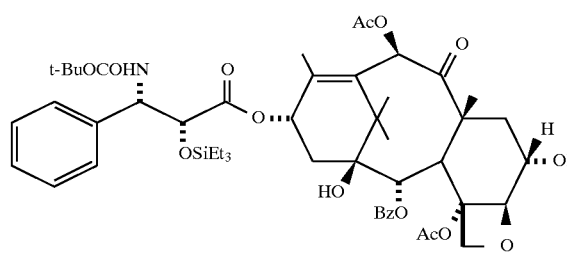

ESILRMS M+H calcd. for C$_{51}$H$_{70}$O$_{15}$N Si: :964. Found: 964.

IR(KBr) 3451(br.), 2957, 1716, 1369, 1271, 1243 cm$^{-1}$.

Anal calcd. for C$_{51}$H$_{69}$O$_{15}$N Si: C, 63.53; H, 7.21; N, 1.45. Found: C, 63.49; H, 7.45; N, 1.32.

$^1$H NMR (CDCl$_3$, 300 MHz) d 8.12(d, J=8.5 Hz, 2H), 7.62–7.25(m, 8H), 6.48(s, 1H), 6.27(t, J=8.8 Hz, 1H), 5.66 (d, J=7.4 Hz, 1H), 5.45(br. d, 1H), 5.29(br. d, 1H), 4.82(s, 1H), 4.53(s, 1H), 4.31(d, J=8.6 Hz, 1H), 4.16–4.08(m, 2H), 3.81(d, J=7.2 Hz, 1H), 2.53(s, 3H), 2.46–2.38(m, 1H), 2.21(s, 4H), 2.06–2.03(m, 2H), 1.90(s, 3H), 1.72(s, 5H), 1.29(s, 9H), 1.25(s, 3H), 1.13(s, 3H), 0.79–0.74(m, 9H), 0.47–0.26(m, 6H).

The alcohol 6e(0.809g, 0.840 mmol) was dissolved in CH$_2$Cl$_2$. NMO and 4A molecular sieves were added and the reaction was stirred for fifteen minutes. TPAP was added and the reaction was allowed to stir overnight. The reaction was filtered through Celite and concentrated. The residue was chromatographed over silica gel (1:1 ethyl acetate/hexane) to give 0.629 g of ketone 11e (78%).

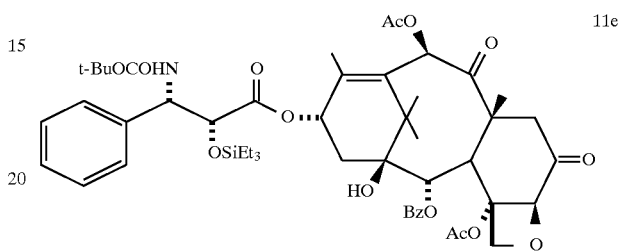

ESILRMS M-H calcd. for C$_{51}$H$_{66}$O$_{15}$N Si: 960. Found: 960.

IR(KBr) 3446(br.), 2958, 1731, 1718, 1269, 1242 cm$^{-1}$.

Anal calcd. for C$_{51}$H$_{67}$O$_{15}$N Si: C, 63.66; H, 7.02; N, 1.46. Found: C, 63.85; H, 7.08; N, 1.37.

$^1$H NMR (CDCl$_3$, 300 MHz) d 8.12(d, J=8.6 Hz, 2H), 7.63–7.27(m, 8H), 6.44(s, 1H), 6.31(t, J=8.9 Hz, 1H), 5.71 (d, J=7.3 Hz, 1H), 5.47(d, J=9.7 Hz, 1H), 5.29(d, J=8.5 Hz, 1H), 4.84(s, 1H), 4.55(d, J=2.0 Hz, 1H), 4.43(d, J=8.5 Hz, 1H), 4.34(d, J=8.4 Hz, 1H), 4.15(d, J=7.2 Hz, 1H), 3.15(d, J=13.9 Hz, 1H), 2.58(s, 3H), 2.49–2.24(m, 3H), 2.21(s, 3H), 1.91(s, 3H), 1.75(s, 1H), 1.67(s, 3H), 1.29(s, 9H), 1.27(s, 3H), 1.13(s, 3H), 0.79–0.74(m, 9H), 0.47–0.26(m, 6H).

The ketone 11e (0.600, 0.624 mmol) was dissolved in EtOH(15 mL) and cooled to 0° C. NaBH$_4$(0.024 g, 0.624 mmol) was added and the reaction was stirred at 0° C. for 30 minutes. The reaction was diluted with EtOAc, quenched with H$_2$O, washed with brine. The solution was dried over MgSO$_4$, filtered, and concentrated. The residue was chromatographed over silica gel (1.5:1 hexane/ethyl acetate) to give 0.48 g of the 20;triethylslyl ether (80%).

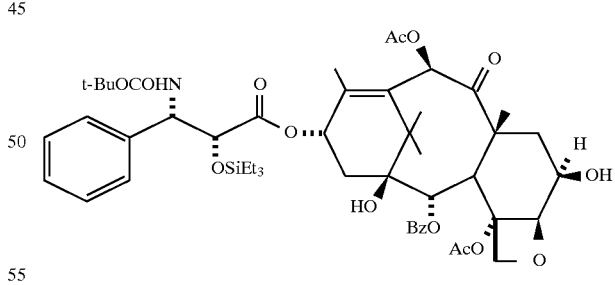

ESILRMS M+H calcd. for C$_{51}$H$_{70}$O$_{15}$N Si: 964. Found: 964.

IR(KBr) 3452(br.), 2956, 1732, 1716, 1271, 1242 cm$^{-1}$.

Anal calcd. for C$_{51}$H$_{69}$O$_{15}$N Si: C, 63.53; H, 7.21; N, 1.45. Found: C, 63.31; H, 7.20; N, 1.40.

$^1$H NMR (CDCl$_3$, 300 MHz) d 8.13(d, J=8.5 Hz, 2H), 7.62–7.24(m, 8H), 6.46(s, 1H), 6.26(t, J=8.7 Hz, 1H), 5.70 (d, J=7.2 Hz, 1H), 5.46(d, J=9.4 Hz, 1H), 5.28(br. d, 1H), 4.98(d, J=8.5 Hz, 1H), 4.52(d, J=1.95 Hz, 1H), 4.47(d, J=8.3 Hz, 1H), 4.22(d, J=8.2 Hz, 1H), 3.68(d, J=7.1 Hz, 1H), 2.74(br. s, 1H), 2.53(s, 3H), 2.43–2.34(m, 1H), 2.23–2.13

(m, 5H), 1.88–1.84(m, 4H), 1.78–1.72(m, 4H), 1.28(s, 9H), 1.22(s, 3H), 1.12(s, 3H), 0.76–0.73(m, 9H), 0.46–0.25(m, 6H).

The silyl ether(0.470 g, 0.488 mmol) was dissolved in $CH_3CN$ and cooled to 0° C. HCl (0.976 mL, 1N, 0.976 mmol) was added and the reaction was stirred at 0° C. for 1 hour. The reaction was diluted with EtOAc, washed with $NaHCO_3$(sat.), $H_2O$, brine. The solution was dried over $MgSO_4$, filtered, and concentrated. The residue was chromatographed over silica gel( 2:1 hexane/ethyl acetate) to give 0.385 g of IIIr (93%).

ESILRMS M+H calcd. for $C_{45}H_{56}O_{15}N$: 850. Found: 850.

IR(KBr) 3448(br.), 2980, 1734, 1715, 1271, 1242 $cm^{-1}$.

Anal calcd. for $C_{45}H_{55}O_{15}N$: C, 63.59; H, 6.52; N, 1.65. Found: C, 63.64; H, 6.20; N, 1.56.

$^1H$ NMR ($CDCl_3$, 300 MHz) d 8.12(d, J=7.2 Hz, 2H), 7.64–7.29(m, 8H), 6.44(s, 1H), 6.21(br. t, 1H), 5.68(d, J=7.1 Hz, 1H), 5.36(d, J=9.4 Hz, 1H), 5.26(br. d, 1H), 4.95(d, J=8.4 Hz, 1H), 4.60(s, 1H), 4.45(d, J=8.4 Hz, 1H), 4.20(d, J=8.3 Hz, 2H), 3.66(d, J=7.0 Hz, 1H), 3.31(s, 1H), 2.73(s, 1H), 5 2.39(s, 3H), 2.33–2.13(m, 5H), 1.87–1.82(m, 4H), 1.77–1.71(m, 4H), 1.31(s, 10H), 1.22(s, 3H), 1.12(s, 3H).

Following substantially the procedures described above, the following compounds within the scope of this invention, can be synthesized.

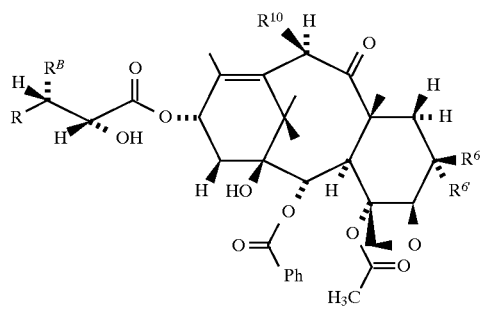

III

| R | $R^B$ | $R^6$ | $R^{6'}$ | $R^{10}$ |
|---|---|---|---|---|
| Phenyl- | tBuOC(O)HN— | —OH | —H | AcO— |
| Phenyl- | tBuOC(O)HN— | —OH | —H | HO— |
| Phenyl- | iPrOC(O)HN— | —H | —OH | AcO— |
| Phenyl- | iPrOC(O)HN— | —H | —OH | HO— |
| Phenyl- | nBuOC(O)HN— | —H | —OH | AcO— |
| Phenyl- | nBuOC(O)HN— | —H | —OH | HO— |
| Phenyl- | tBuOC(O)HN— | —H | —OH | AcO— |
| Phenyl- | tBuOC(O)HN— | —H | —OH | HO— |
| isobutyl- | PhC(O)HN— | —OH | —H | AcO— |
| isobutyl- | PhC(O)HN— | —OH | —H | HO— |
| isobutyl- | tBuOC(O)HN— | —H | —OH | HO— |
| isobutyl- | tBuOC(O)HN— | —H | —OH | AcO— |
| isobutenyl- | PhC(O)HN— | —H | —OH | AcO— |
| isobutenyl- | PhC(O)HN— | —H | —OH | HO— |
| isobutenyl- | tBuOC(O)HN— | —H | —OH | HO— |
| isobutenyl- | tBuOC(O)HN— | —H | —OH | AcO— |
| 3'pF-Ph- | PhC(O)HN— | —OH | —H | AcO— |
| 3'pF-Ph- | tBuOC(O)HN— | —OH | —H | HO— |
| 3'pF-Ph- | PhC(O)HN— | —H | —OH | AcO— |
| 3'pF-Ph- | tBuOC(O)YN— | —H | —OH | HO— |
| 3'pF-Ph- | PhC(O)HN— | —H | —OH | HO— |
| Phenyl- | PhC(O)HN— | —H | —$OCH_3$ | HO— |
| Phenyl- | PhC(O)HN— | —H | —$OCH_3$ | AcO— |
| Phenyl- | PhC(O)HN— | —$OCH_3$ | —H | HO— |
| Phenyl- | PhC(O)HN— | —$OCH_3$ | —H | AcO— |

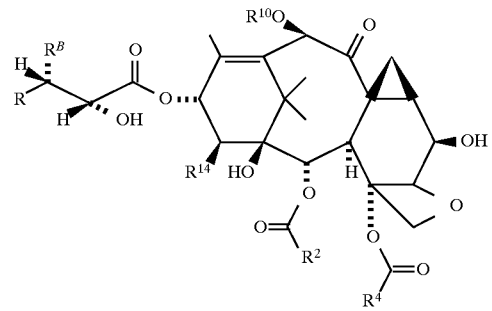

Also:

| R | $R^B$ | $R^2$ | $R^4$ | $R^{10}$ |
|---|---|---|---|---|
| Phenyl- | PhC(O)HN— | -Ph | —$CH_3$ | AcO— |
| Phenyl- | PhC(O)HN— | -Ph | —$CH_3$ | HO— |
| Phenyl- | tBuOC(O)HN— | -Ph | —$CH_3$ | AcO— |
| Phenyl- | tBuOC(O)HN— | -Ph | —$CH_3$ | HO— |
| 3'pF-Ph- | PhC(O)HN— | -Ph | —$CH_3$ | AcO— |
| 3'pF-Ph- | PhC(O)HN— | -Ph | —$CH_3$ | HO— |
| 3'pF-Ph- | tBuOC(O)HN— | -Ph | —$CH_3$ | AcO— |
| 3'pF-Ph- | tBuOC(O)HN— | -Ph | —$CH_3$ | HO— |

The compounds of this invention exhibit antitumor activities in in vivo and/or in vitro models. For example, the following test describes the in vivo test used to evaluate some representative compounds of this invention.

Mice M109 Model

Balb/c x DBA/2 $F_1$ hybrid mice were implanted intraperitoneally, as described by William Rose in Evaluation of Madison 109 Lung Carcinoma as a Model for Screening Antitumor Drugs,*Cancer Treatment Reports,* 65, No. 3–4 (1981), with 0.5 mL of a 2% (w/v) brei of M109 lung carcinoma.

Mice were treated with compounds under study by receiving intraperitoneal injections of various doses on either days 1, 5 and 9 post-tumor implant or days 5 and 8 post-implant. Mice were followed daily for survival until approximately 75–90 days post-tumor implant. One group of mice per experiment remained untreated and served as the control group.

Median survival times of compound-treated (T) mice were compared to the median survival time of the control (C) mice. The ratio of the two values for each compound-treated group of mice was multiplied by 100 and expressed as a percentage (i.e. % T/C in the following table for representative compounds.

| Compound | % T/C (dose in mg/kg/injection; schedule) |
|---|---|
| IIIa | 197% (200 mg/kg/inj; days 5 & 8) |
| IIIc | 128% (100 mg/kg/inj; days 5 & 8) |
| IIId | 158% (100 mg/kg/inj; days 5 & 8) |
| IIIe | 133% (100 mg/kg/inj; days 5 & 8) |
| IIIf | 121% (25 mg/kg/inj; days 5 & 8) |
| IIIg | 159% (200 mg/kg/inj; days 5 & 8) |
| IIIh | 158% (100 mg/kg/inj; days 5 & 8) |
| IIIj | 134% (16 mg/kg/inj; days 5 & 8) |
| IIIk | 135% (50 mg/kg/inj; days 5 & 8) |
| IIIl | 190% (100 mg/kg/inj; days 5 & 8) |
| IIIm | 137% (25 mg/kg/inj; days 5 & 8) |
| IIIn | >315% (100 mg/kg/inj; days 5 & 8) |
| IIIo | 176% (50 mg/kg/inj; days 5 & 8) |
| IIIp | 163% (25 mg/kg/inj; days 5 & 8) |

Mice M109 Model

Balb/c x DBA 2 $F_1$ ($CDF_1$) hybrid mice were implanted subcutaneously (sc) with 0.1mL of a 2% (w/v) brei of M109 lung carcinoma (as described by William Rose in Evaluation of Madison 109 Lung Carcinoma as a Modelfor Screening Antitumor Drugs, Cancer Treatment Reports, 65, No. 3–4 (1981)).

The test compounds and reference drug, paclitaxel, were administered intravenously to groups of mice; each group received a compound at a different dose level, and three or four different dose levels were evaluated per compound. Mice were treated with compounds intravenously, once daily, on days 4, 5, 6, 7, and 8 post-tumor implant. Mice were followed daily for survival until their death or approximately 60–90 days post-tumor implant whichever occurred first. One group of mice per experiment remained untreated and served as the primary control group; a secondary control group was typically included and received 1/10th the tumor inocula of all the other groups of mice (i.e., 0.1 ml of a 0.2% (w/v) brei of M109 lung carcinoma). Tumors were also measured once or,more often, twice weekly to estimate the tumor weight according to the published procedure (ibid).

Median survival times of compound-treated (T) mice were compared to the median survival time of the control (C) mice. The ratio of the two values for each compound-treated group of mice was multiplied by 100 and expressed as a percentage (i.e. % T/C) in the following table for representative compounds. Additionally, the difference between the median time for treated groups and that for the control group to grow tumor to 1 gm, expressed as T-C values in days, is also shown in the following table. The greater the T-C value, the greater the delay in primary tumor growth. Compounds showing % T/C≧125% and/or T-C ≧4.0 days are considered to be active in the M109 sc model provided the aforementioned secondary conrol group does not differ by more than 4 days from the primary control group with regard to the median time to grow 1 gm tumors. When the difference in the time to grow 1 gm tumors in both primary and secondary control groups is greater than 4 days, that difference becomes the criterion for activity.

Advanced Distal Site Antitumor IV Testing of Paclitaxel Derivatives

| Compound | Maximum Effect | | Opt. dose |
| --- | --- | --- | --- |
|  | % T/C | T-C days | (mg/kg/inj) |
| IIIa | 124 | 13.3 | 60 |
| IIIc | 133 | 13.0 | 15 |
| IIId | 124 | 16.3 | 30 |
| IIIe | 124 | 7.8 | 25 |

Thus, another aspect of the instant invention concerns a method for inhibiting human and/or other mammalian tumors which comprises administering to a tumor bearing host an antitumor effective amount of a compound of formula I.

For treating a variety of tumors, the compound of formula I of the present invention may be used in a manner similar to that of paclitaxel, e.g. see Physician's Desk Reference, 49th Edition, Medical Economics, p 682, 1995. The dosage, mode and schedule of administration for the compound of this invention are not particularly restricted; an oncologist skilled in the art of cancer treatment will be able to ascertain, without undue experimentation, an appropriate treatment protocol for administering the compound of the present invention. Thus the compound of formula I may be administered via any suitable route of administration, parenterally or orally. Parenteral administration includes intravenous, intraperitoneal, intramuscular, and subcutaneous administration.

The doses utilized to implement the methods in accordance with the invention are the ones that make it possible to administer prophylactic treatment or to evoke a maximal therapeutic response. The doses vary, depending on the type of administration, the particular product selected, and the personal characteristics of the subject to be treated. In general, the doses are the ones that are therapeutically effective for the treatment of disorders caused by abnormal cell proliferation. The products in accordance with the invention can be administered as often as necessary in order to obtain the desired therapeutic effect. Some patients may respond rapidly to relatively high or low doses, and then require mild maintenance or no maintenance dose at all. Via the iv route, the dosage may be, for example, in the range of about 20 to about 500 mg/m$^2$ over 1 to 100 hours. Via the oral route, the dosage may be in the range of 5–1000 mg/kg/day of body weight. The actual dose used will vary according to the particular composition formulated, the route of administration, and the particular site, host and type of tumor being treated. Many factors that modify the action of the drug will be taken into account in determining the dosage including age, weight, sex, diet and the physical condition of the patient.

The present invention also provides pharmaceutical formulations (compositions) containing an antitumor effective amount of compound of formula I in combination with one or more pharmaceutically acceptable carriers, excipients, diluents or adjuvants. The compositions can be prepared in accordance with conventional methods. Examples of formulating paclitaxel or derivatives thereof may be found in, for example, U.S. Pat. Nos. 4,960,790 and 4,814,470, and such examples may be followed to formulate the compound of this invention. For example, compound of formula I may be formulated in the form of tablets, pills, powder mixtures, capsules, injectables, solutions, suppositories, emulsions, dispersions, food premix, and in other suitable forms. It may also be manufactured in the form of sterile solid compositions, for example, freeze dried and, if desired, combined with other pharmaceutically acceptable excipients. Such solid compositions can be reconstituted with sterile water, physiological saline, or a mixture of water and an organic solvent, such as propylene glycol, ethanol, and the like, or some other sterile injectable medium immediately before use for parenteral administration.

Typical of pharmaceutically acceptable carriers are, for example, manitol, urea, dextrans, lactose, potato and maize starches, magnesium stearate, talc, vegetable oils, polyalkylene glycols, ethyl cellulose, poly(vinylpyrrolidone), calcium carbonate, ethyl oleate, isopropyl myristate, benzyl benzoate, sodium carbonate, gelatin, potassium carbonate, silicic acid. The pharmaceutical preparation may also contain nontoxic auxiliary substances such as emulsifying, preserving, wetting agents, and the like as for example, sorbitan monolaurate, triethanolamine oleate, polyoxyethylene monostearate, glyceryl tripalmitate, dioctyl sodium sulfosuccinate, and the like.

What is claimed is:

1. A compound of formula I, or a pharmaceutically acceptable salt thereof

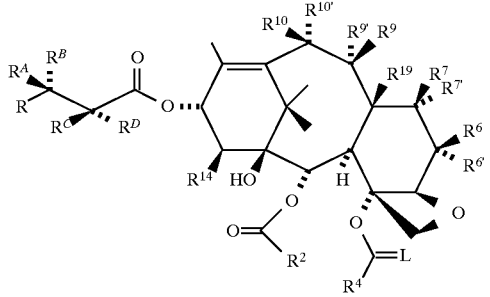

wherein:

R is hydrogen, $C_{1-6}$ alkyl, $C_{2-6}$ alkenyl, $C_{2-6}$ alkynyl, $C_{3-6}$ cycloalkyl, $C_{3-6}$ cycloalkenyl, cyclic 3–7 membered ring containing either one or two heteroatoms, heteroaryl or —$Z^1$—$R^3$;

$Z^1$ is a direct bond, $C_{1-6}$ alkyl, or —O—$C_{1-6}$ alkyl;

$R^3$ is aryl, substituted aryl, $C_{3-6}$ cycloalkyl, $C_{3-6}$ cycloalkenyl, cyclic 3–7 membered ring containing either one or two heteroatoms, or heteroaryl;

$R^A$ and $R^B$ are independently hydrogen, —NHC(O)R, —NHC(O)OR, —NHC(O)NHR, —NHC(O)N(R)$_2$, —NHS(O)$_m$R, —NHP(=O)(OR)$_2$, —NHP=S(OR)$_2$, where m is 1 or 2;

$R^C$ and $R^D$ are independently hydrogen, hydroxy, fluoro, —OC(O)R$^x$, —OC(O)OR$^x$, OP(O)(OH)$_2$, OCH$_2$OP(O)(OH)$_2$, —OCH$_2$OCH$_2$OP(=O)(OH)$_2$, —(OCH$_2$)$_n$OC=OCH$_2$NHR$^x$, —(OCH$_2$)$_n$OC(=O)CH$_2$NR'$_6$R'$_7$, where n is 0–3, —OCOCH$_2$CH$_2$NH$_3^+$ HCOO$^-$, —OCOCH$_2$CH$_2$COOH, —OCO(CH$_2$)COOH, —OC(O)CH(R")NH$_2$, —OC(O)(CH$_2$)$_n$NR$^F$R$^G$, where n is 0–3, —OC(O)CH$_2$CH$_2$C(O)OCH$_2$CH$_2$OH or —OC(O)—Z—C(O)—R';

Z is ethylene, propylene, —CH=CH—, 1,2-cyclohexane or 1,2-phenylene;

R' is —OH, —OH base, —NR'$_2$R'$_3$, —OR'$_3$, —SR'$_3$, or —OCH$_2$C(O)NR'$_4$R'$_5$;

R'$_2$ is —H or —CH$_3$;

R'$_3$ is —(CH$_2$)$_n$NR'$_6$R'$_7$ or (CH$_2$)$_n$N$^+$R'$_6$R'$_7$R'$_8$, where n is 1–3;

R'$_4$ is —H or —C$_1$–C$_4$ alkyl;

R'$_5$ is —H, —C$_1$–C$_4$ alkyl, benzyl, hydroxyethyl, —CH$_2$CO$_2$H or dimethylaminoethyl;

R'$_6$ and R'$_7$ are independently —H, —CH$_3$, —CH$_2$CH$_3$, benzyl or R'$_6$ and R'$_7$ together with the nitrogen of NR'$_6$R'$_7$ form a pyrrolidino, piperidino, morpholino, or N-methylpiperizino group;

R'$_8$ is —CH$_3$, —CH$_2$CH$_3$ or benzyl;

X is halide;

base is NH$_3$, (HOC$_2$H$_4$)$_3$N, N(CH$_3$)$_3$, CH$_3$N(C$_2$H$_4$)$_2$NH, NH$_2$(CH$_2$)$_6$NH$_2$, N-methylglucamine, NaOH or KOH;

$R^F$ and $R^G$ are independently —H or —C$_1$–C$_3$ alkyl, or $R^F$ and $R^G$ taken together with the nitrogen of NRFRG form a pyrrolidino, piperidino, morpholino or N-methylpiperizino groups;

R" is —H, —CH$_3$, —CH$_2$CH(CH$_3$)$_2$, —CH(CH$_3$) CH$_2$CH$_3$, —CH(CH$_3$)$_2$, —CH$_2$phenyl, —(CH$_2$)$_3$NH$_2$, —(CH$_2$)$_4$NH$_2$, —CH$_2$CH$_2$COOH, —(CH$_2$)$_3$NHC(=NH)NH$_2$, the residue of the amino acid proline, —OC(O)CH=CH$_2$, —C(O)CH$_2$CH$_2$C(O) NHCH$_2$CH$_2$SO$_3$—Y+ or —OC(O)CH$_2$CH$_2$C(O) NHCH$_2$CH$_2$SO$_3$—Y+;

Y+ is Na+ or N+(Bu)$_4$;

$R^2$ is R$^x$, R$^x$ or R$^{y"}$;

$R^4$ is $C_{1-6}$ alkyl, $C_{2-6}$ alkenyl, $C_{2-6}$ alkynyl, $C_{3-6}$ cycloalkyl, $C_{3-6}$ cycloalkenyl, $C_{3-6}$ heteroaryl, —O—$C_{1-6}$ alkyl, —O—$C_{2-6}$ alkenyl, —O—$C_{2-6}$ alkynyl, —CH$_2$OCH$_3$, —CH$_2$OCH$_2$OCH$_3$, —CH$_2$OCH$_2$OCH$_2$CH$_3$, —CH$_2$CH$_2$OCH$_3$, CHOCH$_2$ (an oxirane) or —S—$C_{1-6}$ alkyl;

L is O or S;

$R^6$ and $R^{6'}$ are independently hydrogen, hydroxy, —O—$C_{1-6}$ alkyl, —OC(O)R$^x$, —(O)OR$^x$; —OC(O) NHR$^x$; —OC(O)NR'$_6$R'$_7$, —OCH$_2$OR, —OC(R$^x$)$_2$OR, —OCHR$^x$OR, —OCH$_2$OCH$_2$OCH$_3$, —OCH$_2$OCH$_2$OCH$_3$, —OCH$_2$OCH$_2$CH$_2$OCH$_3$, —OCH$_2$OCH$_2$CH$_2$OH, —OCH$_2$SR, —OCH$_2$OCH$_2$SCH$_3$, OP(O)(OH)$_2$, OCH$_2$OP(O)(OH)$_2$, —OCH$_2$OCH$_2$OP(O)(OH)$_2$, —(OCH2)$_n$OC=OCH$_2$NHR$^x$, —(OCH$_2$)$_n$OC(=O)CH$_2$NR'$_6$R'$_7$, where n is 0–3, —$C_{1-6}$ alkyl, —CH$_2$OR, —CH$_2$SCH$_3$, —CH$_2$OCH$_2$SCH$_3$, —OC(R$^x$)$_2$SR, —OCHR$_x$SR,— OCOCH$_2$CH$_2$NH$_3^+$ HCOO$^-$, —OCOCH$_2$CH$_2$COOH, —OCO(CH$_2$)$_3$COOH, —OC(O)(CH$_2$)$_n$NR$^F$R$^G$, where n is 0–3, —OC(O)—Z—C(O)—R' or —C(O)CH$_2$CH$_2$C(O)OCH$_2$CH$_2$OH, provided that both $R^6$ and $R^{6'}$ cannot be hydrogen, $R^6$ and $R^{6'}$ together can form an oxo group or a thiocarbonyl group, or $R^6$ and $R^{6'}$ together can form a carbon nitrogen double bond of formula —C=N—R, —C=N—OR or —C=N—NHR —C=N—NR'$_6$R'$_7$, where R is as previously defined, provided it is not hydrogen;

$R^{7'}$ is hydrogen; $R^7$ is hydrogen or when taken together with $R^{19}$ can form a cyclopropane ring;

$R^9$ and $R^{9'}$ are independently hydrogen, hydroxy, or together form an oxo (keto) group;

$R^{10}$ and $R^{10'}$ are independently hydrogen, hydroxy, —OC(O)R$^x$, —OC(O)OR$^x$, $C_{1-6}$ alkyl, —OCH$_2$OCH$_3$, —OCH$_2$OCH$_2$OCH$_3$, —OCH$_2$OCH$_2$OCH$_2$CH$_3$, —OCH$_2$OCH$_2$CH$_2$OCH$_3$, —OCH$_2$OCH$_2$CH$_2$OH, —OCH$_2$SCH$_3$, —OCH$_2$OCH$_2$SCH$_3$, —OC(O) NR'$_6$R'$_7$, —OP(O)(OH)$_2$, —OCH$_2$OP(O)(OH)$_2$, —OCH$_2$OCH$_2$OP(O)(OH)$_2$, —(OCH$_2$)$_n$OC=OCH$_2$NHR$^x$, —(OCH$_2$)$_n$OC(=O)CH$_2$NR'$_6$R'$_7$, where n is 0–3, $C_{1-6}$alkyl, —(CH$_2$)$_3$C(O)R$^x$, —(CH$_2$)$_3$C(O)OR$^x$, —(CH$_2$)$_3$CN, —OCOCH$_2$CH$_2$NH$_3^+$ HCOO, —OCOCH$_2$CH$_2$COOH, —OCO(CH$_2$)$_3$COOH, —OC(O)—Z—C(O)—R'—OC(O)(CH$_2$)$_n$NR$^F$R$^G$, where n is 0–3, or —OC(O)CH$_2$CH$_2$C(O) OCH$_2$CH$_2$OH;

$R^{14}$ is hydrogen, hydroxy, —OC(O)R$^x$, —OC(O)OR$^x$, —O—$C_{1-6}$ alkyl, —OCH$_2$OCH$_3$, —OCH$_2$OCH$_2$OCH$_3$, —OCH$_2$OCH$_2$OCH$_2$CH$_3$, OC)H$_2$OCH$_2$CH$_2$OCH3., —OCH$_2$OCH$_2$CH$_2$OH, —OCH2SCH$_3$, —OCH$_2$OCH$_2$SCH$_3$, OP(O)(OH)$_2$, OCH$_2$OP(O)(OH)$_2$, —OCH$_2$OCH$_2$OP(O)(OH)$_2$, —(OCH$_2$)$_n$OC=OCH$_2$NHR$^x$, or —(OCH$_2$)$_n$OC(=O) CH$_2$NR'$_6$R'$_7$, where n is 0–3;

$R^{19}$ is methyl, hydroxymethyl, or $R^{19}$ and $R^7$ together can form a cyclopropane ring with the proviso that when these substituents are cyclopropane ring then $R^{7'}$ is hydrogen;

$R^x$ is $C_{1-6}$ alkyl, $C_{2-6}$ alkenyl, $C_{2-6}$ alkynyl, $C_{3-6}$ cyclo alkyl, any of which groups can be optionally substituted with one to six of the same or different halogen atoms;

$R^y$ is a radical of the formula

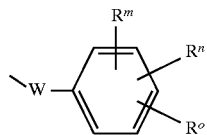

wherein W is a bond and $R^m$, $R^n$, and $R^o$ are independently hydrogen, nitro, cyano, azido, amino, $C_{1-6}$ alkylamino, di-$C_{1-6}$ alkylamino, halogen, $C_{1-6}$ alkyl, hydroxy or $C_{1-6}$ alkoxy; and $R^y$ is a radical of the formula

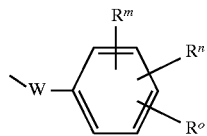

wherein W is $C_{1-6}$ alkyl or —$OC_{1-6}$ alkyl, and $R^m$, $R^n$, and $R^o$ are independently hydrogen, nitro, cyano, azido, amino, $C_{1-6}$ alkylamino, di-$C_{1-6}$ alkylamino, halogen, $C_{1-6}$ alkyl, hydroxy or $C_{1-6}$ alkoxy.

2. A compound of claim 1 having the formula II, or a pharmaceutically acceptable salt thereof,

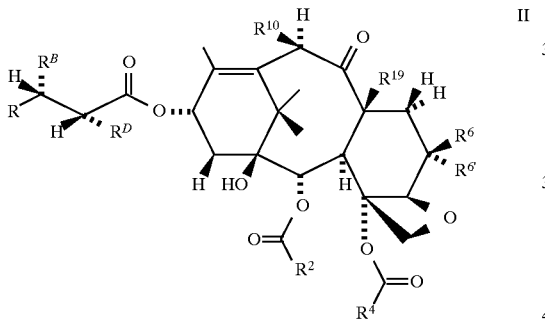

wherein:
R is 2-furanyl (2-furyl), 2-thienyl, 3-furanyl (3-furyl), 3-thienyl, phenyl, napthyl, 4-hydroxyphenyl, 4-methoxyphenyl, 4-fluorophenyl, 4-trifluoromethylphenyl, 2-propynyl, benzyl, phenethyl, phenylethenyl, 3,4-dimethoxyphenyl, 2-(2-furanyl)ethenyl, 2-methylpropyl, $C_{3-6}$ cycloalkyl, cyclohexylmethyl, cyclohexylethyl, $C_{3-6}$ alkyl, $C_{3-6}$ alkenyl, t-butyl, or —$Z^1$—$R^3$;

$Z^1$ is a direct bond;

$R^3$ is aryl or substituted aryl;

$R^B$ is —NHC(O)Ph, where Ph is substituted or unsubstituted, —NHC(O)O($C_{1-6}$ alkyl), —NHC(O)OCH$_2$Ph, —NHC(O)T, where T is a 3–7 membered ring containing either one or two heteroatoms, —NHC(O)NHR or —NHC(O)N(R)$_2$;

$R^D$ is hydroxy, OP(O)(OH)$_2$, OCH$_2$OP(O)(OH)$_2$, —OCH$_2$OCH$_2$OP(O)(OH)z, (OCH$_2$)$_m$OC=OCH$_2$NHR$^x$, —(OCH$_2$)$_m$OC(=O)CH$_2$NR'$_6$R'$_7$ where m is 0–3, —OC(O)CH$_3$, —OC(O)OCH$_2$C(Cl)$_3$, —OCOCH$_2$CH$_2$NH$_3^+$ HCOO$^-$, —NHC(O)phenyl, —NHC(O)OC(CH$_3$)$_3$, —OCOCH$_2$CH$_2$COOH, —OCO(CH2)COOH, —OC(O)—Z—C(O)—R', —OC(O)(CH$_2$)$_n$NR$^F$R$^G$, where n is 0–3, or —OC(O)CH$_2$CH$_2$C(O)OCH$_2$CH$_2$OH;

$R^2$ is -phenyl or substituted phenyl;

$R^4$ is methyl, $C_{1-4}$ alkyl, $C_{3-5}$ cyclo alkyl, —O—$C_{1-4}$ alkyl, —CH$_2$OCH$_3$, CHOCH$_2$(oxirane), or —S—$C_{1-4}$ alkyl;

$R^6$ and $R^{6'}$ are independently hydrogen, hydroxy, —O—$C_{1-6}$ alkyl, —OC(O)R$^x$, —OC(O)OR$^x$, —OC(O)NHR$^x$, —OC(O)NR$_2$, —OCH$_2$OR, —OCH$_2$OCH$_2$OCH$_3$, —OCH$_2$OCH$_2$OCH$_2$CH$_3$, —OCH$_2$OCH$_2$CH$_2$OCH3, —OCH20CH$_2$CH$_2$OH, —OC(R$^x$)$_2$OR, —OCHR$^x$OR, —OCH$_2$SR, —OCH$_2$OCH$_2$SCH$_3$, —OC(R$^x$)$_2$SR, —OCHR$^x$SR, OP(O)(OH)$_2$, OCH$_2$OP(O)(OH)$_2$, —OCH$_2$OCH$_2$OP(O)(OH)$_2$, —(OCH$_2$)$_n$OC=OCH$_2$NHRX, —(OCH$_2$)$_n$OC(=O)CH$_2$NR'$_6$R'$_7$, where n is 0–3, —$C_{1-6}$ alkyl, —CH$_2$OR, —CH$_2$OCH$_2$OCH$_3$, —CH$_2$OCH$_2$OCH$_2$CH$_3$, —CH$_2$OCH$_2$CH$_2$OCH$_3$, —CH$_2$OCH$_2$CH$_2$OH, —CH$_2$SCH$_3$, —CH$_2$OCH$_2$SCH$_3$, provided that both $R^6$ and R6' cannot be hydrogen, $R^6$ and $R^{6'}$ can together form an oxo group, or $R^6$ and $R^{6'}$ together can form a carbon nitrogen double bond of formula C=N—R or —C=N—OR;

$R^{10}$ is hydrogen, hydroxy, —OC(O)R$^x$, —OC(O)ORX, —O—$C_{1-6}$ alkyl, —OCH$_2$OCH$_3$, —OCH$_2$OCH$_2$OCH$_3$, —OCH$_2$OCH$_2$OCH$_2$CH$_3$, —OCH$_2$OCH$_2$CH$_2$OCH$_3$, —OCH$_2$OCH$_2$CH$_2$OH, —OCH$_2$SCH$_3$, —OCH20CH$_2$SCH$_3$, —OC(O)NR'$_6$R'$_7$ $C_{1-6}$alkyl, —(CH$_2$)$_3$C(O)R$^x$, —(CH$_2$)$_3$C(O)ORX or —(CH$_2$)$_3$CN; and $R^{19}$ is —CH$_3$, or $R^{19}$ and $R^7$ together can form a cyclopropane ring with the proviso that when these substituents are cyclopropane ring than R7' is hydrogen.

3. A compound of claim 1 having the formula III, or a pharmaceutically acceptable salt thereof,

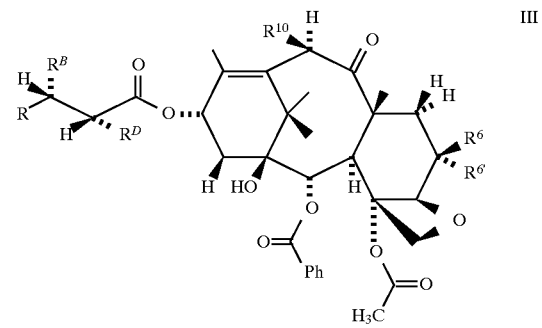

wherein:
R is 2-furanyl (2-furyl), 2-thienyl, 3-furanyl (3-furyl), 3-thienyl, phenyl, napthyl, 4-hydroxyphenyl, 4-methoxyphenyl, 4-fluorophenyl, 4-trifluoromethylphenyl, 2-propynyl, benzyl, phenethyl, phenylethenyl, 3,4-dimethoxyphenyl, 2-(2-furanyl)ethenyl, 2-methylpropyl, $C_{3-6}$ cycloalkyl, cyclohexylmethyl, cyclohexylethyl, $C_{3-6}$ alkyl, $C_{3-6}$ alkenyl, or —$Z^1$—$R^3$;

$Z^1$ is a direct bond;

$R^3$ is aryl or substituted aryl;

$R^B$ is —NHC(O)Ph, where Ph is substituted or unsubstituted, —NHC(O)O($C_{1-6}$ alkyl), —NHC(O)OCH$_2$Ph, —NHC(O)T, where T is a 3–7 membered ring containing either one or two heteroatoms, —NHC(O)NHR or —NHC(O)N(R)$_2$;

$R^D$ is hydroxy, OP(O)(OH)$_2$, OCH$_2$OP(O)(OH)$_2$, —OCH$_2$OCH$_2$OP(O)(OH)$_2$, —(OCH$_2$)$_m$OC=OCH$_2$NHR$^x$, —(OCH$_2$)$_m$OC(=O)

$CH_2NR'_6R'_7$, where m is 0–3, —OC(O)CH$_3$, —OC(O)OCH$_2$C(Cl)$_3$, —OCOCH$_2$CH$_2$NH$_3^+$ HCOO$^-$, —NHC(O)phenyl, —NHC(O)OC(CH$_3$)$_3$, —OCOCH$_2$CH$_2$COOH, —OCO(CH$_2$)$_3$COOH, —OC(O)—Z—C(O)—R', —OC(O)(CH$_2$)$_n$NR$^F$R$^G$, where n is 0–3 or —OC(O)CH$_2$CH$_2$C(O)OCH$_2$CH$_2$OH;

R$^6$ and R$^{6'}$ are independently hydrogen, hydroxy, —O—C$_{1-6}$ alkyl, —OC(O)R$^x$, —OC(O)OR$^x$, —OC(O)NHR$^x$, —OC(O)NR$_2$, —OCH$_2$OR, —OCH$_2$OCH$_2$OCH$_3$, —OCH$_2$OCH$_2$OCH$_2$CH$_3$., —OCH$_2$OCH$_2$CH$_2$OCH$_3$, —OCH$_2$OCH$_2$CH$_2$OH, —OC(R$^x$)$_2$OR, —OCHR$^x$OR, —OCH$_2$SR, —OCH$_2$OCH$_2$SCH$_3$, OC(R$^x$)$_2$SR, —OCHR$^x$SR, OP(O)(OH)$_2$, OCH$_2$OP(O)(OH)$_2$, —OCH$_2$OCH$_2$OP(O)(OH)$_2$, —(OCH$_2$)$_n$OC=OCH$_2$NHR$^x$, —(OCH$_2$)$_n$OC(=O)CH$_2$NR'$_6$R'$_7$, where n is 0–3, —C$_{1-6}$ alkyl, —CH$_2$OR, —CH$_2$OCH$_2$OCH$_3$, —CH$_2$OCH$_2$OCH$_2$CH$_3$, —CH$_2$OCH2CH$_2$OCH$_3$, —CH$_2$OCH$_2$CH$_2$OH, —CH$_2$SCH$_3$, —CH$_2$OCH$_2$SCH$_3$, provided that both R$^6$ and R6' cannot be hydrogen, R$^6$ and R$^{6'}$ together can forrn an oxo group, or R$^6$ and R6' together can forn a carbon nitrogen double bond of formula C=N—R or —C=N—OR; and R$^{10}$ is hydrogen, hydroxy, —OC(O)R$^x$, —OC(O)OR$^x$, —O—C$_{1-6}$ alkyl, —OCH$_2$OCH$_3$, —CH20CH$_2$OCH$_3$, —OCH$_2$OCH$_2$OCH$_2$CH$_3$, —OCH$_2$OCH$_2$CH$_2$OCH$_3$, —OCH$_2$OCH$_2$CH$_2$OH, —OCH$_2$SCH$_3$, —OCH$_2$OCH$_2$SCH$_3$ or —OC(O)NR'$_6$R'$_7$.

4. A compound of claim 2, wherein

R$^B$ is —NHC(O)OtBu, —NHC(O)OnBu, —NHC(O)OiPr, —NHC(O)OCH$_2$Ph, —NHC(O)Ph or NHC(O)—2-furyl;

R$^2$ is phenyl, mono- or di-substituted phenyl;

R$^4$ is methyl;

R$^6$ and R$^{6'}$ are independently —H, —OH, —OCH$_3$, —OCH$_2$OCH$_3$, —OCH$_2$SCH$_3$ or —CH$_2$OCH$_3$; and R$^{10}$ is —H, —OH or —OC(O)CH$_3$.

5. A compound of claim 3, wherein:

R is phenyl, isobutenyl, p-fluoro-phenyl or p-methyl-phenyl;

R$^B$ is —NHC(O)OtBu, —NHC(O)OnBu, —NHC(O)OiPr, —NHC(O)OCH$_2$Ph, —NHC(O)Ph or NHC(O)-2-furyl;

R$^D$ is —OH;

R$^6$ and R6' are independently —H, —OCH$_3$, —OH, —OCH$_2$OCH$_3$, —OCH$_2$SCH$_3$ or —CH$_2$OCH$_3$; and R$^{10}$ is —H, —OH or —OC(O)CH$_3$.

6. A compound of claim 3 wherein R$^6$ is —OH, and R$^{6'}$ is —H.

7. A compound of claim 1 having the formula IV

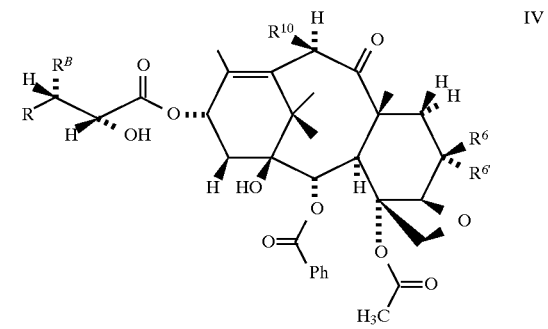

selected from the group consisting of compounds IIIa-IIIr as identified below:

| Cmpd. | R | R$^B$ | R$^6$ | R$^{6'}$ | R$^{10}$ |
|---|---|---|---|---|---|
| IIIa | Ph- | PhCOHN— | —H | —OH | AcO— |
| IIIb | Ph- | PhCOHN— | —H | —OH | H— |

| Cmpd. | R | R$^B$ | R$^6$ & R$^{6'}$ together | R$^{10}$ |
|---|---|---|---|---|
| IIIc | Ph- | PhCOHN— | =O | AcO— |

| Cmpd. | R | R$^B$ | R$^6$ | R$^{6'}$ | R$^{10}$ |
|---|---|---|---|---|---|
| IIId | Ph- | PhCOHN— | —OH | —H | AcO— |
| IIIe | Ph- | PhCOHN— | —OH | —CH$_3$ | AcO— |
| IIIf | 2-furyl- | tBuO$_2$CHN— | —H | —OH | AcO— |
| IIIg | Ph- | nC$_5$H$_{11}$COHN | —H | —OH | AcO— |
| IIIh | pF-Ph- | PhCOHN— | —H | —OH | AcO— |

| Cmpd. | R | R$^B$ | R$^6$ & R$^{6'}$ together | R$^{10}$ |
|---|---|---|---|---|
| IIIi | 2-furyl- | tBuO$_2$CHN— | =O | AcO— |

| Cmpd. | R | R$^B$ | R$^6$ | R$^{6'}$ | R$^{10}$ |
|---|---|---|---|---|---|
| IIIj | 2-furyl- | tBuO$_2$CHN— | —OH | —H | AcO— |
| IIIk | Ph- | nC$_5$H$_{11}$COH | —OH | —H | AcO— |
| IIIl | pF-Ph- | PhCOHN— | —OH | —H | AcO— |
| IIIm | Ph- | PhCOHN— | —H | —OCH$_2$OCH$_3$ | AcO— |
| IIIn | Ph- | PhCOHN— | —OCH$_2$OCH$_3$ | —H | AcO— |
| IIIq | —CH=C(CH$_3$)$_2$ | PhCOHN— | —OH | —H | AcO— |
| IIIr | Ph- | tBuO$_2$CHN— | —OH | —H | AcO— |

| Cmpd. | R | R$^B$ | R$^6$ & R$^{6'}$ together | R$^{10}$ |
|---|---|---|---|---|
| IIIo | Ph- | PhCOHN— | =N—OH(E) | AcO— |
| IIIp | Ph- | PhCOHN— | =N—OH(Z) | AcO— |

8. The compound IIId of claim 7, including pharmaceutically acceptable salts thereof.

9. A pharmaceutical formulation which comprises an antitumor effective amount of a compound of formula I as claimed in any one of claims 1–8.

10. A method for inhibiting tumor growth in a mammalian host which comprises administering to said mammal a tumor-growth inhibiting amount of a compound of formula I as claimed in any one of claims 1–8.

* * * * *